United States Patent
Konradi et al.

(10) Patent No.: US 11,771,688 B2
(45) Date of Patent: Oct. 3, 2023

(54) PYRIDINE DERIVATIVES SUBSTITUTED BY HETEROCYCLIC RING AND AMINO GROUP

(71) Applicant: Amplyx Pharmaceuticals, Inc., San Diego, CA (US)

(72) Inventors: Andrei W. Konradi, Burlingame, CA (US); Jonathan A. Covel, San Diego, CA (US); Michael Grey, San Diego, CA (US)

(73) Assignee: AMPLYX PHARMACEUTICALS, INC., New York, NY (US)

( * ) Notice: Subject to any disclaimer, the term of this patent is extended or adjusted under 35 U.S.C. 154(b) by 161 days.

(21) Appl. No.: 17/253,885

(22) PCT Filed: Jun. 24, 2019

(86) PCT No.: PCT/US2019/038780
§ 371 (c)(1),
(2) Date: Dec. 18, 2020

(87) PCT Pub. No.: WO2020/005860
PCT Pub. Date: Jan. 2, 2020

(65) Prior Publication Data
US 2021/0275510 A1    Sep. 9, 2021

Related U.S. Application Data

(60) Provisional application No. 62/722,539, filed on Aug. 24, 2018, provisional application No. 62/689,535, filed on Jun. 25, 2018.

(51) Int. Cl.
| | |
|---|---|
| A61K 31/444 | (2006.01) |
| A61P 31/10 | (2006.01) |
| A61K 31/137 | (2006.01) |
| A61K 31/343 | (2006.01) |
| A61K 31/4174 | (2006.01) |
| A61K 31/4196 | (2006.01) |
| A61K 31/4439 | (2006.01) |
| A61K 31/496 | (2006.01) |
| A61K 31/506 | (2006.01) |
| A61K 31/513 | (2006.01) |
| A61K 31/675 | (2006.01) |
| A61K 31/7048 | (2006.01) |
| A61K 31/706 | (2006.01) |
| A61K 38/12 | (2006.01) |
| C07B 59/00 | (2006.01) |
| C07D 413/14 | (2006.01) |
| C07H 15/26 | (2006.01) |

(52) U.S. Cl.
CPC .......... *A61K 31/444* (2013.01); *A61K 31/137* (2013.01); *A61K 31/343* (2013.01); *A61K 31/4174* (2013.01); *A61K 31/4196* (2013.01); *A61K 31/4439* (2013.01); *A61K 31/496* (2013.01); *A61K 31/506* (2013.01); *A61K 31/513* (2013.01); *A61K 31/675* (2013.01); *A61K 31/706* (2013.01); *A61K 31/7048* (2013.01); *A61K 38/12* (2013.01); *A61P 31/10* (2018.01); *C07B 59/004* (2013.01); *C07D 413/14* (2013.01); *C07H 15/26* (2013.01)

(58) Field of Classification Search
CPC ................ A61K 31/444; A61K 31/137; A61K 31/343; A61K 31/4174; A61K 31/4196; A61K 31/4439; A61K 31/496; A61K 31/506; A61K 31/513; A61K 31/675; A61K 31/7048; A61K 31/706; A61K 38/12; A61P 31/10; C07B 59/004; C07D 413/14; C07H 15/26
USPC ......................................................... 514/25
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 7,691,882 B2 | 4/2010 | Tanaka et al. |
| 8,058,444 B2 | 11/2011 | Niijima et al. |
| 8,153,662 B2 | 4/2012 | Tanaka et al. |
| 8,158,657 B2 | 4/2012 | Tanaka et al. |
| 8,188,119 B2 | 5/2012 | Tanaka |
| 8,507,530 B2 | 8/2013 | Tanaka et al. |
| 8,513,287 B2 | 8/2013 | Matsukura |
| 8,841,327 B2 | 9/2014 | Tanaka et al. |

(Continued)

FOREIGN PATENT DOCUMENTS

| | | |
|---|---|---|
| EP | 1944303 A1 | 7/2008 |
| EP | 2345328 A1 | 7/2011 |

(Continued)

OTHER PUBLICATIONS

Kohchi et al. Design and synthesis of novel prodrugs of 2'-deoxy-2'-methylidenecytidine activated by membrane dipeptidase overexpressed in tumor tissues. Bioorganic & Medicinal Chemistry Letters 17 (2007) 2241-2245. (Year: 2007).*

(Continued)

*Primary Examiner* — Yih-Horng Shiao
(74) *Attorney, Agent, or Firm* — Beau Burton

(57) ABSTRACT

Described herein are pyridine derivatives substituted by heterocycle and amino groups and pharmaceutical compositions comprising said compounds. The disclosed compounds are antifungal agents. The subject compounds and compositions are useful for the treatment of fungal diseases and infections.

14 Claims, No Drawings

(56) References Cited

U.S. PATENT DOCUMENTS

| | | |
|---|---|---|
| 2003/0045554 A1 | 3/2003 | Sankaranarayanan |
| 2006/0247237 A1 | 11/2006 | Freyne et al. |
| 2007/0105904 A1 | 5/2007 | Tanaka et al. |
| 2009/0082403 A1 | 3/2009 | Tanaka et al. |
| 2009/0233883 A1 | 9/2009 | Matsukura |
| 2010/0004235 A1 | 1/2010 | Schirok et al. |
| 2010/0105737 A1* | 4/2010 | Tanaka .................... A61P 31/10 546/256 |
| 2010/0168173 A1 | 7/2010 | Tanaka et al. |
| 2010/0331282 A1 | 12/2010 | Matsukura |
| 2011/0201649 A1 | 8/2011 | Matsuzaki et al. |
| 2011/0263845 A1 | 10/2011 | Niijima et al. |
| 2012/0029023 A1 | 2/2012 | Tanaka et al. |
| 2021/0163461 A1 | 6/2021 | Trzoss et al. |

FOREIGN PATENT DOCUMENTS

| | | |
|---|---|---|
| EP | 2351752 A1 | 8/2011 |
| EP | 2628738 A1 | 8/2013 |
| WO | WO-2011051198 A2 | 5/2011 |
| WO | WO2015/002080 A1 | 1/2015 |
| WO | WO-2019113542 A1 | 6/2019 |
| WO | WO-2020005860 A1 | 1/2020 |
| WO | WO-2020247804 A1 | 12/2020 |

OTHER PUBLICATIONS

Al-Muhammed et al. In-vivo studies on dexamethasone sodium phosphate liposomes. J Microencapsul. 13(3):293-306 (1996).

Arendrup et al. APX001A In Vitro Activity against Contemporary Blood Isolates and Candida auris Determined by the EUCAST Reference Method. Antimicrob Agents Chemother 62(10):e01225-18 (2018).

Berge et al. Pharmaceutical Salts. Journal of Pharmaceutical Sciences 66(1):1-19 (Jan. 1977).

Berkow et al. Activity of novel antifungal compound APX001A against a large collection of Candida auris. J Antimicrob Chemother 73(11):3060-3062 (2018).

Bundgard, H. Design of Prodrugs. 1985; pp. 7-9, 21-24 (Elsevier, Amsterdam).

Chonn et al. Recent advances in liposomal drug-delivery systems. Curr Opin Biotechnol. 6(6):698-708(1995).

Covel et al. Chapter 12: The Discovery of Manogepix/Fosmanogepix and Other GWT1 Inhibitors for the Treatment of Invasive Fungal Infections. 2019 Medicinal Chemistry Reviews vol. 54 (18 pgs).

Eyles et al. Oral delivery and fate of poly(lactic acid) microsphere-encapsulated interferon in rats. J Pharm Pharmacol. 49(7):669-74 (1997).

Gao et al. Controlled release of a contraceptive steroid from biodegradable and injectable gel formulations: in vitro evaluation. Pharm Res. 12(6):857-63 (1995).

Gebremariam et al. APX001 Is Effective in the Treatment of Murine Invasive Pulmonary Aspergillosis. Antimicrob Agents Chemother 63(2):e01713-18 (2019).

Gebremariam et al. Galactomannan Is a Biomarker of Fosmanogepix (APX001) Efficacy in Treating Experimental Invasive Pulmonary Aspergillosis. Antimicrob Agents Chemother 64(1):e01966-19 (2019).

Hager et al. In Vitro and In Vivo Evaluation of the Antifungal Activity of APX001A/APX001 against Candida auris. Antimicrob Agents Chemother 62(3):e02319-17 (2018).

Hata et al. Efficacy of Oral E1210, a New Broad-Spectrum Antifungal with a Novel Mechanism of Action, in Murine Models of Candidiasis, Aspergillosis, and Fusariosis. Antimicrob Agents Chemother 55(1):4543-4551 (2011).

Kapoor et al. Evaluation of Resistance Development to the Gwt1 Inhibitor Manogepix (APX001A) in Candida Species. Antimicrob Agents Chemother 64(1):e01387-19 (2019).

Mcguigan et al. Application of phosphoramidate pronucleotide technology to abacavir leads to a significant enhancement of antiviral potency. J. Med. Chem. 48:3504-3515 (2005).

Miyazaki et al. In Vitro Activity of E1210, a Novel Antifungal, against Clinically Important Yeasts and Molds. Antimicrob Agents Chemother 55(10):4652-4658 (2011).

Ostro et al. Use of Liposomes as Injectable-Drug Delivery Systems. Am J Hosp Pharm 46(8):1576-1587 (Aug. 1989).

PCT/US2018/064609 Invitation to Pay Additional Fees dated Jan. 16, 2019.

PCT/US2018/064609 International Search Report and Written Opinion dated Mar. 14, 2019.

PCT/US2019/038780 International Search Report and Written Opinion dated Nov. 21, 2019.

PCT/US2019/038780 Invitation to Pay Additional Fees dated Sep. 23, 2019.

PCT/US2020/036400 International Search Report and Written Opinion dated Sep. 23, 2020.

Pfaller et al. In Vitro Activity of a Novel Broad-Spectrum Antifungal, E1210, Tested against *Aspergillus* spp. Determined by CLSI and EUCAST Broth Microdilution Methods. Antimicrob Agents Chemother 55(11):5155-8 (2011).

Pfaller et al. In Vitro Activity of APX001A (Manogepix) and Comparator Agents against 1,706 Fungal Isolates Collected during an International Surveillance Program in 2017. Antimicrob Agents Chemother 63(8):e00840-19 (2019).

PubChem CID 68452548 Entry for [3-[3-[[4-(Pyridin-2-yloxymethyl)phenyl]methyl]-1,2-oxazol-5-yl]pyridin-2-yl]carbamic acid; https://pubchem.ncbi.nlm.nih.gov/compound/68452548 Entry created Nov. 30, 2012.

Rao. Recent developments of collagen-based materials for medical applications and drug delivery systems. J Biomater Sci Polym Ed. 7(7):623-45 (1995).

Rivero-Menendez et al. In vitro activity of APX001A against rare moulds using EUCAST and CLSI methodologies. J Antimicrob Chemother 74(5):1295-1299 (2019).

Shaw et al. Fosmanogepix: A Review of the First-in-Class Broad Spectrum Agent for the Treatment of Invasive Fungal Infections. J Fungi (Basel) 6(4):239 (2020).

Shaw et al. In Vitro and In Vivo Evaluation of APX001A/APX001 and Other Gwt1 Inhibitors against Cryptococcus. Antimicrob Agents Chemother 62(8):e00523-18 (2018).

Silverman. Chapter 8: Prodrugs and Drug Delivery Systems. The Organic Chemistry of Drug Design and Drug Action, Academic Press, Inc., San Diego (pp. 352-401) (1992).

Thomas et al. Synthesis and biological evaluation of glucuronide prodrugs of the histone deacetylase inhibitor CI-994 for application in selective cancer chemotherapy. Bioorg. Med. Chem. 16:8109-16 (2008).

Trzoss et al. Synthesis of analogs of the Gwt1 inhibitor manogepix (APX001A) and in vitro evaluation against *Cryptococcus* spp. Bioorg Med Chem Lett 29(23):126713 (2019).

Viriyakosol et al. APX001 and Other Gwt1 Inhibitor Prodrugs Are Effective in Experimental Coccidioides immitis Pneumonia. Antimicrob Agents Chemother 63(2):e01715-18 (2019).

Watanabe et al. E1210, a new broad-spectrum antifungal, suppresses Candida albicans hyphal growth through inhibition of glycosylphosphatidylinositol biosynthesis. Antimicrob Agents Chemother 56(2):960-971 (2012).

Wiederhold et al. Efficacy of Delayed Therapy with Fosmanogepix (APX001) in a Murine Model of Candida auris Invasive Candidiasis. Antimicrob Agents Chemother 63(11):e01120-19 (2019).

Wiederhold et al. The Investigational Agent E1210 Is Effective in Treatment of Experimental Invasive Candidiasis Caused by Resistant Candida albicans. Antimicrob Agents Chemother 59(1):690-692 (2015).

Zhao et al. APX001 Pharmacokinetic/Pharmacodynamic Target Determination against Aspergillus fumigatus in an In Vivo Model of Invasive Pulmonary Aspergillosis. Antimicrob Agents Chemother 63(4):e02372-18 (2019).

(56) References Cited

OTHER PUBLICATIONS

Zhao et al. In Vivo Pharmacokinetics and Pharmacodynamics of APX001 against *Candida* spp. in a Neutropenic Disseminated Candidiasis Mouse Model. Antimicrob Agents Chemother 62(4):e02542-17 (2018).

Zhao et al. Significantly Improved Pharmacokinetics Enhances In Vivo Efficacy of APX001 against Echinocandin- and Multidrug-Resistant Candida Isolates in a Mouse Model of Invasive Candidiasis. Antimicrob Agents Chemother 62(10):e00425-18 (2018).

* cited by examiner

PYRIDINE DERIVATIVES SUBSTITUTED BY HETEROCYCLIC RING AND AMINO GROUP

CROSS-REFERENCE

This application is the National Stage Entry of International Application No. PCT/US2019/038780, filed Jun. 24, 2019, which claims the benefit of U.S. Provisional Application No. 62/689,535, filed Jun. 25, 2018, and U.S. Provisional Application No. 62/722,539, filed Aug. 24, 2018; the disclosure of each of the prior applications is considered part of and is incorporated by reference in the disclosure of this application.

BACKGROUND

Management of opportunistic infections has remained an ongoing challenge due to chemotherapy-induced immunodeficiency and an increasing elderly population.

BRIEF SUMMARY OF THE INVENTION

In an aspect, provided herein is a compound having structural Formula (II), or a pharmaceutically acceptable salt, solvate, tautomer, or stereoisomer thereof:

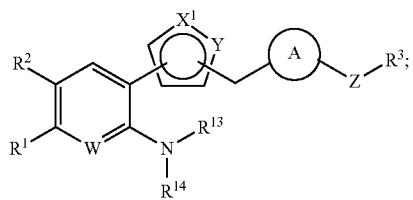

(II)

wherein:
one of $X^1$ and Y is nitrogen while the other is nitrogen or oxygen;
W is N or $N^+$—$R^{15}$;
A is substituted or unsubstituted phenyl or substituted or unsubstituted pyridinyl;
Z is a bond, —$(CH_2)_{z1}$—, —O—, —S—, —$CH_2O$—, —$OCH_2$—, —NH—, —$CH_2NH$—, —$NHCH_2$—, —$CH_2S$— or —$SCH_2$—;
z1 is 1 or 2;
$R^1$ is hydrogen, halogen, —$NR^{1B}R^{1C}$, —$C(O)NR^{1B}R^{1C}$, —$OR^{1A}$, substituted or unsubstituted alkyl, or substituted or unsubstituted heteroalkyl;
$R^2$ is hydrogen or halogen;
$R^3$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{13}$ is —$SO_{n13}R^{13A}$, —$SO_{v13}NR^{13B}R^{13C}$, —$C(O)R^{13D}$, —$C(S)R^{13D}$, —$C(O)X^2R^{13C}$, —$C(S)OR^{13D}$, —$C(S)NR^{13B}R^{13C}$, substituted alkyl, substituted or unsubstituted heteroalkyl; or $R^{13}$ together with the nitrogen to which it is attached forms an amino acid, a dipeptide, or a tripeptide;
$X^2$ is —O—, —S—, or —$NR^{13B}$;
$R^{14}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{15}$ is —$SO_{n15}R^{15A}$, —$SO_{v15}NR^{15B}R^{15C}$, —$C(O)R^{15D}$, —$C(S)R^{15D}$, —$C(O)OR^{15D}$, —$C(S)OR^{15D}$, —$C(O)SR^{15D}$, —$C(O)NR^{15B}R^{15C}$, —$C(S)NR^{15B}R^{15C}$, —$CH_2OPO_3H_2$, —$CH_2OSO_3H$, —$CH_2OPO_3H^-$, —$CH_2OSO_3^-$, —$C(O)CH_2X^3$, or substituted or unsubstituted heteroalkyl;
$X^3$ is —F, —Cl, —Br, —I, —$CHF_2$, —$CHCl_2$, —$CHBr_2$, —$CHI_2$, —$CF_3$, —$CCl_3$, —$CBr_3$, —$CI_3$, or —$NO_2$;
n13 and n15 are independently an integer from 0 to 4;
v13 and v15 are independently 1 or 2; and
$R^{1A}$, $R^{1B}$, $R^{1C}$, $R^{13A}$, $R^{13B}$, $R^{13C}$, $R^{13D}$, $R^{15A}$, $R^{15B}$, $R^{15C}$, and $R^{15D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{13B}$ and $R^{13C}$ or $R^{15B}$ and $R^{15C}$ substituents bonded to the same nitrogen atom may optionally be joined to form a substituted or unsubstituted heterocycloalkyl or substituted or unsubstituted heteroaryl.

In some embodiments, W is $N^+$—$R^{15}$.

In some embodiments, $R^{15}$ is substituted or unsubstituted heteroalkyl. In some embodiments, $R^{15}$ is —$CH_2OPO_3H_2$, —$CH_2OPO_3H^-$, —$CH_2OSO_3H$, or —$CH_2OSO_3^-$. In some embodiments, $R^{15}$ is —$C(O)CH_2X^3$.

In some embodiments, $R^{15}$ is

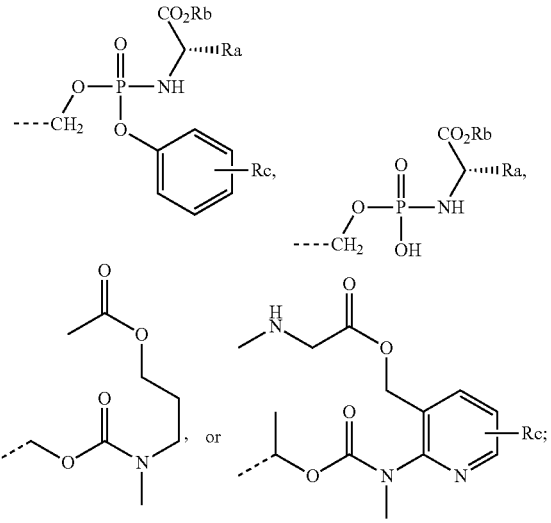

Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain of a natural amino acid; and Rb and Rc are independently hydrogen, halogen, hydroxy, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, W is N.

In some embodiments, $R^{13}$ is —C(O)$R^{13D}$ or —C(O)$X^2R^{13C}$.

In some embodiments:
$R^{13}$ is —C(O)$X^2R^{13C}$;
$X^2$ is —O—; and
$R^{13C}$ is substituted or unsubstituted phenyl.

In some embodiments, the compound has structural Formula (I):

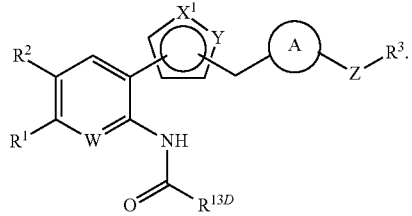

(I)

In some embodiments, $R^{13D}$ is substituted alkyl, substituted or unsubstituted heteroalkyl, or substituted or unsubstituted heterocycloalkyl. In some embodiments, $R^{13D}$ is —CH$_2$Cl.

In some embodiments, $R^{13D}$ is —SCH$_3$, —OCH$_2$CH$_3$, —SCH$_2$CH$_3$,

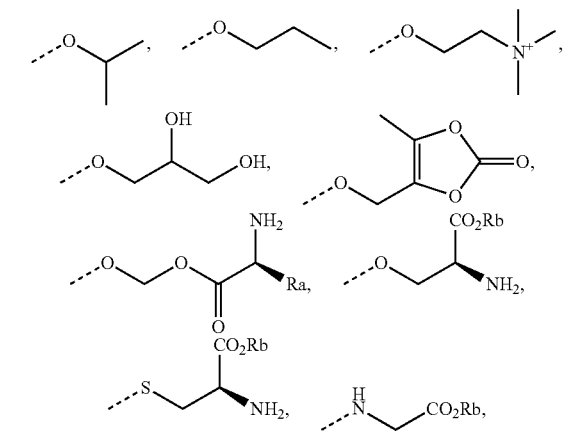

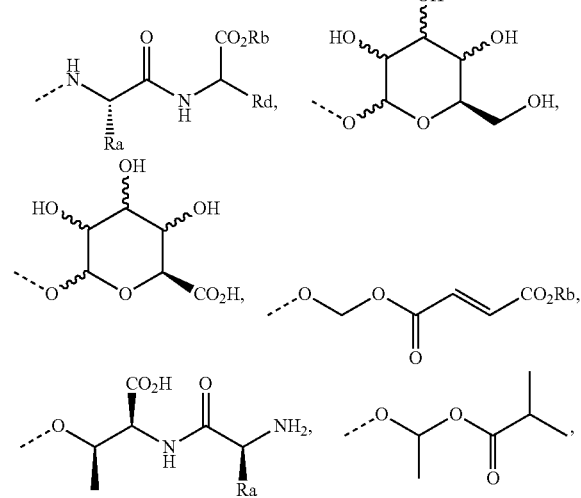

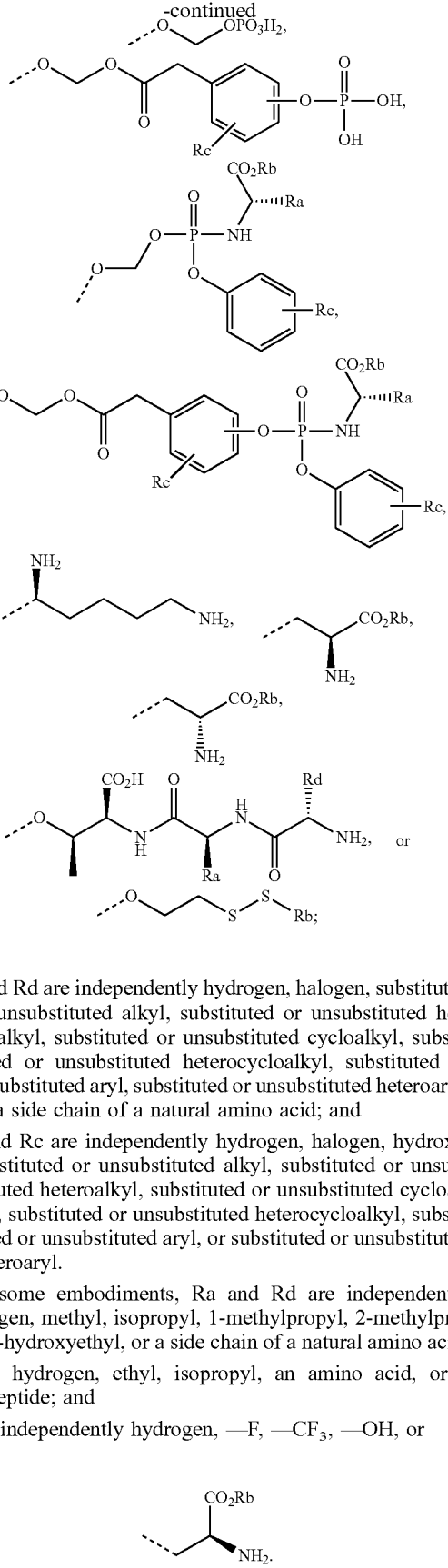

Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain of a natural amino acid; and Rb and Rc are independently hydrogen, halogen, hydroxy, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, Ra and Rd are independently hydrogen, methyl, isopropyl, 1-methylpropyl, 2-methylpropyl, 1-hydroxyethyl, or a side chain of a natural amino acid;

Rb is hydrogen, ethyl, isopropyl, an amino acid, or a dipeptide; and

Rc is independently hydrogen, —F, —CF$_3$, —OH, or

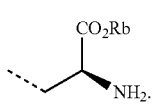

In some embodiments, $R^{13D}$ is:

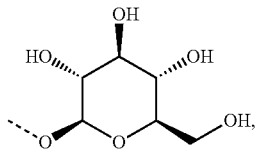 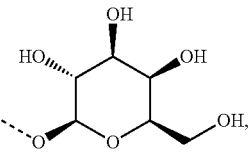

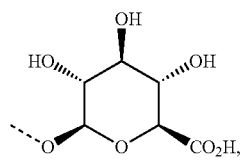 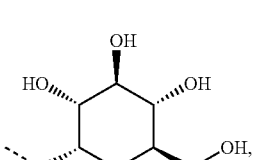

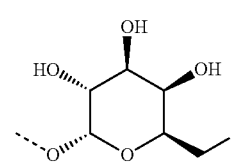 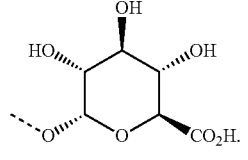

In some embodiments, $R^{13D}$ is:

  

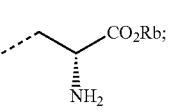

wherein:
Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^{13D}$ is:

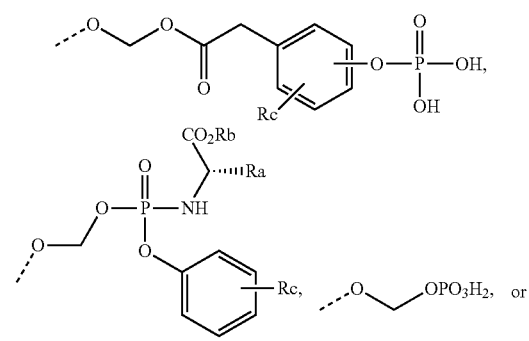

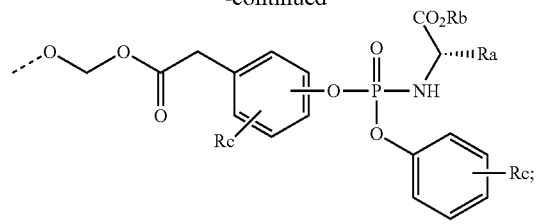

and
wherein:
Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and
Rb and Rc are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^{13D}$ is:

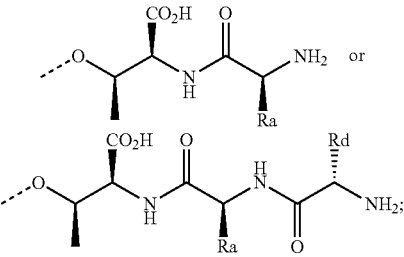

wherein:
Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid.

In some embodiments, $R^{13D}$ is —SCH$_3$, —OCH$_2$CH$_3$, —SCH$_2$CH$_3$,

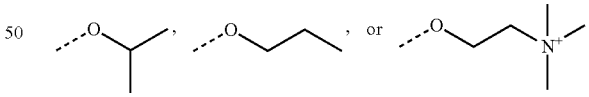

In some embodiments, $R^{13D}$ is:

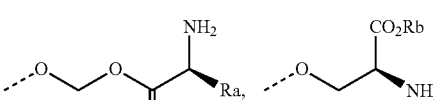

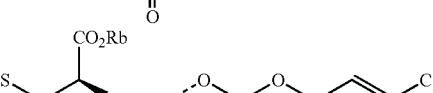

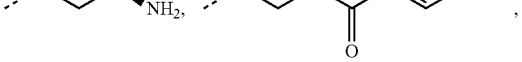

-continued

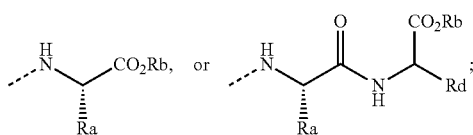

wherein:

Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^{13}$ together with the nitrogen to which it is attached forms an amino acid, a dipeptide, or a tripeptide.

In some embodiments, $R^{13}$ is:

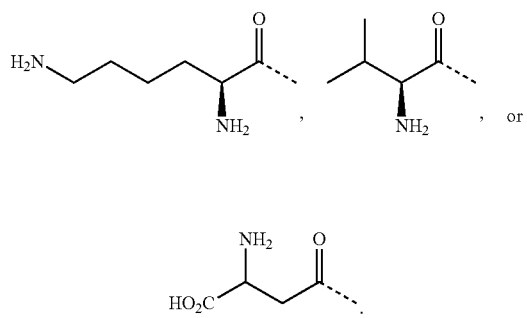

In some embodiments, one of $X^1$ and Y is a nitrogen atom and the other is an oxygen atom.

In some embodiments, a partial structure represented by

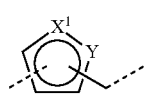

in Formulas (I), (Ib), and/or (II) is

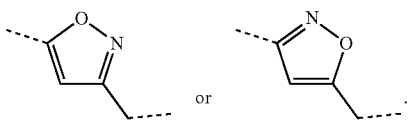

In some embodiments, Z is —O—, —CH$_2$O—, or —OCH$_2$—.

In some embodiments, $R^3$ is unsubstituted pyridine.

In some embodiments, A is unsubstituted phenyl.

In some embodiments, $R^1$ and $R^2$ are hydrogen.

In some embodiments, the compound has structural Formula (Ia):

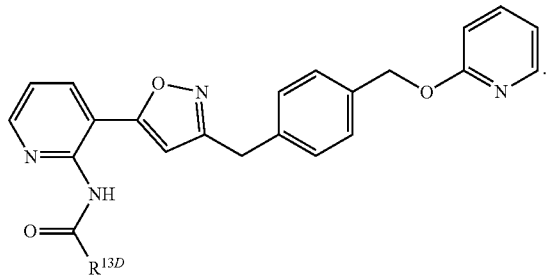

In some embodiments, $R^{13}$ is —C(O)X$^2$R$^{13C}$.

In some embodiments, the compound has structural Formula (Ib):

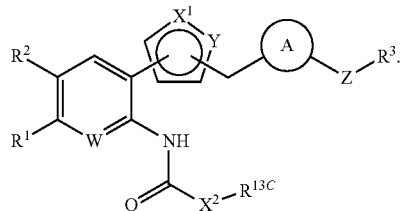

In some embodiments, $R^{13C}$ is hydrogen, substituted or unsubstituted alkyl, substituted or unsubstituted aryl, or substituted or unsubstituted heteroalkyl.

In some embodiments, a partial structure represented by

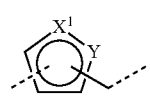

in Formulas (I), (Ib), and/or (II) is

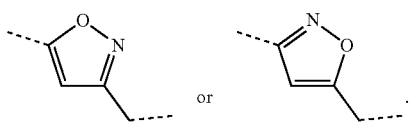

In some embodiments, Z is —O—, —CH$_2$O—, or —OCH$_2$—.

In some embodiments, $R^3$ is unsubstituted pyridine.

In some embodiments, A is unsubstituted phenyl.

In some embodiments, $R^1$ and $R^2$ are hydrogen.

In some embodiments, the compound has structural Formula (Ibb):

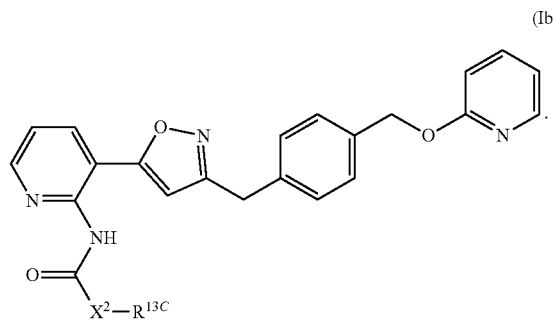

(Ibb)

In another aspect, provided herein is a pharmaceutical composition, including a compound as described herein having structural Formula (I), (Ia), (Ib), (Ibb), or (II), including embodiments, or a pharmaceutically acceptable salt, solvate, tautomer, or stereoisomer thereof, and at least one pharmaceutically acceptable carrier.

In another aspect, provided herein is a method of treating a fungal disease or infection, comprising administering to a subject in need thereof a therapeutically effective amount of a compound as described herein having structural Formula (I), (Ia), (Ib), (Ibb), or (II), including embodiments, or a pharmaceutically acceptable salt, solvate, tautomer, or stereoisomer thereof. In some embodiments, the fungal disease or infection is caused by a *Cryptococcus, Aspergillus, Candida, Fusarium*, or *Scedosporium* fungus or a fungus from the Mucorales order. In some embodiments, the fungal disease or infection is azole-resistant and/or echinocandin-resistant.

In some embodiments, the method further comprises administering at least one antifungal agent in combination with the compound of Formula (I), (Ia), (Ib), (Ibb), or (II), including embodiments, or a pharmaceutically acceptable salt, solvate, tautomer, or stereoisomer thereof. In some embodiments, the at least one antifungal agent is an azole, an echinocandin, amphotericin B deoxycholate, amphotericin B cochleate, 5-fluorocytosine, terbinafine, griseofulvin, VL-2397, ibrexafungerp, orotomide F901318, or combinations thereof. In some embodiments, the azole is ketoconazole, fluconazole, posaconazole, itraconazole, voriconazole, isavuconazole, or miconazole. In some embodiments, the echinocandin is caspofungin, anidulafimgin, micafungin, or rezafimgin.

In some embodiments, the compound of Formula (I), (Ia), (Ib), (Ibb), or (II), including embodiments, or a pharmaceutically acceptable salt, solvate, tautomer, or stereoisomer thereof, and the antifungal agent are administered simultaneously, approximately simultaneously, or sequentially, in any order. In some embodiments, the compound of Formula (I), (Ia), (Ib), (Ibb), or (II), including embodiments, or a pharmaceutically acceptable salt, solvate, tautomer, or stereoisomer thereof, and the antifungal agent are administered simultaneously or approximately simultaneously. In some embodiments, the compound of Formula (I), (Ia), (Ib), (Ibb), or (II), including embodiments, or a pharmaceutically acceptable salt, solvate, tautomer, or stereoisomer thereof, and the antifungal agent are administered sequentially. In some embodiments, the compound of Formula (I), (Ia), (Ib), (Ibb), or (II), including embodiments, or a pharmaceutically acceptable salt, solvate, tautomer, or stereoisomer thereof, is administered before the at least one antifungal agent. In some embodiments, the compound of Formula (I), (Ia), (Ib), (Ibb), or (II), including embodiments, or a pharmaceutically acceptable salt, solvate, tautomer, or stereoisomer thereof, is administered after the at least one antifungal agent.

In some embodiments, the subject has reduced colony counts of fungi in the lungs after administration of the pharmaceutical composition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

The incidence of fungal infections has increased over the last few decades, in part due to an increase in individuals that are immunocompromised. Immunocompromised individuals include, for example, elderly individuals, individuals with HIV/AIDS, and individuals undergoing chemotherapy treatment or immunosuppressive therapy after a transplant.

Current antifungal therapies exploit differences between mammalian cells and fungal cells to kill the fungi. However, because fungi and mammals are both eukaryotes, many antifungal therapies cause side effects in the host mammal. Additionally, many fungal organisms have developed resistance to front line antifungal treatments.

In some cases, active antifungal compounds need improvements in, for example, safety, drug-drug interactions, bioavailability, acceptability (such as by masking or reducing unpleasant characteristics, such as bitter taste or gastrointestinal irritability), solubility (such as for intravenous or oral administration), prolonged or sustained release or delivery, ease of formulation, site-specific delivery of the active antifungal compounds, or activity against resistant fungal organisms. Thus, there exists a need for new compositions and methods for treating fungal diseases, and the application of prodrug strategies to improve or alter properties of the active antifungal compounds presents a possible strategy to achieve this goal.

I. DEFINITIONS

The abbreviations used herein have their conventional meanings within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen atom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P) A heteroalkyl moiety may include five optionally different heteroatoms (e.g., O, N, S, Si, or P) A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. A 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〜〜〜" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In some embodiments, the alkylarylene group has the formula:

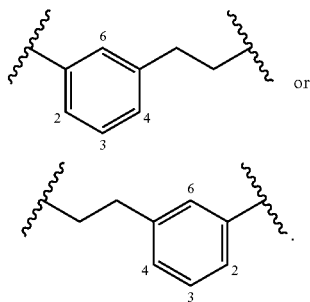

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —Cl$_3$, —CN, —CHO, —OH, —NH$_2$, —COOH, —CONH$_2$, —NO$_2$, —SH, —SO$_2$CH$_3$ —SO$_3$H, —OSO$_3$H, —SO$_2$NH$_2$, —NHNH$_2$, —ONH$_2$, —NHC(O)NHNH$_2$, substituted or unsubstituted C$_4$-C$_5$ alkyl or substituted or unsubstituted 2 to 5 membered heteroalkyl). In some embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R$^1$ and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B— wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC (O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_4$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_4$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_4$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen with a deuterium or tritium, or the replacement of a carbon with $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog" or "analogue" is used in accordance with its plain ordinary meaning within Chemistry and Biology and refers to a chemical compound that is structurally similar to another compound (i.e., a so-called "reference" compound), but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein, means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In some embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be stable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge el al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methane sulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In some embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of a compound to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's solution, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "inhibit," "block," "suppress," and grammatical variants thereof are used interchangeably herein and refer to any statistically significant decrease in biological activity, including full blocking of the activity. In some embodiments, "inhibition" refers to a decrease of about 10%, about 20%, about 30%, about 40%, about 50%, about 60%, about 70%, about 80%, about 90% or about 100% in biological activity.

As used herein in claims, drawings and the description, the symbol "----" as in "----R" indicates that the R group is a radical or partial structure that bonds to another chemical entity through a covalent chemical bond represented by ----.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

The terms "disease" or "condition" refer to a state of being or health status of a patient or subject capable of being treated with the compounds or methods provided herein. The disease may be a fungal infection. In some further instances, "fungal infection or disease" refers to human fungal infections or diseases, including a *Cryptococcus, Aspergillus, Candida, Fusarium,* or *Scedosporium* fungal disease or infection or a fungal disease or infection caused by a fungus from the Mucorales order.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., itching, swelling, burning, cough, fever, chest pain, difficulty breathing), fully or partially remove the disease's underlying cause, shorten a disease's duration, or do a combination of these things."

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In some embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, horses, rats, mice, dogs, cats, monkeys, goat, sheep, cows, deer, and other non-mammalian animals including, but not limited to, fish and birds. In some embodiments, a patient is human.

Treatment, as referred to herein, also refers to the systemic delivery of the compounds disclosed herein to any type of plant, including trees, shrubs, flowering plants, foliage plants, house plants, groundcover and grass, and agronomic plants (including crops of agronomic plants).

As used herein, the term "agronomic plant" refers to a plant of which a part or all is, or has been, harvested or cultivated on a commercial scale, or serves as an important source of feed, food, fiber, or other chemical compounds.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The lull prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a CCR4 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, inhalational or transdermal). Parenteral administration includes, e.g., intravenous, intramuscular, intra-arteriole, intradermal, subcutaneous, intraperitoneal, intraventricular, inhalational and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

II. COMPOUNDS

Described herein are compounds of Formula (I), (Ia), (Ib), (Ibb), and/or (II), or pharmaceutically acceptable salts, solvates, or stereoisomers thereof. These compounds, and compositions comprising these compounds, are useful for the treatment of fungal diseases in humans and in animals.

In some embodiments provided herein is a compound having structural Formula (II), or a pharmaceutically acceptable salt, solvate, or stereoisomer thereof:

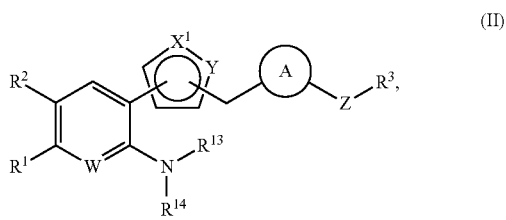

(II)

wherein:
one of $X^1$ and Y is nitrogen while the other is nitrogen or oxygen;
W is N or $N^+$—$R^{15}$;
A is substituted or unsubstituted phenyl or substituted or unsubstituted pyridinyl;
Z is a bond, —$(CH_2)_{z1}$—, —O—, —S—, —$CH_2O$—, —$OCH_2$—, —NH—, —$CH_2NH$—, —$NHCH_2$—, —$CH_2S$— or —$SCH_2$—;
z1 is 1 or 2;
$R^1$ is hydrogen, halogen, —$NR^{1B}R^{1C}$, —$C(O)NR^{1B}R^{1C}$, —$OR^{14}$, substituted or unsubstituted alkyl, or substituted or unsubstituted heteroalkyl;
$R^2$ is hydrogen or halogen;
$R^3$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{13}$ is —$SO_{n13}R^{13A}$, —$SO_{v13}NR^{13B}R^{13C}$, —$C(O)R^{13D}$, —$C(S)R^{13D}$, —$C(O)X^2R^{13C}$, —$C(S)OR^{13D}$, —$C(S)NR^{13B}R^{13C}$, substituted alkyl, substituted or unsubstituted heteroalkyl; or $R^{13}$ together with the nitrogen to which it is attached forms an amino acid, a dipeptide, or a tripeptide;

$X^2$ is —O—, —S—, or —$NR^{13B}$;
$R^{14}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{15}$ is —$SO_{n15}R^{15A}$, —$SO_{v15}NR^{15B}R^{15C}$, —$C(O)R^{15D}$, —$C(S)R^{15D}$, —$C(O)OR^{15D}$, —$C(S)OR^{15D}$, —$C(O)SR^{15D}$, —$C(O)NR^{15B}R^{15C}$, —$C(S)NR^{15B}R^{15C}$, —$CH_2OPO_3H_2$, —$CH_2OSO_3H$, —$CH_2OPO_3H^-$, —$CH_2OSO_3^-$, —$C(O)CH_2X^3$, or substituted or unsubstituted heteroalkyl;
$X^3$ is —F, —Cl, —Br, —I, —$CHF_2$, —$CHCl_2$, —$CHBr_2$, —$CHI_2$, —$CF_3$, —$CCl_3$, —$CBr_3$, —$CI_3$, or —$NO_2$;
n13 and n15 are independently an integer from 0 to 4;
v13 and v15 are independently 1 or 2; and
$R^{1A}$, $R^{1B}$, $R^{1C}$, $R^{13A}$, $R^{13B}$, $R^{13C}$, $R^{13D}$, $R^{15A}$, $R^{15B}$, $R^{15C}$, and $R^{15D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{13B}$ and $R^{13C}$ or $R^{15B}$ and $R^{15C}$ substituents bonded to the same nitrogen atom may optionally be joined to form a substituted or unsubstituted heterocycloalkyl or substituted or unsubstituted heteroaryl.

In some embodiments, the compounds of structural Formula (II) have structural Formula (I), or a pharmaceutically acceptable salt, solvate, or stereoisomer thereof:

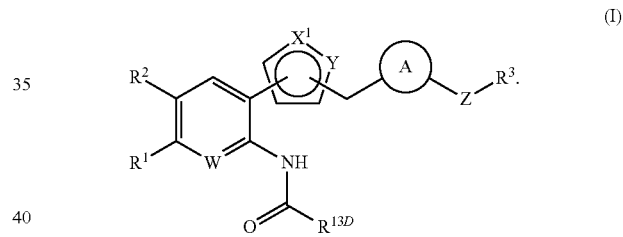

(I)

In some embodiments of compounds of Formula (I) and (II), or a tautomer or stereoisomer thereof, $R^{13}$ together with the nitrogen to which it is attached forms an amino acid, a dipeptide, or a tripeptide.

In some embodiments, the compounds of structural Formula (II) have structural Formula (Ia), or a pharmaceutically acceptable salt, solvate, or stereoisomer thereof:

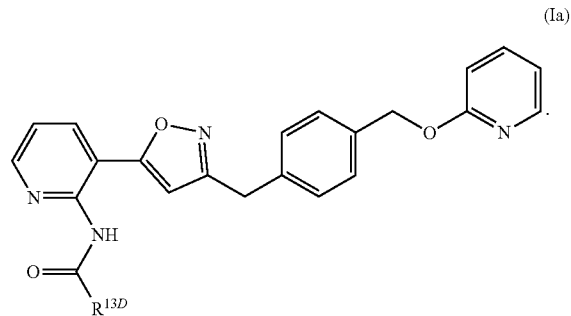

(Ia)

In some embodiments of compounds of Formula (I), (Ia), and (II), or a tautomer or stereoisomer thereof, $R^1$ and $R^2$ are hydrogen.

In some embodiments of compounds of Formula (I), (Ia), and (II), or a tautomer or stereoisomer thereof, $R^{13}$ is:

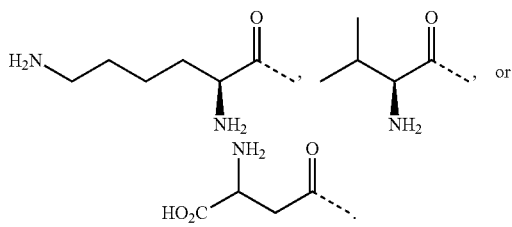

In some embodiments of compounds of Formula (I), (Ia), and (II), or a tautomer or stereoisomer thereof, $R^{13}$ is —C(O)$R^{13D}$ or —C(O)$X^2R^{13C}$.

In some embodiments of compounds of Formula (I), (Ia), and (II), or a tautomer or stereoisomer thereof:
$R^{13}$ is —C(O)$X^2R^{13C}$;
$X^2$ is —O—; and
$R^{13C}$ is substituted or unsubstituted phenyl.

In some embodiments of compounds of Formula (I), (Ia), and (II), or a tautomer or stereoisomer thereof, $R^{13D}$ is substituted alkyl, substituted or unsubstituted heteroalkyl, or substituted or unsubstituted heterocycloalkyl.

In some embodiments of compounds of Formula (I), (Ia), and (II), or a tautomer or stereoisomer thereof, $R^{13D}$ is —CH$_2$Cl.

In some embodiments of compounds of Formula (I), (Ia), and (II), or a tautomer or stereoisomer thereof, $R^{13D}$ is —SCH$_3$, —OCH$_2$CH$_3$, —SCH$_2$CH$_3$,

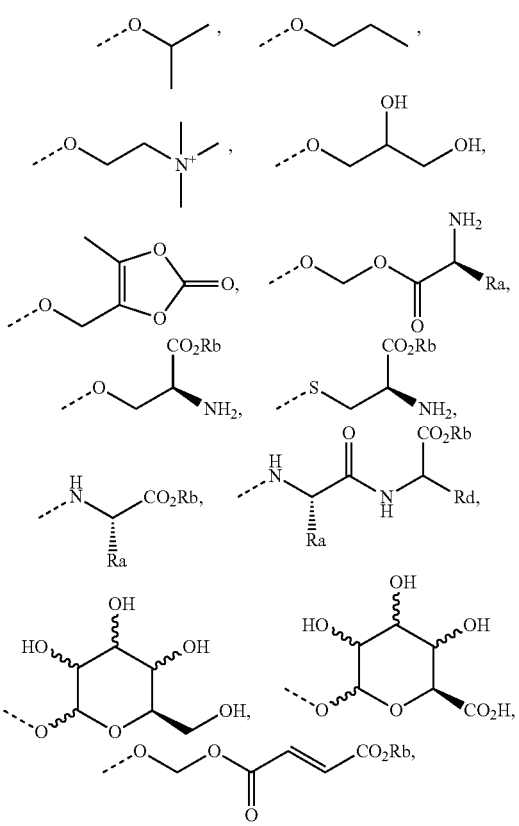

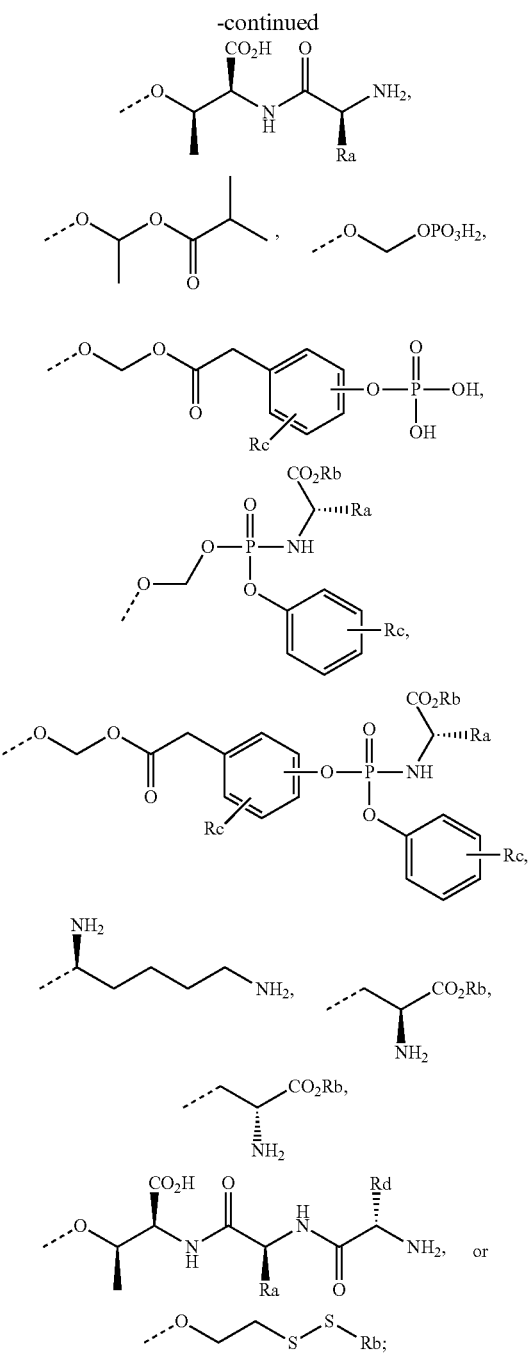

wherein:
Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and Rb and Rc are independently hydrogen, halogen, hydroxy, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments of compounds of Formula (I), (Ia), and (II), or a tautomer or stereoisomer thereof, $R^{13D}$ is:

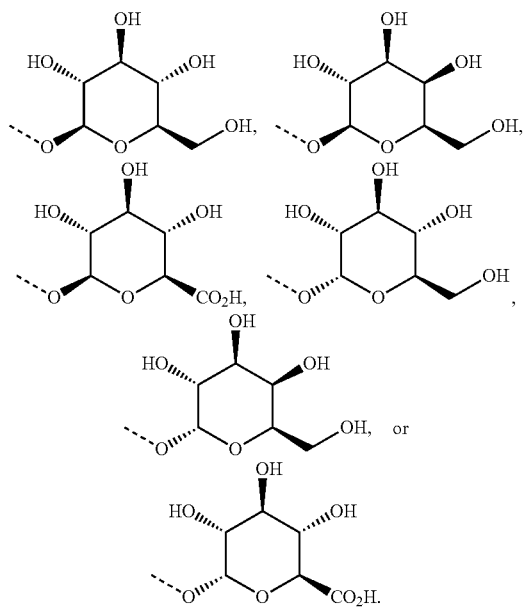

In some embodiments of compounds of Formula (I), (Ia), and (II), or a tautomer or stereoisomer thereof, $R^{13D}$ is:

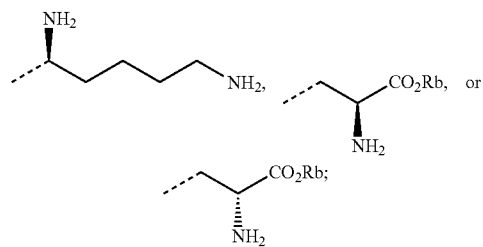

and
wherein:
Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments of compounds of Formula (I), (Ia), and (II), or a tautomer or stereoisomer thereof, $R^{13D}$ is:

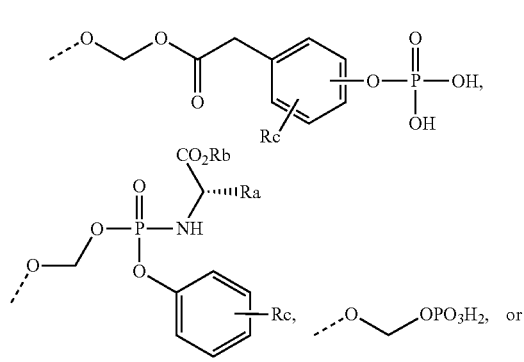

-continued

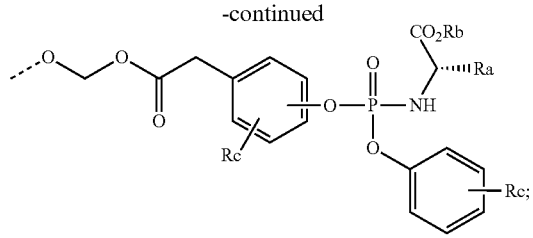

wherein:
Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and Rb and Rc are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments of compounds of Formula (I), (Ia), and (II), or a tautomer or stereoisomer thereof, $R^{13D}$ is:

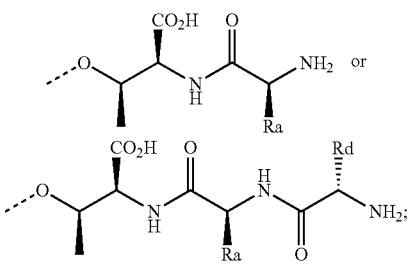

wherein:
Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid.

In some embodiments of compounds of Formula (I), (Ia), and (II), or a tautomer or stereoisomer thereof, $R^{13D}$ is $-SCH_3$, $-OCH_2CH_3$, $-SCH_2CH_3$,

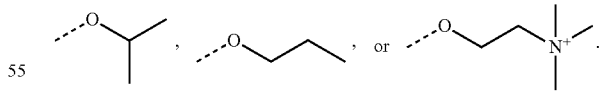

In some embodiments of compounds of Formula (I), (Ia), and (II), or a tautomer or stereoisomer thereof, $R^{13D}$ is:

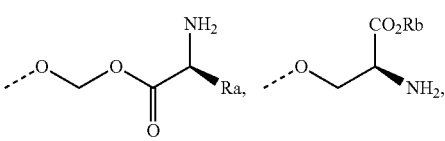

-continued

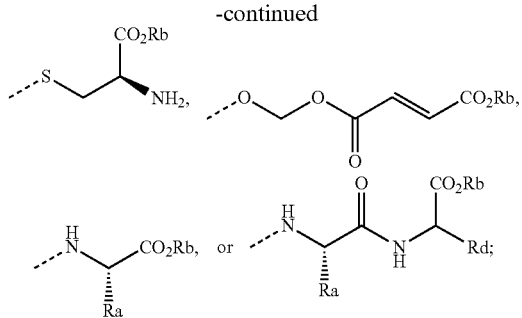

wherein:
Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and
Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments of compounds of Formula (I) and (II), $R^{13}$ is $-C(O)X^2R^{13C}$.

In some embodiments, the compounds of structural Formula (II) have structural Formula (Ib), or a pharmaceutically acceptable salt, solvate, or stereoisomer thereof:

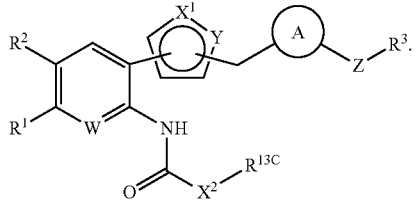

(Ib)

In some embodiments, the compounds of structural Formula (II) have structural Formula (Ibb), or a pharmaceutically acceptable salt, solvate, or stereoisomer thereof:

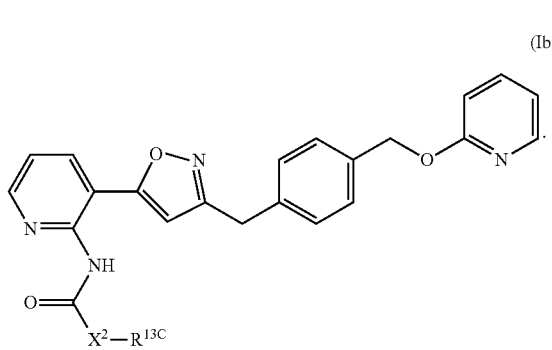

(Ibb)

In some embodiments of compounds of Formula (I), (Ib), (Ibb), and (II), or a tautomer or stereoisomer thereof, $R^{13C}$ is hydrogen, substituted or unsubstituted alkyl, substituted or unsubstituted heteroalkyl, or substituted or unsubstituted aryl.

In some embodiments of compounds of Formula (I), (Ib), and (II), or a tautomer or stereoisomer thereof, W is $N^+-R^{15}$.

In some embodiments of compounds of Formula (I), (Ib), and (II), or a tautomer or stereoisomer thereof, $R^{15}$ is substituted or unsubstituted heteroalkyl.

In some embodiments of compounds of Formula (I), (Ib), and (II), or a tautomer or stereoisomer thereof, $R^{15}$ is $-CH_2OPO_3H_2$, $-CH_2OPO_3H^-$, $-CH_2OSO_3H$, or $-CH_2OSO_3^-$.

In some embodiments of compounds of Formula (I), (Ib), and (II), or a tautomer or stereoisomer thereof, $R^{15}$ is $-C(O)CH_2X^3$.

In some embodiments of compounds of Formula (I), (Ib), and (II), or a tautomer or stereoisomer thereof, $R^{15}$ is:

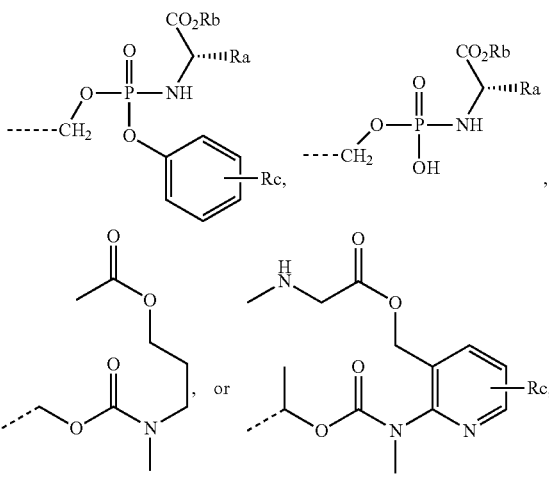

Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and
Rb and Rc are independently hydrogen, halogen, hydroxy, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments of compounds of Formula (I), (Ib), and (II), or a tautomer or stereoisomer thereof, W is N.

In some embodiments of compounds of Formula (I), (Ib), and (II), or a tautomer or stereoisomer thereof, Ra and Rd are independently hydrogen, methyl, isopropyl, 1-methylpropyl, 2-methylpropyl, 1-hydroxyethyl, or a side chain on a natural amino acid.

In some embodiments of compounds of Formula (I), (Ib), and (II), or a tautomer or stereoisomer thereof, Rb is hydrogen, ethyl, isopropyl, an amino acid, or a dipeptide.

In some embodiments of compounds of Formula (I), (Ib), and (II), or a tautomer or stereoisomer thereof, Rc is independently hydrogen, $-F$, $-CF_3$, $-OH$, or

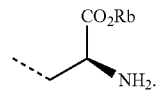

In some embodiments of compounds of Formula (I), (Ib), and (II), or a tautomer or stereoisomer thereof, one of $X^1$ and Y is a nitrogen atom and the other is an oxygen atom.

In some embodiments of compounds of Formula (I), (Ib), and/or (II), or a tautomer or stereoisomer thereof, a partial structure represented by

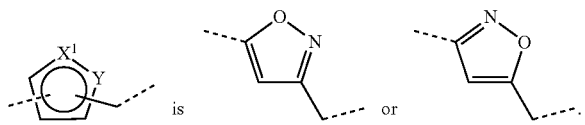

In some embodiments of compounds of Formula (I), (Ib), and (II), or a tautomer or stereoisomer thereof, Z is —O—, —CH$_2$O—, or —OCH$_2$—.

In some embodiments of compounds of Formula (I), (Ib), and (II), or a tautomer or stereoisomer thereof, $R^3$ is unsubstituted pyridine.

In some embodiments of compounds of Formula (I), (Ib), and (II), or a tautomer or stereoisomer thereof, A is unsubstituted phenyl.

Prodrugs

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H, Design of Prodrugs (1985), pp. 7-9, 21-24 (Elsevier, Amsterdam). Prodrugs are delivered through any known methods described herein, including but not limited to orally, intravenously, intraperitoneal, or other method of administration known by those skilled in the art.

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. In some embodiments, prodrugs include any group bound to a heteroatom, such as the nitrogen of a pyridine which is cleaved in vivo to form the active compound or metabolite thereof. Examples of prodrugs include, but are not limited to, acetate, formate phosphate, and benzoate derivatives of alcohol or amine functional groups in the active compounds and the like.

In some embodiments, a prodrug is a salt. In some embodiments, a prodrug is a phosphate salt. In some embodiments, a prodrug is an alkyl phosphate salt. In some embodiments, a prodrug is an alkylated heteroaromatic salt. In some embodiments, a prodrug is a pyridinium salt. In some embodiments, a prodrug is a pyridinium alkylphosphate salt. In some embodiments, a prodrug is a pyridinium methylphosphate salt. In some embodiments, a prodrug comprises an alkyl phosphate bound to a heteroatom. In some embodiments, a prodrug comprises an alkyl phosphate bound to a heteroatom of a heterocycle.

In some embodiments, a prodrug is any compound that when administered to a biological system generates a biologically active compound as a result of spontaneous chemical reaction(s), enzyme catalyzed chemical reaction(s), and/or metabolic chemical reaction(s), or a combination of each. In other embodiments, prodrugs are formed using groups attached to functionality, e.g., HO—, HS—, HOOC—, NHR—, associated with the drug or active compounds, that cleave in vivo. In some embodiments, prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated above are exemplary, not exhaustive, and other varieties of prodrugs are possible. Such prodrugs of disclosed compounds fall within this scope. In some embodiments, the compounds of the present application are prodrugs themselves and are converted into other forms, including the biologically active compound forms, when administered to a biological system.

In some embodiments, prodrugs undergo some form of a chemical transformation to produce the compound that is biologically active or is a precursor of the biologically active compound. In some cases, the prodrug is biologically active, more or less than the intended active drug itself, and serves to improve drug efficacy or safety through improved oral bioavailability, and/or pharmacodynamic half-life, etc. Prodrug forms of compounds are utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992, Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

In some embodiments, prodrugs comprise phosphorus moieties including phosphates or derivatives thereof. One such class of prodrugs is the aryl amidate (McGuigan) type. One report disclosed pharmacokinetic evaluation in the cynomolgus monkey of an aryl amidate prodrug of abacavir. (C. McGuigan et al., "Application of phosphoramidate pronucleotide technology to abacavir leads to a significant enhancement of antiviral potency," J. Med. Chem. 2005, 48, 3504-3515).

In some embodiments, phosphate prodrugs of the present application include a partial structure represented by the Formula (P1):

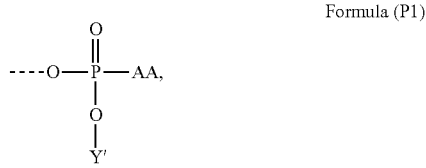

Formula (P1)

wherein AA is an amino acid, a dipeptide, or a tripeptide, and wherein Y' is H, alkyl, aryl, or heteroaryl.

In some embodiments, Y' is a $C_{1-6}$ alkyl group, unsubstituted or substituted with 1-3 groups independently selected from the group consisting of: halide, amino, —OH, —$CF_3$, $C_{1-3}$ alkyl, and $C_{1-3}$ alkoxy. In other embodiments, Y' is an aryl group, unsubstituted or substituted with 1-3 groups independently selected from the group consisting of: halide, amino, —OH, —$CF_3$, $C_{1-3}$ alkyl, and $C_{1-3}$ alkoxy. In some embodiments, Y is phenyl, unsubstituted or substituted with 1-3 groups independently selected from the group consisting of: halide, amino, —OH, —$CF_3$, $C_{1-3}$ alkyl, and $C_{1-3}$ alkoxy. In some embodiments, Y' is phenyl. In some embodiments, Y' is H.

In some embodiments, naturally-occurring or non-naturally occurring amino acids are used to prepare the compounds and or prodrugs of the present application. In some cases, amino acids suitable to be used in Formula (P1) or other functional groups (e.g., a carboxylate or amide group) as a prodrug moiety include valine, leucine, isoleucine, methionine, phenylalanine, asparagine, glutamic acid, glutamine, histidine, lysine, arginine, aspartic acid, glycine, alanine, serine, threonine, tyrosine, tryptophan, cysteine and proline. In some embodiments, L-amino acids are used. In other embodiments, D-amino acids are used. In some embodiments, both D- and L-amino acids are used. In some embodiments, an included amino acid is an alpha-, beta-, or gamma-amino acid. In some embodiments, naturally-occurring, non-standard amino acids are utilized in the compositions and methods of the present application. For example, in addition to the standard naturally occurring amino acids commonly found in proteins, naturally occurring amino acids also illustratively include 4-hydroxyproline, γ-carboxyglutamic acid, selenocysteine, desmosine, 6-N-methyllysine, 3-methylhistidine, O-phosphoserine, 5-hydroxylysine, ε-N-acetyllysine, ω-N-methylarginine, N-acetylserine, γ-aminobutyric acid, citrulline, ornithine, azaserine, homocysteine, β-cyanoalanine and S-adenosylmethionine. Non-naturally occurring amino acids include phenyl glycine, meta-tyrosine, para-amino phenylalanine, 3-(3-pyridyl)-L-alanine, 4-(trifluoromethyl)-D-phenylalanine, and the like.

In some embodiments, the amino acid covalently coupled to the phosphorus species or other functional groups (e.g., a carboxylate or amide group) is a non-polar amino acid such as valine, phenylalanine, leucine, isoleucine, glycine, alanine and methionine. In some embodiments, the dipeptide and the tripeptide comprise natural amino acids. In some embodiments, the dipeptide and the tripeptide comprise non-natural amino acids. In some embodiments, the dipeptide and the tripeptide comprise both natural and non-natural amino acids. As used herein, the "side chains" of natural amino acids refer to the R group of the 20 natural amino acids in the following general generic structure:

In some embodiments, more than one amino acid is covalently coupled to the phosphorus species or other functional groups (e.g., a carboxylate or amide group). In some embodiments, a first and second amino acid are each covalently coupled to separate sites on the functional groups (e.g., phosphate, carboxylate or amide groups) on the compounds of the present application. In other embodiments, a dipeptide is covalently coupled to the functional groups (e.g., phosphate, carboxylate or amide groups) on the compounds of the present application. In still other embodiments, a tripeptide is covalently coupled to the functional groups (e.g., phosphate, carboxylate or amide groups) on the compounds of the present application.

In some embodiments, the compounds of the present application comprise a prodrug moiety that is carbamate, thiocarbamate or urea to mask an amino group on the active compound. In some embodiments, the prodrug moiety of carbamate, thiocarbamate or urea is metabolized in vivo to afford the free amino moiety on the active compound.

In some embodiments, activation of the prodrugs involves a spontaneous reaction. As used herein, the term "spontaneous reaction" regarding prodrugs generally refers to chemical reactions that do not require the presence of other reagents, e.g., a specific enzyme or another chemical entity, to complete the chemical transformation. In some embodiments, the starting material in a spontaneous reaction undergoes intramolecular reactions to produce the product. In some embodiments, the loss or diffusion of one of the products in such spontaneous reactions makes this spontaneous reaction irreversible. In some cases, the reaction rate of a spontaneous reaction is slow, e.g., half-life of the reaction is longer than a day. In some cases, the reaction rate of a spontaneous reaction is fast, e.g., half-life of the reaction is shorter than a day, 5 hrs, 1 hr, or half an hour. In some embodiments, the spontaneous reaction is a cyclization reaction. In some embodiments, the cyclization reaction is between a newly formed nucleophilic entity (e.g., —OH, —$NH_2$, —NHR, —SH, etc.) and an existing electrophilic entity (e.g., ester, carbamate, thiocarbamate, urea, formaldehyde derivative, etc.). In some embodiments, the cyclization reaction forms a 5- or 6-membered ring as a by-product. Scheme 1 shows one example of a spontaneous reaction of prodrugs.

Scheme 1. After the acetate functional group is hydrolyzed by an esterase, the free OH group is nucleophilic and attacks a nearby electrophilic carbamate group to form a 6-membered cyclic carbamate, formaldehyde, and the active compound comprising an 2-aminopyridine group. The second reaction is spontaneous, i.e., without the help of another reagent or enzyme. The second reaction involves an intramolecular reaction and forms two by-products that are potentially diffusible.

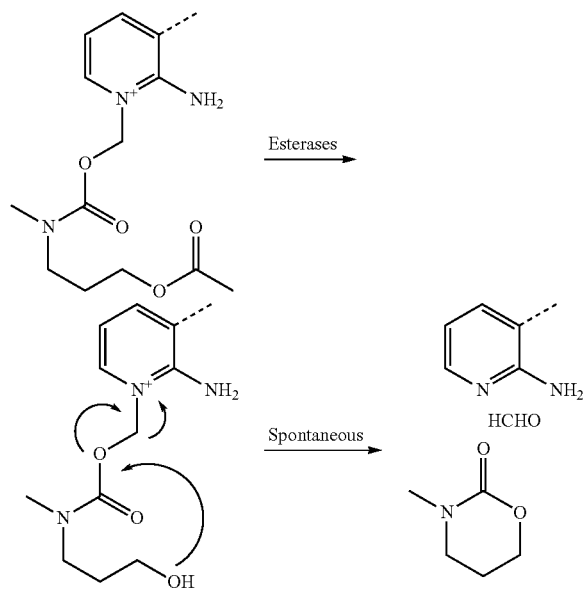

In some embodiments, enzyme-catalyzed reaction triggers the formation of the active compounds. Scheme 2 below depicts one of such an example:

Scheme 2. In some cases, the phosphoramidate prodrug is hydrolyzed by phosphoramidase directly with the ester group intact on the amino acid moiety of the prodrug. In other cases, the phosphoramidate is first hydrolyzed by esterases to break the ester group on the amino acid moiety. Then either phosphoramidase or other enzymatic processes hydrolyze the phosphoramidate to afford the phosphate monoester moiety. In some embodiments, the phosphate monoester moiety continues to react further because it is, in some cases, a prodrug as well.

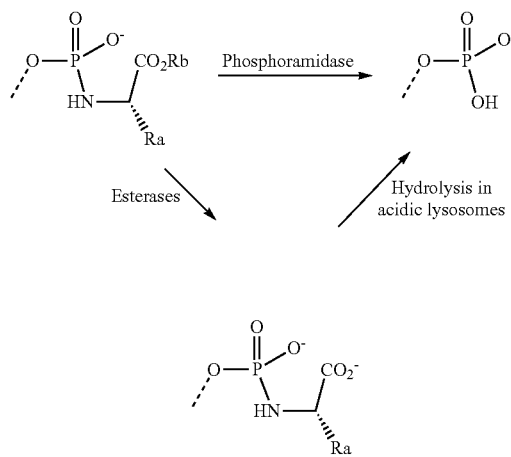

In some embodiments, activation of the prodrugs involves multiple enzymatic processes and a spontaneous reaction. Scheme 3 shows one example of a spontaneous reaction of prodrugs with the help of several enzymes.

Scheme 3. In some embodiments, the phosphate moiety adopts a prodrug form that comprises a monoamidate with an amino acid and a monoester with a phenyl-based group. After the prodrug enters the blood stream, in some cases, lysosomal carboxypeptidase cathepsin A is the hydrolase that catalyzes the hydrolysis of the ester group on the amino acid portion. Lysosomal carboxypeptidase cathepsin A is a ubiquitously expressed enzyme and is found in high levels in lymphoid cells. The released carboxylate spontaneous reaction forms a 5-memebered phosphorus-containing ring system comprising an amino acid. Ring opening is feasible via enzymatic pathways and/or chemical pathways, e.g., hydrolysis at either the phosphorus center or the ester center to break the P—O bond or the C—O in the ring. After ring opening, the amino acid moiety is released by further lydrolysis, e.g., by phosphamidase in acidic lysosomes, or by chemical reaction. The phosphate monoester is thus formed.

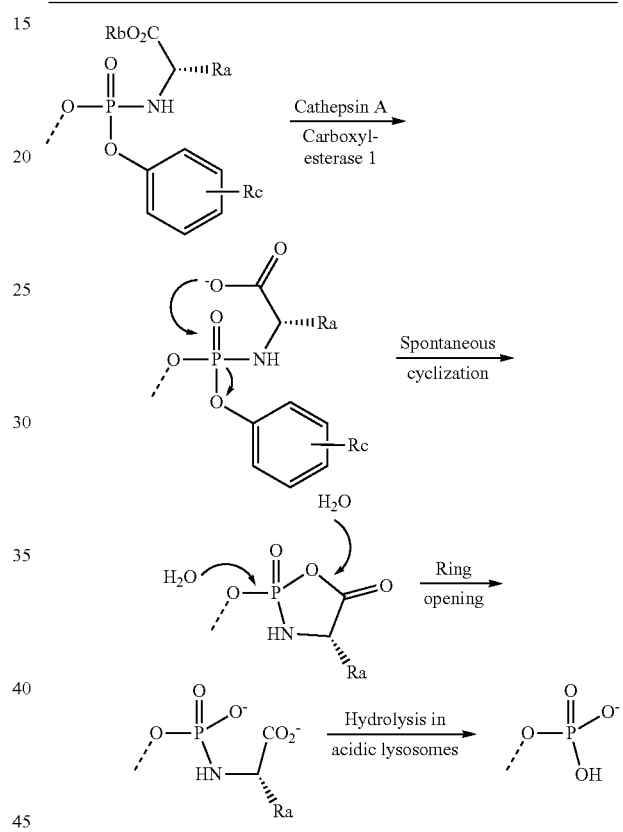

In some embodiments, glycosyl carbamates (as shown in Formula (SI)) are used as prodrugs to mask an amino group in the active compound.

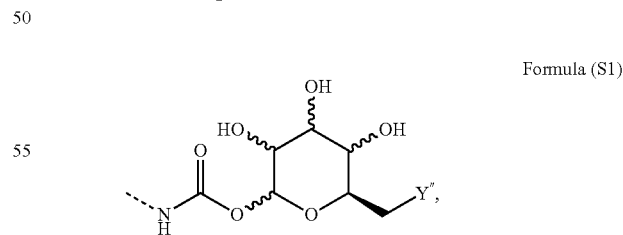

Formula (S1)

wherein Y" is OH or $CO_2H$. The carbohydrate portion of the glycosyl carbamates can be a natural or unnatural hexose or its derivatives. In some embodiments, the hexose is selected from the group consisting of allose, altrose, glucose, mannose, gulose, idose, galactose, and talose. In some embodiments, the hexose has D-configuration. In other embodiments, the hexose has L-configuration. In some embodiments, the hexose has D-configuration. In other embodiments, the hexose has L-configuration. In some embodiments, the hexose anomeric configuration is alpha (α). In some embodiments, the hexose anomeric configuration is beta (β). In some embodiments, the hexose anomeric configuration is both alpha and beta.

With multiple hydroxyl groups on the ring, hexose increases the aqueous solubility of organic molecules. Because hexose is a natural product, its use as a prodrug form has advantages such as non-toxicity and high hydrophilicity. For example, glucuronide prodrugs as shown in Scheme 4:

Scheme 4. A glucuronide prodrug shown in Scheme 4 comprises an N-pyridyl β-glucuronyl carbamate moiety. β-Glucuronidase in the biological system is a lysosomal enzyme that plays a role in the degradation of glucuronic acid-containing glycosaminoglycans. It has a broad substrate specificity. Accordingly, β-glucuronidase recognizes the carbmate structure in the glucuronide prodrug and enzymatically cleaves the glycosidic bond to afford, the glucuronic acid, the freed amino-pyridine, and carbon dioxide as the enzymatic reaction products.

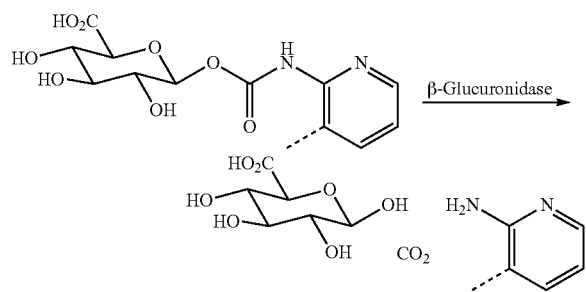

Similarly, a lysosomal enzyme such as β-galactosidase recognizes and cleaves galactoside β-prodrugs. Glucosidase is another example of enzymatic targets available for prodrug design.

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of Formula (I), (Ia), (Ib), (Ibb), and (II), or a solvate, or stereoisomer thereof, include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

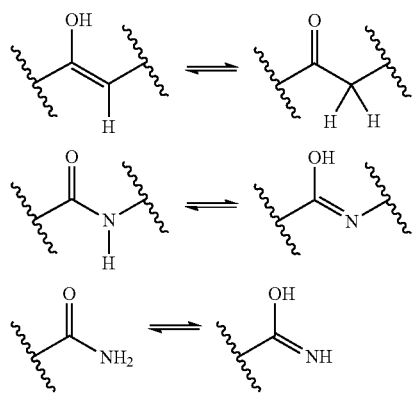

-continued

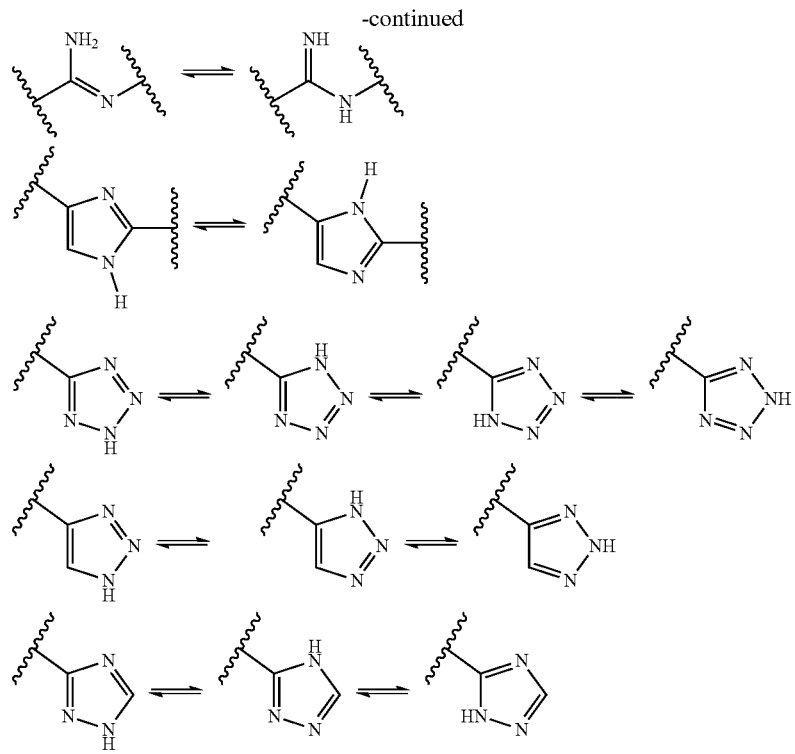

III. PHARMACEUTICAL COMPOSITIONS

In some embodiments, the compound of Formulas (I), (Ia), (Ib), or (Ibb) as described herein is administered as a pure chemical. In some embodiments, the compound of Formulas (I), (Ia), (Ib), or (Ibb) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Accordingly, provided herein is a pharmaceutical composition comprising at least one compound of Formula (I), (Ia), (Ib), (Ibb), or (II) as described herein, or a pharmaceutically acceptable salt, solvate, or stereoisomer thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound Formula (I), (Ia), (Ib), (Ibb), or (II) or a pharmaceutically acceptable salt, solvate, or stereoisomer thereof.

In some embodiments, the compound of Formula (I), (Ia), (Ib), (Ibb), or (II) provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). In some embodiments, the subject has reduced colony counts of fungi in the lungs after administration of a pharmaceutical composition comprising a compound of Formula (I), (Ia), (Ib), (Ibb), or (II). Optimal doses are generally determined using experimental models and/or clinical trials. The optimal dose depends upon the body mass, weight, sex, age, renal status, hepatic status, or blood volume of the patient.

Oral doses typically range from about 1.0 mg to about 1000 mg, one to four times, or more, per day, or one to four times per week.

IV. METHODS OF TREATMENT

Provided herein are methods for treating a fungal disease or infection in a subject in need thereof, comprising administering to the subject a therapeutically effective amount of a compound of Formula (I), (Ia), (Ib), (Ibb), or (II) at a frequency and for a duration sufficient to provide a beneficial effect to the subject. In some embodiments, the fungal disease or infection is caused by a *Cryptococcus, Aspergillus, Candida, Fusarium*, or *Scedosporium* fungus or a fungus from the Mucorales order. In some embodiments, the fungal disease or infection is azole-resistant and/or echinocandin-resistant.

Fungal Diseases

In some embodiments, the fungal disease is selected from the group consisting of aspergillosis, blastomycosis, candidiasis, coccidioidomycosis (Valley Fever), cryptococcosis, histoplasmosis, mucormycosis, *Pneumocystis* pneumonia (PCP), ringworm, sporotrichosis, and talaromycosis.

In some embodiments, the fungal disease is aspergillosis. In some embodiments, aspergillosis is allergic bronchopulmonary aspergillosis (abpa), allergic *Aspergillus* sinusitis, chronic pulmonary aspergillosis, invasive aspergillosis or cutaneous (skin) aspergillosis. In some embodiments, the subject has an aspergilloma.

In some embodiments, the fungal disease is blastomycosis.

In some embodiments, the fungal disease is candidiasis. In some embodiments, candidiasis is oropharyngeal candidiasis (thrush), vulvovaginal candidiasis (vaginal candidiasis), fungemia, or invasive candidiasis.

In some embodiments, the fungal disease is coccidioidomycosis (Valley Fever). In some embodiments, coccidioidomycosis is acute coccidioidomycosis (primary pulmonary coccidioidomycosis), chronic coccidioidomycosis, or disseminated coccidioidomycosis, including primary cutaneous coccidioidomycosis.

In some embodiments, the fungal disease is cryptococcosis. In some embodiments, cryptococcosis is wound or cutaneous cryptococcosis, pulmonary cryptococcosis, or cryptococcal meningitis.

In some embodiments, the fungal disease is a fungal eye infection. In some embodiments, the fungal eye infection is fungal keratitis, fungal exogenous endophthalmitis, or fungal endogenous endophthalmitis.

In some embodiments, the fungal disease is histoplasmosis. In some embodiments, histoplasmosis is acute histoplasmosis. In some embodiments, histoplasmosis is chronic histoplasmosis.

In some embodiments, the fungal disease is mucormycosis. In some embodiments, mucormycosis is rhinocerebral (sinus and brain) mucormycosis, pulmonary (lung) mucormycosis, gastrointestinal mucormycosis, cutaneous (skin) mucormycosis, or disseminated mucormycosis.

In some embodiments, the fungal disease is *Pneumocystis* pneumonia (PCP).

In some embodiments, the fungal disease is ringworm. In some embodiments, the ringworm is tinea pedis, tinea cruris, tinea capitis, tinea barbae, tinea manuum, tinea unguium, or tinum corporis. In some embodiments, the ringworm is caused by a type of fungi including *Trichophyton, Microsporum*, or *Epidermophyton*.

In some embodiments, the fungal disease is sporotrichosis. In some embodiments, sporotrichosis is cutaneous (skin) sporotrichosis, pulmonary (lung) sporotrichosis, or disseminated sporotrichosis.

In some embodiments, the fungal disease is talaromycosis.

In some embodiments, the fungal disease or infection is caused by a *Cryptococcus, Aspergillus, Candida, Fusarium, Scedosporium, Coccidioides, Blastomyces, Ajellomyces, Histoplasma, Rhizopus, Apophysomyces, Absidia, Saksenaea, Rhizomucor pusillus, Entomophthora, Comdiobolus, Basidiobolus, Sporothrix, Pneumocystis jirovecii, Talaromyces mameffei*, or *Asclepias* fungus/species or a fungus from the Mucorales order. In some embodiments, the fungal disease is caused by a fungal species including, but not limited to, *Aspergillus fumigatus, Aspergillus flavus, Aspergillus niger, Aspergillus terreus, Blastomyces dermatitidis, Ajellomyces dermatitidis, Candida albicans, Candida auris, Candida glabmta, Candida parapsilosis, Candida rugosa, Candida tropicalis, Coccidioides immitis, Coccidioides posadasii, Cryptococcus neoformans, Cryptocoeeus gattii, Histoplasma capsulatum, Rhizopus stolonifer, Rhizopus arrhizus, Mucor indicus, Cunninghamella bertholletiae, Apophysomyces elegans, Absidia* species, *Saksenaea* species, *Rhizomucor pusillus, Entomophthora* species, *Conidiobolus* species, *Basidiobolus* species, *Sporothrix schenckii, Pneumocystis jirovecii, Talaromyces marneffei, Asclepias albicans, Fusarium solani, Scedosporium apiospermum*, and *Rhizomucor pusillus*. In some embodiments, the fungal disease is caused by the fungal species *Aspergillus fumigatus*. In some embodiments, the fungal disease is caused by the fungal species *Candida albicans*. In some embodiments, the fungal disease is caused by the fungal species *Fusarium solani*. In some embodiments, the fungal disease is caused by the fungal species *Mucor indicus*. In some embodiments, the fungal disease is caused by the fungal species *Scedosporium apiospermum*. In some embodiments, the fungal disease is caused by the fungal species *Cryptococcus neoformans*. In some embodiments, the fungal disease is caused by the fungal species *Cryptococcus gattii*. In some embodiments, the fungal disease is caused by the fungal species *Candida auris*.

In some embodiments, a compound described herein is active against the fungal Gwt1 protein. This conserved enzyme catalyzes the glycosylphosphatidyl inositol (GPI) post-translational modification that anchors eukaryotic cell surface proteins to the cell membrane. In yeasts, GPI mediates cross-linking of cell wall mannoproteins to β-1,6-glucan. Inhibition of this enzyme in both *Candida albicans* and *Saccharomyces cerevisiae* has been shown to result in inhibition of maturation and localization of GPI-anchored mannoproteins thus demonstrating pleiotropic effects that include inhibition of fungal adherence to surfaces, inhibition of biofilm formation, inhibition of germ tube formation, severe growth defects, or lethality.

Subjects

In some embodiments, the subject is immunocompromised. In some embodiments, the subject is an immunocompromised human subject. In some embodiments, the human subject is under the age of 1 year. In some embodiments, the human subject is an infant under 1 month old. In some embodiments, the human subject is over the age of 70 years. In some embodiments, the subject is infected with HIV/AIDS. In some embodiments, the subject is undergoing or has undergone cancer chemotherapy treatment. In some embodiments, the subject is undergoing or has undergone corticosteroid treatment. In some embodiments, the subject is undergoing or has undergone TNF inhibitor treatment. In some embodiments, the subject is a transplant recipient. In some embodiments, the subject is a recipient of a hematopoietic stem-cell transplant, bone marrow transplant, lung transplant, liver transplant, heart transplant, kidney transplant, pancreas transplant or a combination thereof. In some embodiments, the subject is a recipient of a hematopoietic stem-cell transplant. In some embodiments, the subject is a recipient of a bone marrow transplant. In some embodiments, the subject is a recipient of a lung transplant. In some embodiments, the subject is a recipient of a liver transplant. In some embodiments, the subject is a recipient of a heart transplant. In some embodiments, the subject is a recipient of a kidney transplant. In some embodiments, the subject is a recipient of a pancreas transplant.

In some embodiments, the subject is a vertebrate. In some embodiments, the vertebrate is a fish, an amphibian, a reptile, a bird, a marsupial, or a mammal. In some embodiments, the subject is a fish. In some embodiments, the subject is a mammal. In some embodiments, the mammal is a human. In some embodiments, the mammal is a dog. In some embodiments, the mammal is a cat. In some embodiments, the mammal is livestock. In some embodiments, the livestock is selected from the group consisting of: cattle, sheep, goats, swine, poultry, bovine, and equine animals. In some embodiments, the subject is an invertebrate. In some embodiments, the invertebrate is an insect. In some embodiments, the subject is a plant.

V. COMBINATION THERAPY

In certain instances, the compound of Formula (I), (Ia), (Ib), (Ibb), and (II) or a pharmaceutically acceptable salt, solvate, or stereoisomer thereof, is administered in combination with a second therapeutic agent.

In some embodiments, the benefit experienced by a subject is increased by administering one of the compounds described herein with a second therapeutic agent (which also includes a therapeutic regimen) that also has therapeutic benefit.

In one specific embodiment, a compound of Formula (I), (Ia), (Ib), (Ibb), and (II) or a pharmaceutically acceptable salt, solvate, or stereoisomer thereof, is co-administered with a second therapeutic agent, wherein the compound of Formula (I), (Ia), (Ib), (Ibb), and (II) or a pharmaceutically acceptable salt, solvate, or stereoisomer thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the subject is simply additive of the two therapeutic agents or the subject experiences a synergistic benefit.

In some embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (Ia), (Ib), (Ibb), and/or (II) or a pharmaceutically acceptable salt, solvate, or stereoisomer thereof, is initiated prior to, during, or after treatment with a second agent described herein, and continues until any time during treatment with the second agent or after termination of treatment with the second agent. It also includes treatments in which a compound of Formula (I), (Ia), (Ib), (Ibb), and/or (II) or a pharmaceutically acceptable salt, solvate, or stereoisomer thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g., the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), (Ia), (Ib), (Ibb), and/or (II) or a pharmaceutically acceptable salt, solvate, or stereoisomer thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the second therapeutic agent is an antifungal agent. In some embodiments, the second therapeutic agent is an antifungal agent selected from the group consisting of: a polyene antifungal agent, an azole antifungal agent, an allylamine antifungal agent, and an echinocandin antifungal agent. In some embodiments, the antifungal agent is amphotericin B deoxycholate, amphotericin B cochleate, 5-fluorocytosine, terbinafine, griseofulvin, VL-2397, ibrexafungerp, orotomide F901318, or combinations thereof.

In some embodiments, the polyene antifungal agent is selected from the group consisting of: Amphotericin B, Candicidin, Filipin, Hamycin, Natamycin, Nystatin, and Rimocidin.

In some embodiments, the azole antifungal agent is selected from the group consisting of: an imidazole, a triazole, and athiazole. In some embodiments, the imidazole is selected from the group consisting of: bifonazole, butoconazole, clotrimazole, econazole, fenticonazole, isavuconazole, ketoconazole, luliconazole, miconazole, omoconazole, oxiconazole, sertaconazole, sulconazole, and tioconazole. In some embodiments, the triazole is selected from the group consisting of: albaconazole, efinaconazole, epoxiconazole, fluconazole, isavuconazole, itraconazole, posaconazole, propiconazole, ravuconazole, terconazole, and voriconazole. In some embodiments, the thiazole is abafungin.

In some embodiments, the allylamine antifungal agent is selected from the group consisting of: amorolfin, butenafine, naftifine, and terbinafine.

In some embodiments, the echinocandin antifungal agent is selected from the group consisting of: anidulafungin, caspofungin, micafungin and rezafungin.

In some embodiments, are methods for treating a subject with a fungal disease comprising administering to the subject a combination treatment of a compound of Formula (I), (Ia), (Ib), (Ibb), and/or (II) or a pharmaceutically acceptable salt, solvate, or stereoisomer thereof, and fluconazole, wherein the subject is selected from the group consisting of cattle, sheep, goats, swine, poultry, bovine, and equine animals.

In some embodiments, are methods for treating a subject with a fungal disease comprising administering to the subject a combination treatment of a compound of Formula (I), (Ia), (Ib), (Ibb), and/or (II) or a pharmaceutically acceptable salt, solvate, or stereoisomer thereof, and ketoconazole, wherein the subject is selected from the group consisting of cattle, sheep, goats, swine, poultry, bovine, and equine animals.

In some embodiments, are methods for treating a subject with a fungal disease comprising administering to the subject a combination treatment of a compound of Formula (I), (Ia), (Ib), (Ibb), and/or (II) or a pharmaceutically acceptable salt, solvate, or stereoisomer thereof, and itraconazole, wherein the subject is selected from the group consisting of cattle, sheep, goats, swine, poultry, bovine, and equine animals.

VI. SYNTHETIC METHODS

Method A

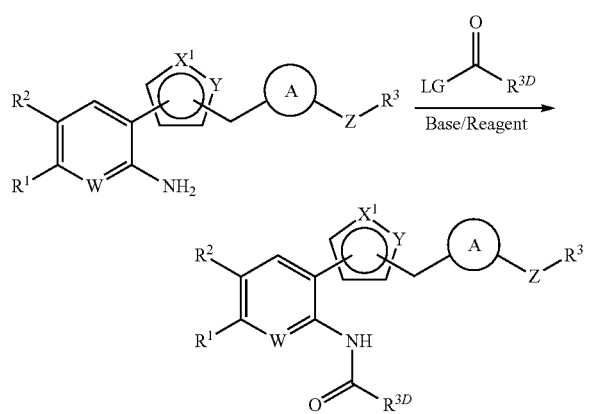

In some embodiments, as shown in Method A, an amine intermediate reacts with an acylating reagent in the presence of base and/or other reagent(s) to form a compound of Formula (I). The LG in the acylating reagent includes, but is not limited to, a leaving group, e.g., Cl and mixed anhydride, and OH. The reagent includes, but is not limited to, activation reagents, e.g., dicyclohexylcarbodiimide (DCC), (N-(3-dimethylaminopropyl)-N'-ethylcarbodiimide HCl (EDAC·HCl), 1-hydroxybenzotriazole (HOBt), 4-(N,N-dimethylamino)pyridine (DMAP), (2-(1H-benzotriazol-1-yl)-N,N,N',N'-tetramethylaminium tetrafluoroborate/hexafluorophosphate (TBTU/HBTU), (2-(7-aza-1H-benzotriazol-1-yl)-N,N,N',N'-tetramethylaminium tetrafluoroborate/hexafluorophosphate (TATU/HATU), benzotriazol-1-yloxy-tris(dimethylamino)-phosphonium hexafluorophosphate (BOP), (benzotriazol-1-yloxy-tripyrrolidino-phosphonium hexafluorophosphate (PyBOP), and bromo-tripyrrolidino-phosphonium hexafluorophosphate (PyBrOP). The base includes, but is not limited to, pyridine, di-isopropylethylamine (DIPEA), trimethylamine (TEA), and N-methyl-morpholine (NMM).

Method A1

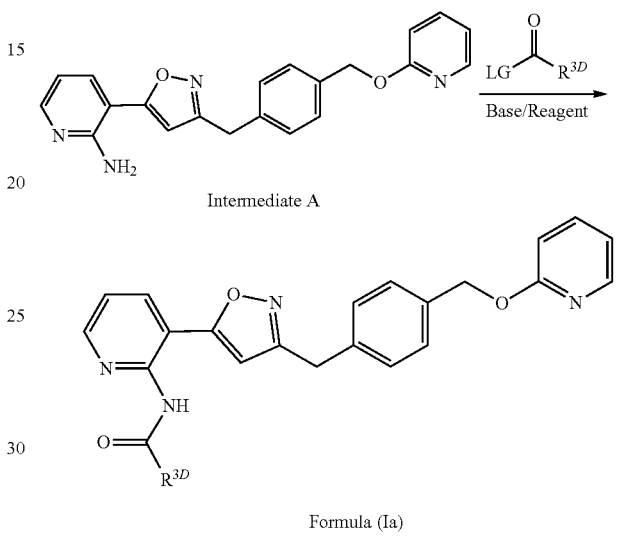

In some embodiments, as shown in Method A1, Intermediate A reacts with an acylating reagent in the presence of base and/or other reagent(s) to form a compound of Formula (Ia)

Method B

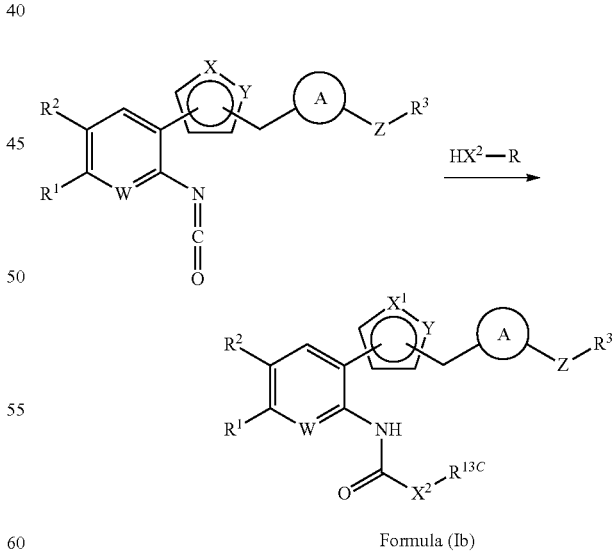

$X^2$ = O, S, or $NR^{13C}$

In some embodiments, as shown in Method B, an isocyanate intermediate reacts with a nucleophilic reagent, e.g., an alcohol, thiol or free amine to afford a compound of Formula (Ib) that comprises, a carbamate, thiocarbamate, or urea moieties. In Formula (Ib), the —R[13] moiety in Formula (I) becomes —X[2]—R[13C], wherein X[2] is O, S or NR[13B].

Method B1

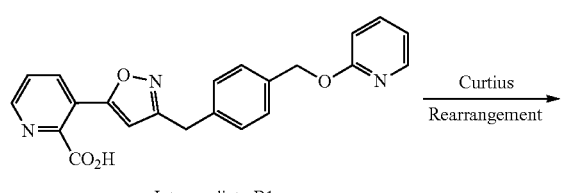

Intermediate B1

$\xrightarrow{\text{Curtius Rearrangement}}$

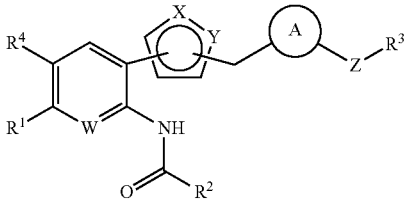

$\xrightarrow{HX^2-R}$

Intermediate B2

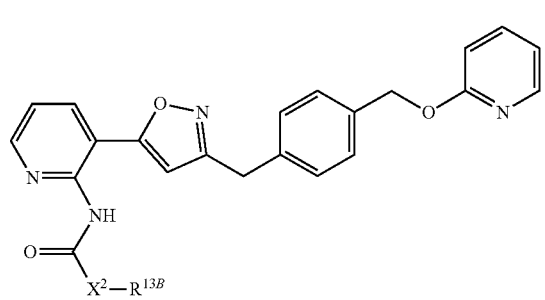

Formula (Ibb)

X[2] = O, S, or NR[13B]

In some embodiments, as shown in Method B1, Intermediate B1, which bears a carboxylic group, undergoes a Curtius Rearrangement reaction to give Intermediate B2, which bears an isocyanate moiety. The Curtius Rearrangement conditions include, but are not limited to, (i) Intermediate B1 (1.0 eq.), Et$_3$N (1.3 eq.), ClCO$_2$Et (1.5 eq.), −10° C., THF, 2 h; (ii) NaN$_3$ (1.7 eq.), −10° C., H$_2$O, 1 h; then toluene, reflux, 1 h. The Intermediate B2 bearing an isocyanate group reacts with an alcohol, thiol or free amine to afford a compound of Formula (Ibb). Conditions for reacting with the isocyanate group include, but are not limited to, nucleophilic reagent (HX'—R', 0.9 eq.), dioxane, reflux, 24 h. In Formula (Ibb), the —R[13] moiety in Formula (I) becomes —X[2]—R[13C], wherein X[2] is O, S or NR[13B].

Additional Embodiments

Embodiments include embodiments P1 to P33 following.

Embodiment P1. A compound of Formula (I), or a pharmaceutically acceptable salt, solvate, tautomer, or stereoisomer thereof:

Formula (I)

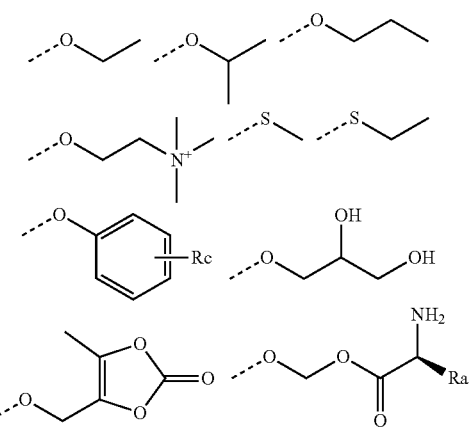

wherein

R[1] is hydrogen, halide, amino, R[11]—NH—, R[12]—(CO)NH—, C$_{1-6}$ alkyl, C$_{1-6}$ alkoxy, hydroxy-substituted C$_{1-6}$ alkyl, cyano-substituted C$_{1-6}$ alkyl, or C$_{1-6}$alkoxy-substituted C$_{1-6}$ alkyl;

one of X and Y is nitrogen while the other is nitrogen or oxygen;

ring A is phenyl, or phenyl substituted with a halide or 1 or 2 C$_{1-6}$ alkyl;

Z is a bond, —CH$_2$—, —CH$_2$CH$_2$—, —O—, —S—, —CH$_2$O—, —OCH$_2$—, —NH—, —CH$_2$NH—, —NHCH$_2$—, —CH$_2$S—, or —SCH$_2$—;

W is N or N[+]-G, wherein G is —CH$_2$OPO$_3$H$_2$,

[structures showing phosphate prodrug groups with CO$_2$Rb, Ra substituents]

R[2] is selected from the group consisting of:

[structures showing various R[2] groups including ether, thioether, quaternary ammonium, phenyl, diol, dioxolone, and amino acid ester groups with Ra, Rc substituents]

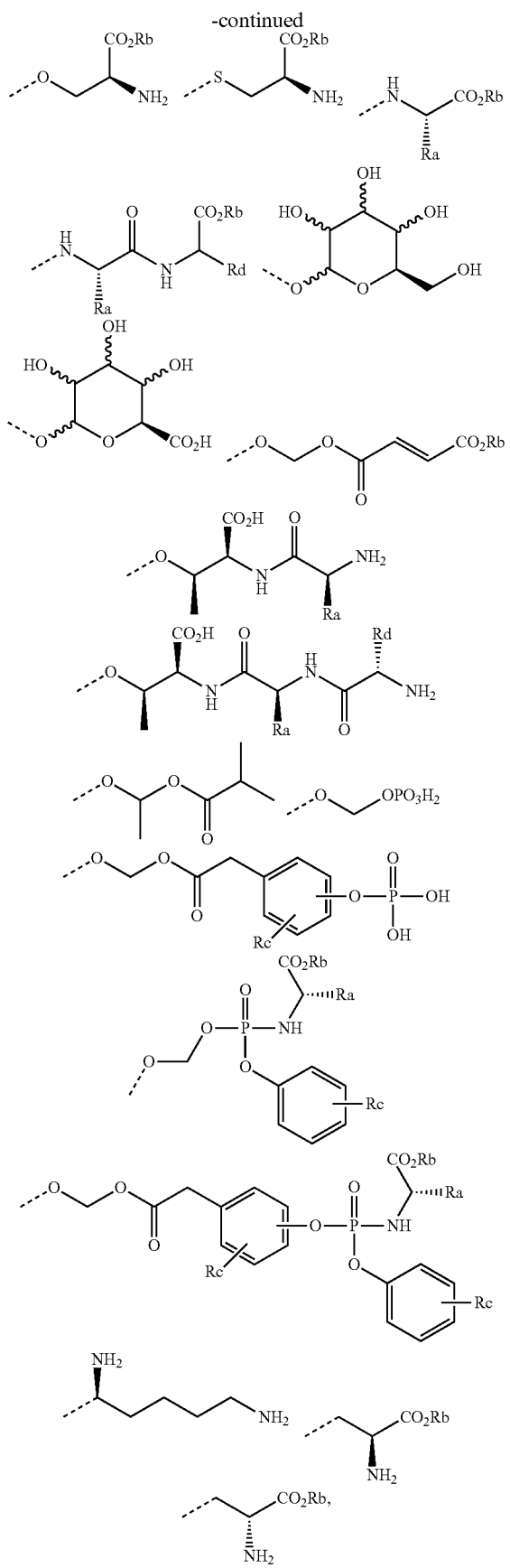

or R² together with the carbonyl group it attaches to is independently an amino acid, a dipeptide, or a tripeptide, comprising

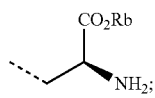

each of Ra and Rd is independently H, methyl, isopropyl, 1-methylpropyl, 2-methylpropyl, 1-hydroxyethyl, or a side chain on a natural amino acid;

Rb is independently H, ethyl, isopropyl, an amino acid bonded through a first amino group on the amino acid, a dipeptide bonded through a second amino group on the dipeptide;

Rc is independently H, F, CF₃, OH, or

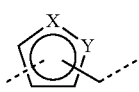

$R^3$ is H or halide, or $C_{1-6}$ alkyl, $C_{3-8}$ cycloalkyl, $C_{6-10}$ aryl, 5- or 6-membered heteroaryl, or 5- or 6-membered non-aromatic heterocyclic, all of which are non-substituted or substituted with 1 or 2 groups selected from the group consisting of halide, cyano, $C_{1-6}$ alkyl, $C_{1-6}$alkoxy, $C_{1-6}$ alkoxycarbonyl, $C_{3-8}$ cycloalkyl, $C_{2-6}$ alkenyl, and $C_{2-6}$ alkynyl;

$R^4$ is H or halide;

$R^{11}$ is $C_{1-6}$ alkyl, hydroxy-substituted $C_{1-6}$ alkyl, $C_{1-6}$ alkoxy-substituted $C_{1-6}$ alkyl, or $C_{1-6}$ alkoxycarbonyl-substituted $C_{1-6}$ alkyl; and $R^{12}$ is $C_{1-6}$ alkyl or $C_{1-6}$ alkoxy-substituted $C_{1-6}$ alkyl.

Embodiment P2. The compound of Embodiment P1, or a pharmaceutically acceptable salt, solvate, tautomer, or stereoisomer thereof, wherein one of X and Y is a nitrogen atom and the other is an oxygen atom.

Embodiment P3. The compound of Embodiment P2, or a pharmaceutically acceptable salt, solvate, tautomer, or stereoisomer thereof, wherein a partial structure represented by

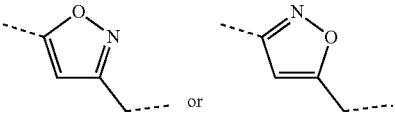

Embodiment P4. The compound of Embodiment P1, or a pharmaceutically acceptable salt, solvate, tautomer, or stereoisomer thereof, wherein Z is —O—, CH₂O, or OCH₂.

Embodiment P5. The compound of Embodiment 1, or a pharmaceutically acceptable salt, solvate, tautomer, or stereoisomer thereof, wherein $R^3$ is an unsubstituted pyridine ring.

Embodiment P6. The compound of Embodiment P1, or a pharmaceutically acceptable salt, solvate, tautomer, or stereoisomer thereof, wherein the ring A is phenyl ring.

Embodiment P7. The compound of Embodiment P1, or a pharmaceutically acceptable salt, solvate, tautomer, or stereoisomer thereof, wherein W is N.

Embodiment P8. The compound of Embodiment P1, or a pharmaceutically acceptable salt, solvate, tautomer, or stereoisomer thereof, wherein W is $N^+$-G.

Embodiment P9. The compound of Embodiment P8, or a pharmaceutically acceptable salt, solvate, tautomer, or stereoisomer thereof, wherein G is —$CH_2OPO_3H_2$,

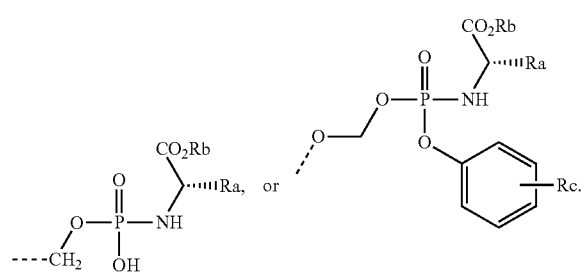

Embodiment P10. The compound of Embodiment P8, or a pharmaceutically acceptable salt, solvate, tautomer, or stereoisomer thereof, wherein G is

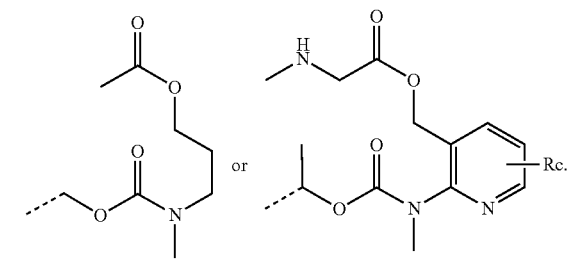

Embodiment P11. The compound of Embodiment P1, or a pharmaceutically acceptable salt, solvate, tautomer, or stereoisomer thereof, wherein $R^2$ is selected from the group consisting of:

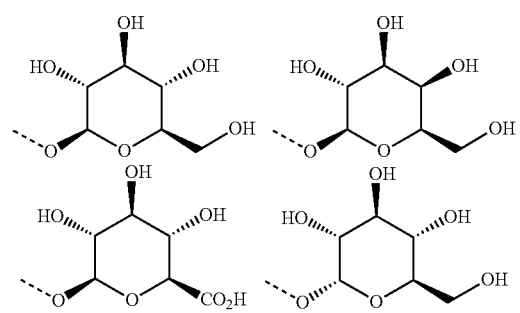

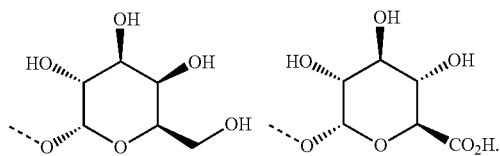

Embodiment P12. The compound of Embodiment P1, or a pharmaceutically acceptable salt, solvate, tautomer, or stereoisomer thereof, wherein $R^2$ is selected from the group consisting of:

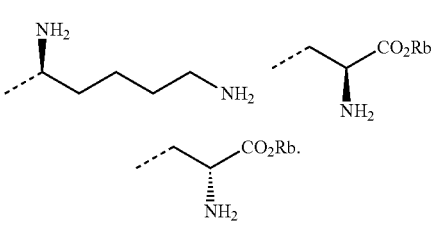

Embodiment P13. The compound of Embodiment P1, or a pharmaceutically acceptable salt, solvate, tautomer, or stereoisomer thereof, wherein $R^2$ is selected from the group consisting of:

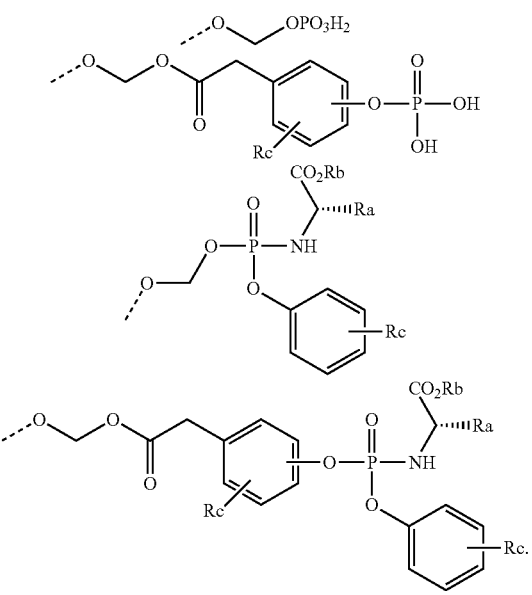

Embodiment P14. The compound of Embodiment P1, or a pharmaceutically acceptable salt, solvate, tautomer, or stereoisomer thereof, wherein $R^2$ is selected from the group consisting of:

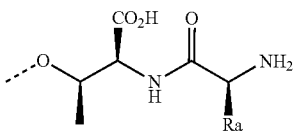

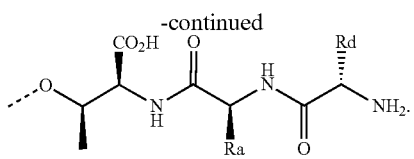

Embodiment P15. The compound of Embodiment P1, or a pharmaceutically acceptable salt, solvate, tautomer, or stereoisomer thereof, wherein $R^2$ is selected from the group consisting of:

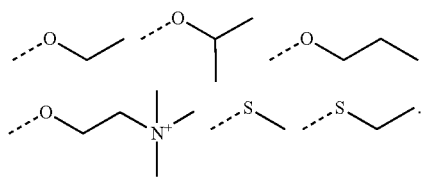

Embodiment P16. The compound of Embodiment P1, or a pharmaceutically acceptable salt, solvate, tautomer, or stereoisomer thereof, $R^2$ is selected from the group consisting of:

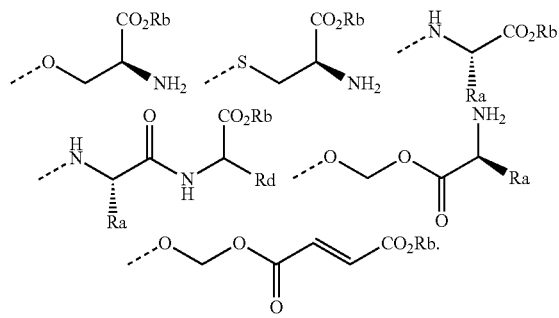

Embodiment P17. The compound of Embodiment P1, or a pharmaceutically acceptable salt, solvate, tautomer, or stereoisomer thereof, wherein $R^1$ and $R^4$ are H.

Embodiment P18. The compound of Embodiment P1, wherein the compound of Formula (I) is of Formula (Ia), or a pharmaceutically acceptable salt, solvate, tautomer, or stereoisomer thereof:

Formula (Ia)

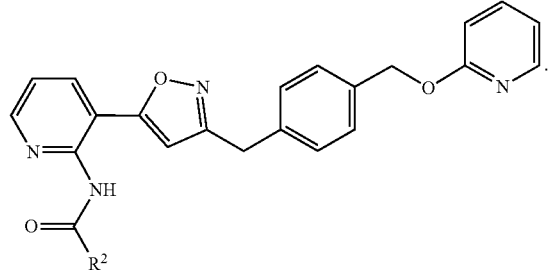

Embodiment P19. A compound of Formula (Ib), or a pharmaceutically acceptable salt, solvate, tautomer, or stereoisomer thereof:

Formula (Ib)

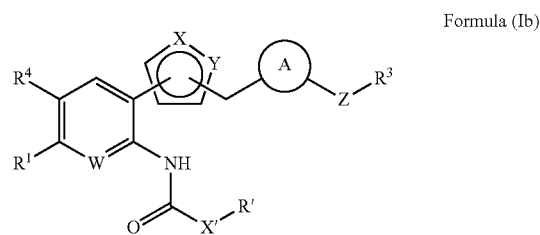

wherein $R^1$ is hydrogen, halide, amino, $R^{11}$—NH—, $R^{12}$—(CO)NH—, $C_{1-6}$ alkyl, $C_{1-6}$ alkoxy, hydroxy-substituted $C_{1-6}$ alkyl, cyano-substituted $C_{1-6}$ alkyl, or $C_{1-6}$alkoxy-substituted $C_{1-6}$ alkyl;

one of X and Y is nitrogen while the other is nitrogen or oxygen;

ring A is phenyl, or phenyl substituted with a halide or 1 or 2 $C_{1-6}$ alkyl;

Z is a bond, —CH$_2$—, —CH$_2$CH$_2$—, —O—, —S—, —CH$_2$O—, —OCH$_2$—, —NH—, —CH$_2$NH—, —NHCH$_2$—, —CH$_2$S—, or —SCH$_2$—:

W is N or N$^+$-G, wherein G is —CH$_2$OPO$_3$H$_2$,

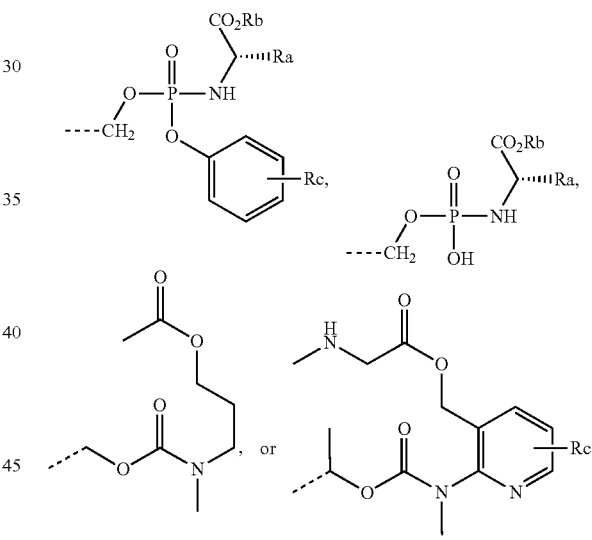

X' is O, S or NR";

R" is H, $C_{1-6}$ alkyl, hydroxy-substituted $C_{1-6}$ alkyl, cyano-substituted $C_{1-6}$ alkyl, or $C_{1-6}$ alkoxy-substituted $C_{1-6}$ alkyl;

R' is optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted cycloalkyl, optionally substituted heterocycloalkyl, optionally substituted aryl, or optionally substituted heteroaryl;

each of Ra and Rd is independently H, methyl, isopropyl, 1-methylpropyl, 2-methylpropyl, 1-hydroxyethyl, or a side chain on a natural amino acid;

Rb is independently H, ethyl, isopropyl, an amino acid bonded through a first amino group on the amino acid, a dipeptide bonded through a second amino group on the dipeptide;

Rc is independently H, F, $CF_3$, OH, or

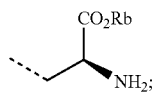

$R^3$ is H or halide, or $C_{1-6}$ alkyl, $C_{3-8}$ cycloalkyl, $C_{6-10}$ aryl, 5- or 6-membered heteroaryl, or 5- or 6-membered non-aromatic heterocyclic, all of which are non-substituted or substituted with 1 or 2 groups selected from the group consisting of halide, cyano, $C_{1-6}$ alkyl, $C_{1-6}$ alkoxy, $C_{1-6}$ alkoxycarbonyl, $C_{3-8}$ cycloalkyl, $C_{2-6}$ alkenyl, and $C_{2-6}$ alkynyl;

$R^4$ is H or halide;

$R^{11}$ is $C_{1-6}$ alkyl, hydroxy-substituted $C_{1-6}$ alkyl, $C_{1-6}$ alkoxy-substituted $C_{1-6}$ alkyl, or $C_{1-6}$ alkoxycarbonyl-substituted $C_{1-6}$ alkyl; and $R^{12}$ is $C_{1-6}$ alkyl or $C_{1-6}$ alkoxy-substituted $C_{1-6}$ alkyl.

Embodiment P20. The compound of Embodiment P19, or a pharmaceutically acceptable salt, solvate, tautomer, or stereoisomer thereof, wherein one of X and Y is a nitrogen atom and the other is an oxygen atom.

Embodiment P21. The compound of Embodiment P20, or a pharmaceutically acceptable salt, solvate, tautomer, or stereoisomer thereof, wherein a partial structure represented by

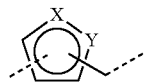

in Formula (Ib) is

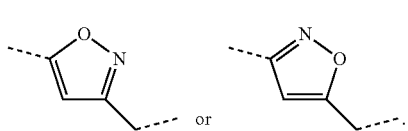

Embodiment P22. The compound of Embodiment P19, or a pharmaceutically acceptable salt, solvate, tautomer, or stereoisomer thereof, wherein Z is —O—, —$CH_2O$—, or —$OCH_2$—.

Embodiment P23. The compound of Embodiment P19, or a pharmaceutically acceptable salt, solvate, tautomer, or stereoisomer thereof, wherein $R^3$ is an unsubstituted pyridine ring.

Embodiment P24. The compound of Embodiment P19, or a pharmaceutically acceptable salt, solvate, tautomer, or stereoisomer thereof, wherein the ring A is phenyl ring.

Embodiment P25. The compound of Embodiment P19, or a pharmaceutically acceptable salt, solvate, tautomer, or stereoisomer thereof, wherein W is N.

Embodiment P26. The compound of Embodiment P19, or a pharmaceutically acceptable salt, solvate, tautomer, or stereoisomer thereof, wherein W is $N^+$-G.

Embodiment P27. The compound of Embodiment P26, or a pharmaceutically acceptable salt, solvate, tautomer, or stereoisomer thereof, wherein G is —$CH_2OPO_3H_2$,

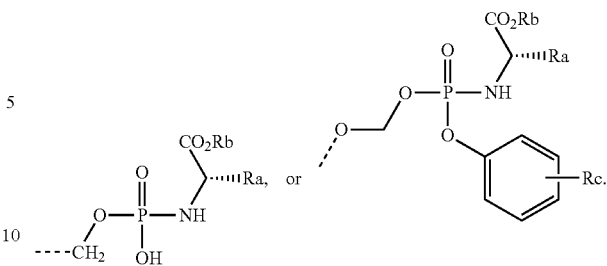

Embodiment P28. The compound of Embodiment P26, or a pharmaceutically acceptable salt, solvate, tautomer, or stereoisomer thereof, wherein G is

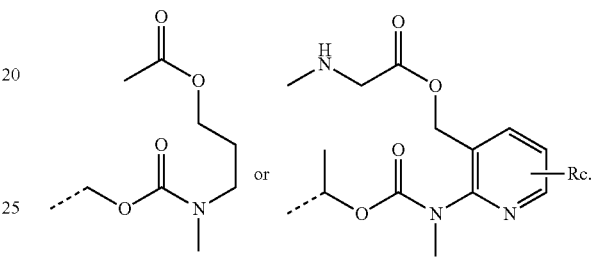

Embodiment P29. The compound of Embodiment P19, or a pharmaceutically acceptable salt, solvate, tautomer, or stereoisomer thereof, wherein $R^1$ and $R^4$ are H.

Embodiment P30. The compound of Embodiment P19, wherein the compound of Formula (Ib) is of Formula (Ibb), or a pharmaceutically acceptable salt, solvate, tautomer, or stereoisomer thereof:

Formula (Ibb)

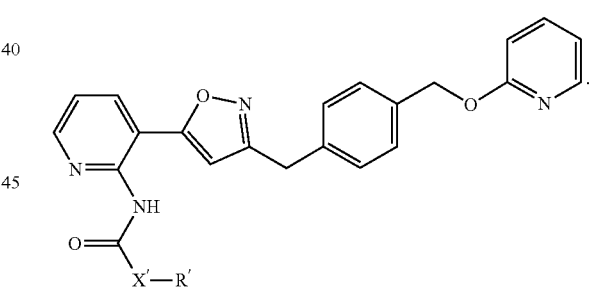

Embodiment P31. A pharmaceutical composition comprising a pharmaceutically effective amount of the compound of Embodiment P1 or Embodiment P19, or a pharmaceutically acceptable salt, solvate, tautomer, or stereoisomer thereof, in admixture with a pharmaceutically acceptable carrier.

Embodiment P32. An antifungal agent comprising a fungicidally effective amount of the compound of Embodiment P1 or Embodiment P19, or a pharmaceutically acceptable salt, solvate, tautomer, or stereoisomer thereof, as an active ingredient in admixture with a pharmaceutically acceptable carrier.

Embodiment P33. A method for treating a fungal infection comprising administering to a subject in need thereof a pharmacologically effective dose of the compound of Embodiment P1 or Embodiment P19, or a pharmaceutically acceptable salt, solvate, tautomer, or stereoisomer thereof.

Embodiments include embodiments P'1 to P'41 following.

Embodiment P'1. A compound of structural Formula (II), or a pharmaceutically acceptable salt, solvate, tautomer, or stereoisomer thereof:

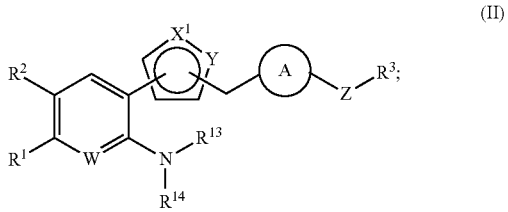

(II)

wherein:

n13 and n15 are independently an integer from 0 to 4;

v13 and v15 are independently 1 or 2;

one of $X^1$ and Y is nitrogen while the other is nitrogen or oxygen;

W is N or $N^+$—$R^{15}$;

A is substituted or unsubstituted phenyl or substituted or unsubstituted pyridinyl;

Z is a bond, —$(CH_2)_{z1}$—, —O—, —S—, —$CH_2O$—, —$OCH_2$—, —NH—, —$CH_2NH$—, —$NHCH_2$—, —$CH_2S$—, or —$SCH_2$—;

z1 is 1 or 2;

$R^1$ is hydrogen, halogen, —$NR^{1B}R^{1C}$, —$C(O)NR^{1B}R^{1C}$, —$OR^{1A}$, substituted or unsubstituted alkyl, or substituted or unsubstituted heteroalkyl;

$R^2$ is hydrogen or halogen;

$R^3$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is —$SO_{n13}R^{13A}$, —$SO_{v13}NR^{13B}R^{13C}$, —$C(O)R^{13D}$, —$C(S)R^{13D}$, —$C(O)X^2R^{13C}$, —$C(S)OR^{13D}$, —$C(S)NR^{13B}R^{13C}$, substituted alkyl, substituted or unsubstituted heteroalkyl; or $R^{13}$ together with the nitrogen to which it is attached forms an amino acid, a dipeptide, or a tripeptide;

$X^2$ is —O—, —S—, or —$NR^{13B}$;

$R^{14}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is —$SO_{n15}R^{15A}$, —$SO_{v15}NR^{15B}R^{15C}$, —$C(O)R^{15D}$, —$C(S)R^{15D}$, —$C(O)OR^{15D}$, —$C(S)OR^{15D}$, —$C(O)SR^{15D}$, —$C(O)NR^{15B}R^{15C}$, —$C(S)NR^{15B}R^{15C}$, —$CH_2OPO_3H_2$, —$CH_2OSO_3H_2$, —$CH_2OPO_3H^-$, —$CH_2OSO_3H^-$, —$C(O)CH_2X^3$, substituted, or unsubstituted heteroalkyl;

$X^3$ is —F, —Cl, —Br, —I, —$CHF_2$, —$CHCl_2$, —$CHBr_2$, —$CHI_2$, —$CF_3$, —$CCl_3$, —$CBr_3$, —$CI_3$, or —$NO_2$; and $R^{1A}$, $R^{1B}$, $R^{1C}$, $R^{13A}$, $R^{13B}$, $R^{13C}$, $R^{13D}$, $R^{15A}$, $R^{15B}$, $R^{15C}$, and $R^{15D}$ are independently hydrogen, halogen, —$CF_3$, —$CCl_3$, —$CBr_3$, —$CI_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{13B}$ and $R^{13C}$ or $R^{15B}$ and $R^{15C}$ substituents bonded to the same nitrogen atom may optionally be joined to form a substituted or unsubstituted heterocycloalkyl or substituted or unsubstituted heteroaryl.

Embodiment P'2. The compound of Embodiment P'1, or a pharmaceutically acceptable salt, solvate, tautomer, or stereoisomer thereof, wherein W is $N^+$—$R^{15}$.

Embodiment P'3. The compound of Embodiment P'1 or P'2, or a pharmaceutically acceptable salt, solvate, tautomer, or stereoisomer thereof, wherein $R^{15}$ is substituted or unsubstituted heteroalkyl.

Embodiment P'4. The compound of Embodiment P'1 or P'2, or a pharmaceutically acceptable salt, solvate, tautomer, or stereoisomer thereof, wherein $R^{15}$ is —$CH_2OPO_3H_2$, —$CH_2OPO_3H^-$, —$CH_2OSO_3H$, or —$CH_2OSO_3^-$.

Embodiment P'5. The compound of Embodiment P'1 or P'2, or a pharmaceutically acceptable salt, solvate, tautomer, or stereoisomer thereof, wherein $R^{15}$ is —$C(O)CH_2X^3$.

Embodiment P'6. The compound of any one of Embodiments P'1-P'3, or a pharmaceutically acceptable salt, solvate, tautomer, or stereoisomer thereof, wherein $R^{15}$ is tautomer, or stereoisomer thereof, wherein $R^{15}$ is:

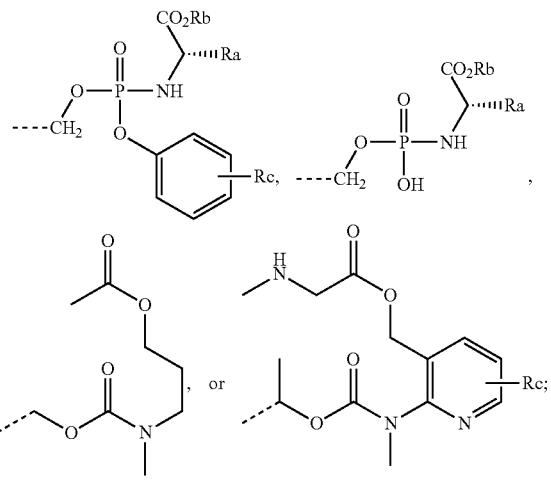

wherein:

Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and Rb and Rc are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P'7. The compound of Embodiment P'1, or a pharmaceutically acceptable salt, solvate, tautomer, or stereoisomer thereof, wherein W is N.

Embodiment P'8. The compound of any one of Embodiments P'1-P'7, or a pharmaceutically acceptable salt, solvate, tautomer, or stereoisomer thereof, wherein $R^{13}$ is —$C(O)R^{13D}$.

Embodiment P'9. The compound of any one of Embodiments P'1-P'8, or a pharmaceutically acceptable salt, solvate, tautomer, or stereoisomer thereof, wherein the compound has structural Formula (I):

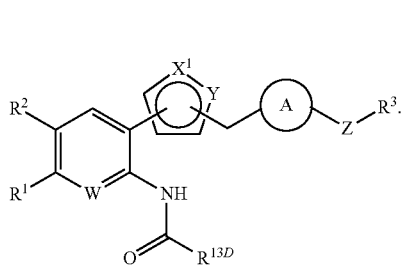

Embodiment P'10. The compound of any one of Embodiments P'1-P'9, or a pharmaceutically acceptable salt, solvate, tautomer, or stereoisomer thereof, wherein $R^{13D}$ is substituted alkyl or substituted or unsubstituted heteroalkyl.

Embodiment P'11. The compound of any one of Embodiments P'1-P'10, or a pharmaceutically acceptable salt, solvate, tautomer, or stereoisomer thereof, wherein $R^{13D}$ is —$CH_2Cl$.

Embodiment P'12. The compound of any one of Embodiments P'1-P'10, or a pharmaceutically acceptable salt, solvate, tautomer, or stereoisomer thereof, wherein $R^{13D}$ is —$SCH_3$, —$OCH_2CH_3$, —$SCH_2CH_3$,

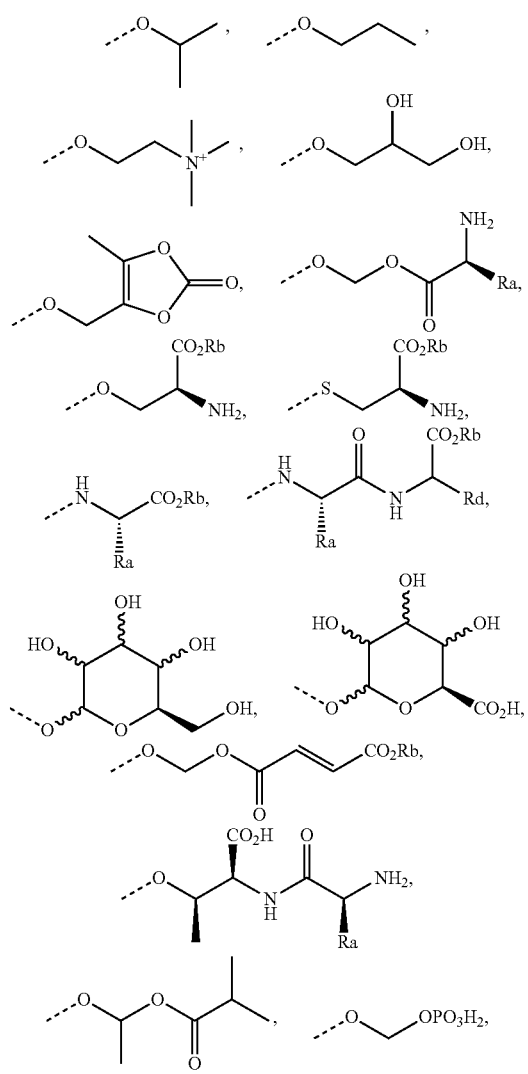

wherein:
Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and
Rb and Rc are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P'13. The compound of Embodiment P'12, or a pharmaceutically acceptable salt, solvate, tautomer, or stereoisomer thereof, wherein:
Ra and Rd are independently hydrogen, methyl, isopropyl, 1-methylpropyl, 2-methylpropyl, 1-hydroxyethyl, or a side chain on a natural amino acid;
Rb is hydrogen, ethyl, isopropyl, an amino acid, or a dipeptide; and
Rc is independently hydrogen, —F, —$CF_3$, —OH, or Embodiment P'14. The compound of any one of Embodiments P'1-P'10 or P'12, or a pharmaceutically acceptable salt, solvate, tautomer, or stereoisomer thereof, wherein $R^{13D}$ is:

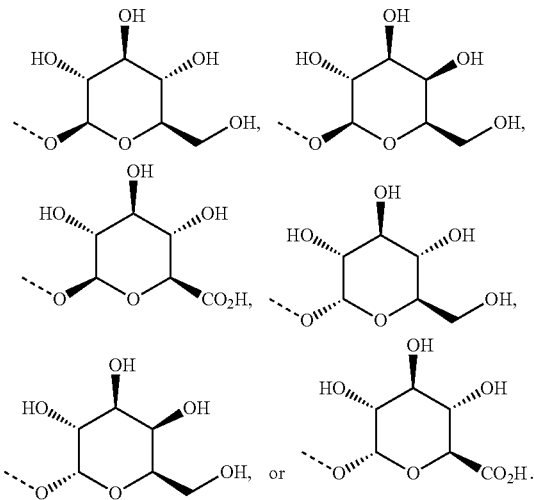

Embodiment P'15. The compound of any one of Embodiments P'1-P'10, or a pharmaceutically acceptable salt, solvate, tautomer, or stereoisomer thereof, wherein $R^{13D}$ is:

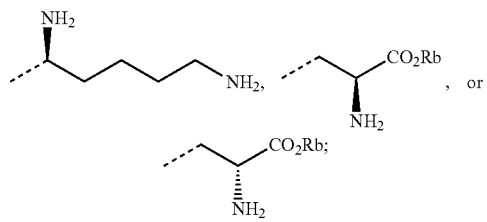

wherein

Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P'16. The compound of any one of Embodiments P'1-P'10, or a pharmaceutically acceptable salt, solvate, tautomer, or stereoisomer thereof, wherein $R^{13D}$ is:

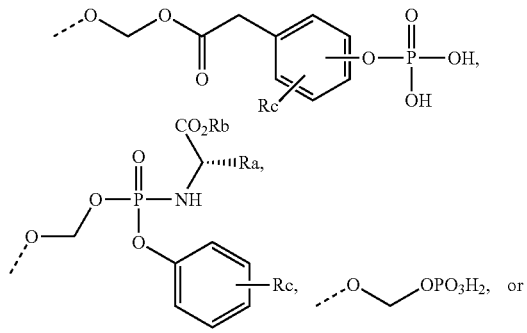

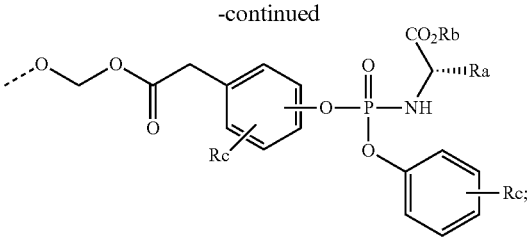

and
wherein:
Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and
Rb and Rc are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P'17. The compound of any one of Embodiments P'1-PTO, or a pharmaceutically acceptable salt, solvate, tautomer, or stereoisomer thereof, wherein $R^{13D}$ is:

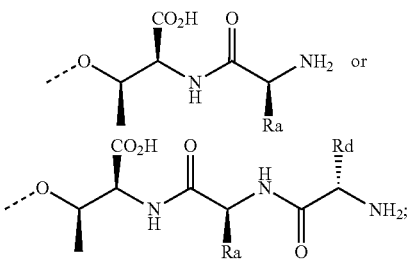

wherein:
Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid.

Embodiment P'18. The compound of any one of Embodiments P'1-P'10, or a pharmaceutically acceptable salt, solvate, tautomer, or stereoisomer thereof, wherein $R^{13D}$ is $-SCH_3$, $-OCH_2CH_3$, $-SCH_2CH_3$.

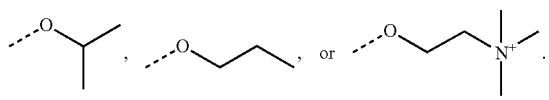

Embodiment P'19. The compound of any one of Embodiments P'1-P'10, or a pharmaceutically acceptable salt, solvate, tautomer, or stereoisomer thereof, wherein $R^{13D}$ is:

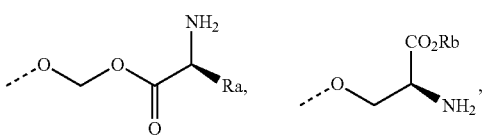

-continued

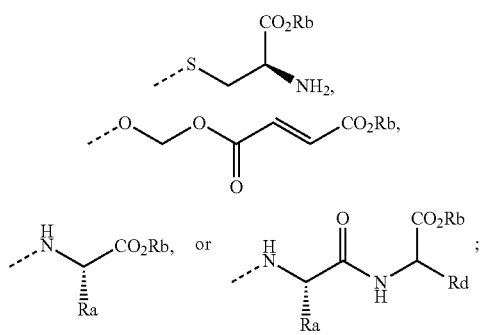

wherein:

Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P'20. The compound of any one of Embodiments P'1-P'7, or a pharmaceutically acceptable salt, solvate, tautomer, or stereoisomer thereof, wherein $R^{13}$ together with the nitrogen to which it is attached forms an amino acid, a dipeptide, or a tripeptide.

Embodiment P'21, The compound of any one of Embodiments P'1-P'7 or P'20 or a pharmaceutically acceptable salt, solvate, tautomer, or stereoisomer thereof, wherein $R^{13}$ is:

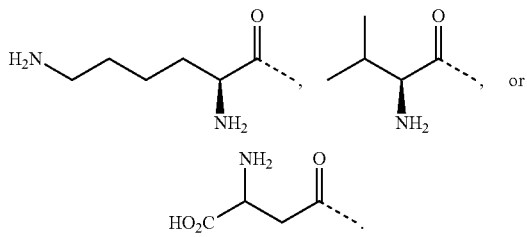

Embodiment P'22. The compound of any one of Embodiments P'1-P'21, or a pharmaceutically acceptable salt, solvate, tautomer, or stereoisomer thereof, wherein one of $X^1$ and Y is a nitrogen atom and the other is an oxygen atom.

Embodiment P'23. The compound of any one of Embodiments P'1-P'22, or a pharmaceutically acceptable salt, solvate, tautomer, or stereoisomer thereof, wherein a partial structure represented by in Formula (II) is

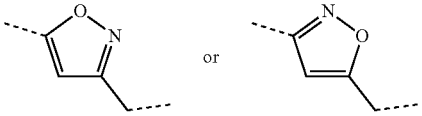

Embodiment P'24. The compound of any one of Embodiments P'1-P'23, or a pharmaceutically acceptable salt, solvate, tautomer, or stereoisomer thereof, wherein Z is —O—, —CH$_2$O—, or —OCH$_2$—.

Embodiment P'25. The compound of any one of Embodiments P'1-P'24, or a pharmaceutically acceptable salt, solvate, tautomer, or stereoisomer thereof, wherein $R^3$ is unsubstituted pyridine.

Embodiment P'26. The compound of any one of Embodiments P'1-P'25, or a pharmaceutically acceptable salt, solvate, tautomer, or stereoisomer thereof, wherein A is unsubstituted phenyl.

Embodiment P'27. The compound of any one of Embodiments P'1-P'25, or a pharmaceutically acceptable salt, solvate, tautomer, or stereoisomer thereof, wherein $R^1$ and $R^2$ are hydrogen.

Embodiment P'28. The compound of any one of Embodiments P'1, or a pharmaceutically acceptable salt, solvate, tautomer, or stereoisomer thereof, wherein the compound has structural Formula (Ia):

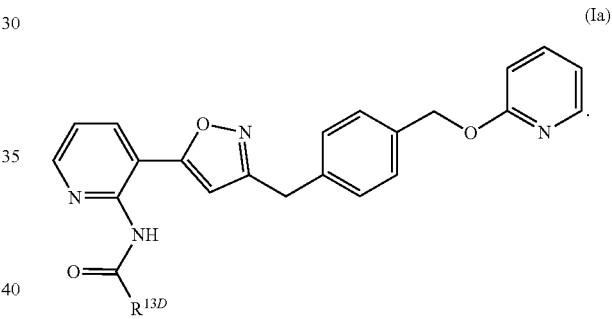

Embodiment P'29. The compound of any one of Embodiments P'1-P'7, or a pharmaceutically acceptable salt, solvate, tautomer, or stereoisomer thereof, wherein $R^{13}$ is —C(O)X$^2$R$^{13C}$.

Embodiment P'30. The compound of any one of Embodiments P'1-P'7 or P'29, or a pharmaceutically acceptable salt, solvate, tautomer, or stereoisomer thereof, wherein the compound has structural Formula (Ib):

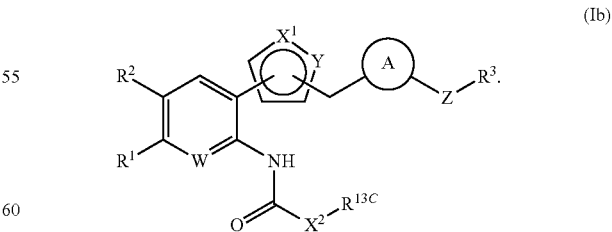

Embodiment P'31. The compound of Embodiment P'30, or a pharmaceutically acceptable salt, solvate, tautomer, or stereoisomer thereof, wherein $R^{13C}$ is hydrogen, substituted or unsubstituted alkyl or substituted or unsubstituted heteroalkyl.

Embodiment P'32. The compound of Embodiment P'30 or P'31, or a pharmaceutically acceptable salt, solvate, tautomer, or stereoisomer thereof, wherein a partial structure represented by

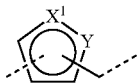

in Formula (II) is

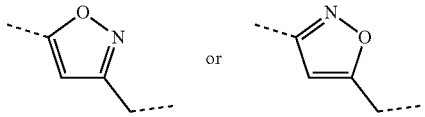

Embodiment P'33. The compound of any one of Embodiments P'30-P'32, or a pharmaceutically acceptable salt, solvate, tautomer, or stereoisomer thereof, wherein Z is —O—, —CH$_2$O—, or —OCH$_2$—.

Embodiment P'34. The compound of any one of Embodiments P'30-P'33, or a pharmaceutically acceptable salt, solvate, tautomer, or stereoisomer thereof, wherein R$^3$ is unsubstituted pyridine.

Embodiment P'35. The compound of any one of Embodiments P'30-P'34, or a pharmaceutically acceptable salt, solvate, tautomer, or stereoisomer thereof, wherein A is unsubstituted phenyl.

Embodiment P'36. The compound of any one of Embodiments P'30-P'35, or a pharmaceutically acceptable salt, solvate, tautomer, or stereoisomer thereof, wherein R$^1$ and R$^2$ are hydrogen.

Embodiment P'37. The compound of any one of Embodiments P'1, P'30, or 31, or a pharmaceutically acceptable salt, solvate, tautomer, or stereoisomer thereof, wherein the compound has structural Formula I Ibb):

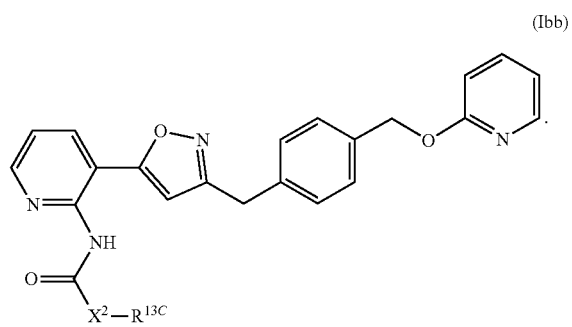

(Ibb)

Embodiment P'38. A pharmaceutical composition comprising a pharmaceutically effective amount of the compound of any one of Embodiments P'1-P'37, or a pharmaceutically acceptable salt, solvate, tautomer, or stereoisomer thereof, and at least one pharmaceutically acceptable carrier.

Embodiment P'39. A method of treating a fungal disease or infection, comprising administering to a subject in need thereof a pharmacologically effective amount of the compound of any one of Embodiments P'1-P'37, or a pharmaceutically acceptable salt, solvate, tautomer, or stereoisomer thereof, or the pharmaceutical composition of Embodiment P'38.

Embodiment P'40. The method of Embodiment P'39, wherein the fungal disease or infection is a *Cryptococcus* disease or infection.

Embodiment P'41. The method of Embodiment P'39 or P'40, wherein the fungal disease or infection is azole-resistant and/or echinocandin-resistant.

Embodiments include embodiments 1 to 52 following.

Embodiment 1. A compound of structural Formula (II), or a pharmaceutically acceptable salt, solvate, tautomer, or stereoisomer thereof:

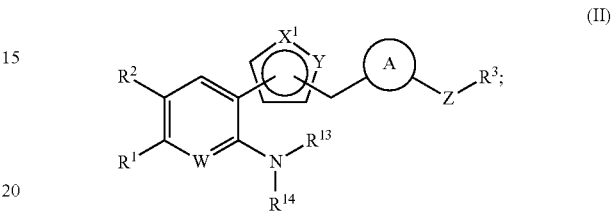

(II)

wherein:
one of X$^1$ and Y is nitrogen while the other is nitrogen or oxygen;
W is N or N$^+$—R$^{15}$;
A is substituted or unsubstituted phenyl or substituted or unsubstituted pyridinyl;
Z is a bond, —(CH$_2$)$_{z1}$—, —O—, —S—, —CH$_2$O—, —OCH$_2$—, —NH—, —CH$_2$NH—, —NHCH$_2$—, —CH$_2$S—, or —SCH$_2$—;
z1 is 1 or 2;
R$^1$ is hydrogen, halogen, —NR$^{1B}$R$^{1C}$, —C(O)NR$^{1B}$R$^{1C}$, —OR$^{1A}$, substituted or unsubstituted alkyl, or substituted or unsubstituted heteroalkyl;
R$^2$ is hydrogen or halogen;
R$^3$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{13}$ is —SO$_{n13}$R$^{13A}$, —SO$_{v13}$NR$^{13B}$R$^{13C}$, —C(O)R$^{13D}$, —C(S)R$^{13D}$, —C(O)X$^2$R$^{13C}$, —C(S)OR$^{13D}$, —C(S)NR$^{13B}$R$^{13C}$, substituted or unsubstituted alkyl, substituted or unsubstituted heteroalkyl; or R$^{13}$ together with the nitrogen to which it is attached forms an amino acid, a dipeptide, or a tripeptide;
X$^2$ is —O—, —S—, or —NR$^{13B}$;
R$^{14}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{15}$ is —SO$_{n15}$R$^{15A}$, —SO$_{v15}$NR$^{15B}$R$^{15C}$, —C(O)R$^{15D}$, —C(S)R$^{15D}$, —C(O)OR$^{15D}$, —C(S)OR$^{15D}$, —C(O) SR$^{15D}$, —C(O)NR$^{15B}$R$^{15C}$, —C(S)NR$^{15B}$R$^{15C}$, —CH$_2$OPO$_3$H$_2$, —CH$_2$OSO$_3$H, —CH$_2$OPO$_3$H$^-$, —CH$_2$OSO$_3^-$, —C(O)CH$_2$X$^3$, substituted, or unsubstituted heteroalkyl;
X$^3$ is —F, —Cl, —Br, —I, —CHF$_2$, —CHCl$_2$, —CHBr$_2$, —CHI$_2$, —CF$_3$, —CCl$_3$, —CBr$_3$, —CI$_3$, or —NO$_2$;
n13 and n15 are independently an integer from 0 to 4;
v13 and v15 are independently 1 or 2; and
R$^{1A}$, R$^{1B}$, R$^{1C}$, R$^{13A}$, R$^{13B}$, R$^{13C}$, R$^{13D}$, R$^{15A}$, R$^{15B}$, R$^{15C}$, and R$^{15D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or $R^{13B}$ and $R^{13C}$ or $R^{15B}$ and $R^{15C}$ substituents bonded to the same nitrogen atom may optionally be joined to form a substituted or unsubstituted heterocycloalkyl or substituted or unsubstituted heteroaryl.

Embodiment 2. The compound of Embodiment 1, or a pharmaceutically acceptable salt, solvate, tautomer, or stereoisomer thereof, wherein W is $N^+$—$R^{15}$.

Embodiment 3. The compound of Embodiment 1 or 2, or a pharmaceutically acceptable salt, solvate, tautomer, or stereoisomer thereof, wherein $R^{15}$ is substituted or unsubstituted heteroalkyl.

Embodiment 4. The compound of Embodiment 1 or 2, or a pharmaceutically acceptable salt, solvate, tautomer, or stereoisomer thereof, wherein $R^{15}$ is —$CH_2OPO_3H_2$, —$CH_2OPO_3H^-$, —$CH_2OSO_3H$, or —$CH_2OSO_3^-$.

Embodiment 5. The compound of Embodiment 1 or 2, or a pharmaceutically acceptable salt, solvate, tautomer, or stereoisomer thereof, wherein $R^{15}$ is —$C(O)CH_2X^3$.

Embodiment 6. The compound of any one of Embodiments 1-3, or a pharmaceutically acceptable salt, solvate, tautomer, or stereoisomer thereof, wherein $R^{15}$ is:

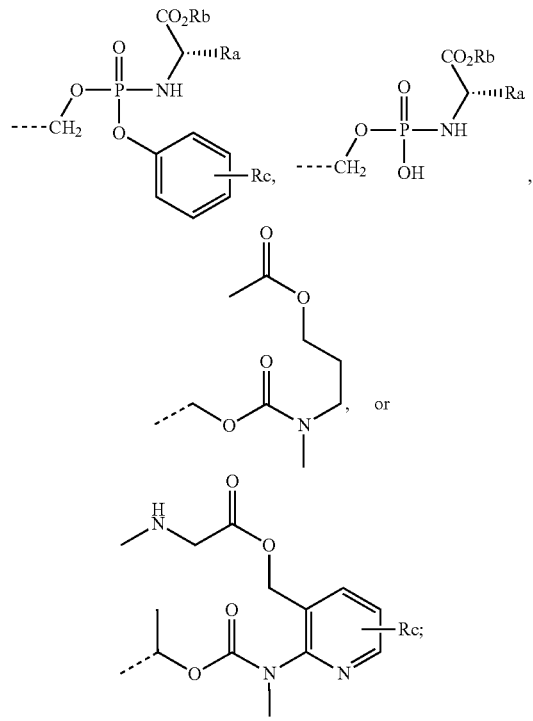

Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain of a natural amino acid; and Rb and Rc are independently hydrogen, halogen, hydroxy, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 7. The compound of Embodiment 1, or a pharmaceutically acceptable salt, solvate, tautomer, or stereoisomer thereof, wherein W is N.

Embodiment 8. The compound of any one of Embodiments 1-7, or a pharmaceutically acceptable salt, solvate, tautomer, or stereoisomer thereof, wherein $R^{13}$ is —$C(O)R^{13D}$ or —$C(O)X^2R^{13C}$.

Embodiment 9. The compound of Embodiment 8, or a pharmaceutically acceptable salt, solvate, tautomer, or stereoisomer thereof, wherein:

$R^{13}$ is —$C(O)X^2R^{13C}$;

$X^2$ is —O—; and $R^{13C}$ is substituted or unsubstituted phenyl.

Embodiment 10. The compound of any one of Embodiments 1-8, or a pharmaceutically acceptable salt, solvate, tautomer, or stereoisomer thereof, wherein the compound has structural Formula (I):

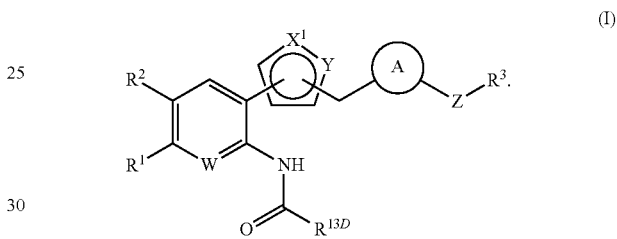

Embodiment 11. The compound of any one of Embodiments 1-8 or 10, or a pharmaceutically acceptable salt, solvate, tautomer, or stereoisomer thereof, wherein $R^{13D}$ is substituted alkyl, substituted or unsubstituted heteroalkyl, or substituted or unsubstituted heterocycloalkyl.

Embodiment 12. The compound of any one of Embodiments 1-8 or 10-11, or a pharmaceutically acceptable salt, solvate, tautomer, or stereoisomer thereof, wherein $R^{13D}$ is —$SCH_3$, —$OCH_2CH_3$, —$SCH_2CH_3$,

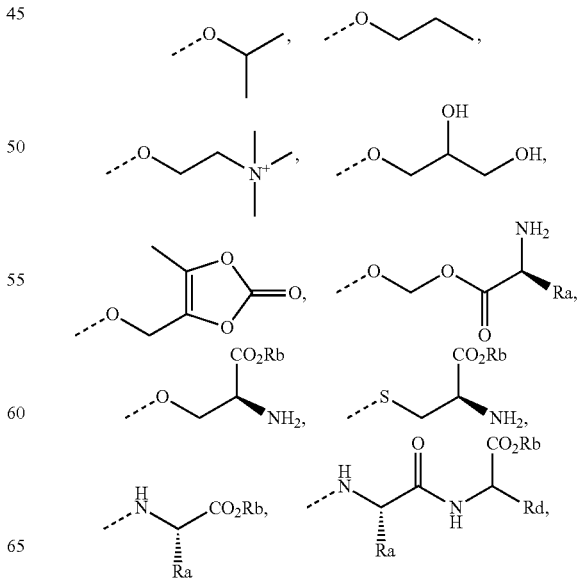

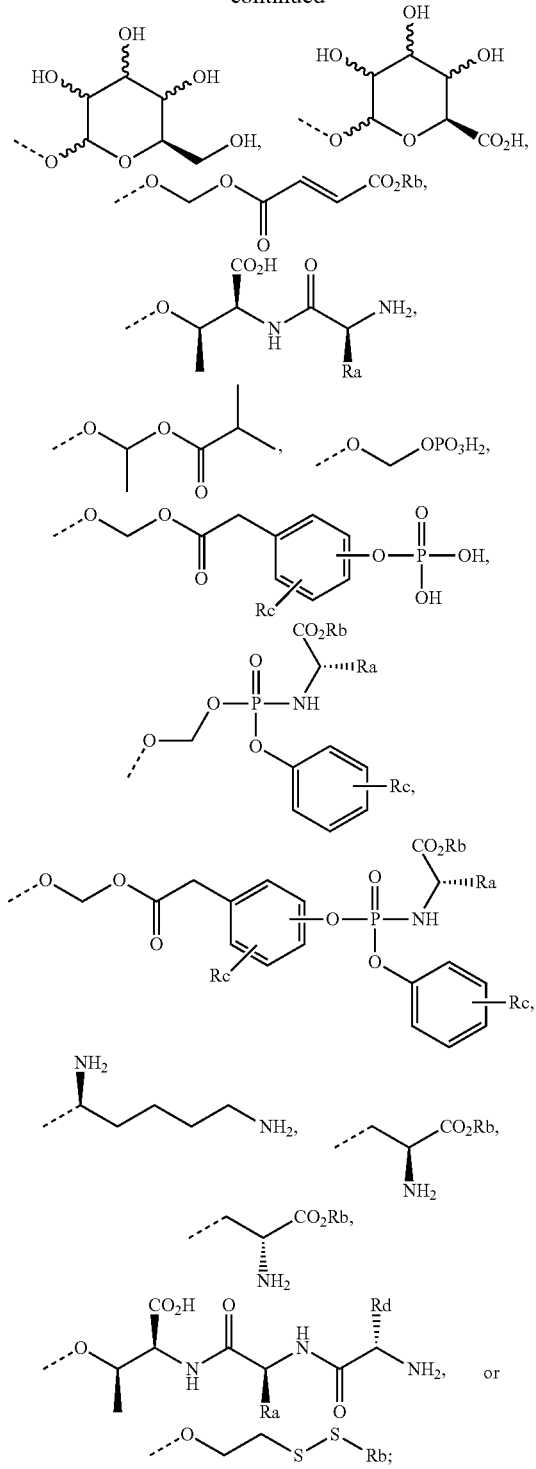

wherein:
Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain of a natural amino acid; and
Rb and Rc are independently hydrogen, halogen, hydroxy, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 13. The compound of Embodiment 12, or a pharmaceutically acceptable salt, solvate, tautomer, or stereoisomer thereof, wherein:
Ra and Rd are independently hydrogen, methyl, isopropyl, 1-methylpropyl, 2-methylpropyl, 1-hydroxyethyl, or a side chain of a natural amino acid;
Rb is hydrogen, ethyl, isopropyl, an amino acid, or a dipeptide; and
Rc is independently hydrogen, —F, —CF$_3$, —OH, or

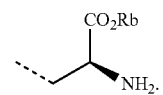

Embodiment 14. The compound of any one of Embodiments 1-8 or 10-11, or a pharmaceutically acceptable salt, solvate, tautomer, or stereoisomer thereof, wherein $R^{13D}$ is —CH$_2$Cl.

Embodiment 15. The compound of any one of Embodiments 1-8 or 10-11, or a pharmaceutically acceptable salt, solvate, tautomer, or stereoisomer thereof, wherein $R^{13D}$ is:

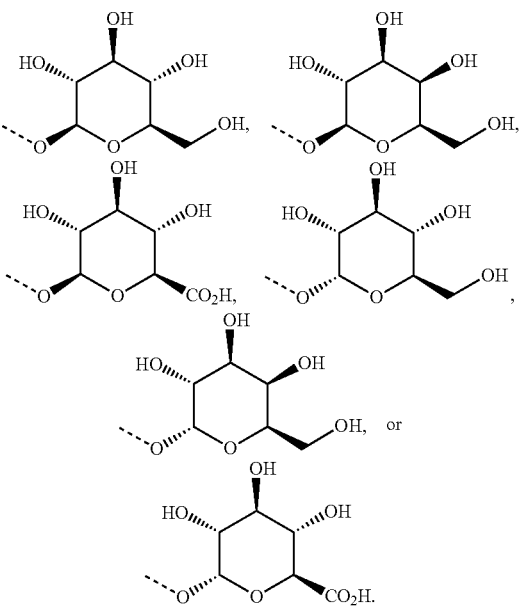

Embodiment 16. The compound of any one of Embodiments 1-8 or 10-11, or a pharmaceutically acceptable salt, solvate, tautomer, or stereoisomer thereof, wherein $R^{13D}$ is:

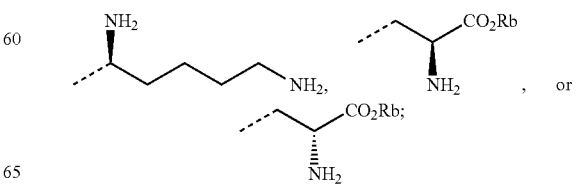

wherein:

Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 17. The compound of any one of Embodiments 1-8 or 10-11, or a pharmaceutically acceptable salt, solvate, tautomer, or stereoisomer thereof, wherein $R^{13D}$ is:

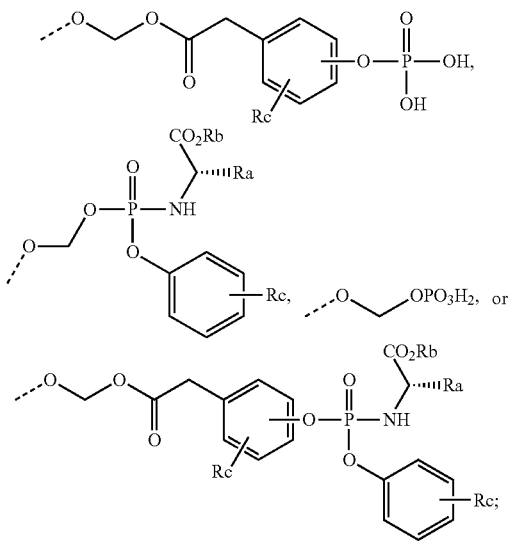

and wherein:

Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and Rb and Rc are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 18. The compound of any one of Embodiments 1-8 or 10-11, or a pharmaceutically acceptable salt, solvate, tautomer, or stereoisomer thereof, wherein $R^{13D}$ is:

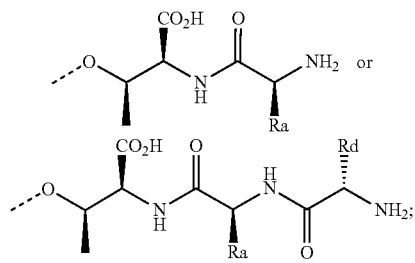

wherein:

Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid.

Embodiment 19. The compound of any one of Embodiments 1-8 or 10-11, or a pharmaceutically acceptable salt, solvate, tautomer, or stereoisomer thereof, wherein $R^{13D}$ is —SCH$_3$, —OCH$_2$CH$_3$, —SCH$_2$CH$_3$,

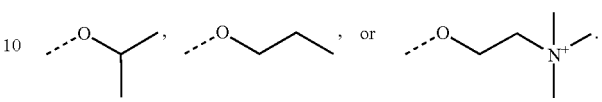

Embodiment 20. The compound of any one of Embodiments 1-8 or 10-11, or a pharmaceutically acceptable salt, solvate, tautomer, or stereoisomer thereof, wherein $R^{13D}$ is:

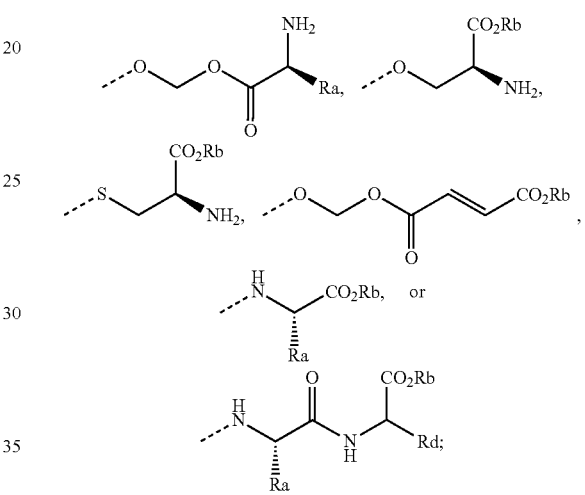

wherein:

Ra and Rd are independently hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain on a natural amino acid; and Rb is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 21. The compound of any one of Embodiments 1-7, or a pharmaceutically acceptable salt, solvate, tautomer, or stereoisomer thereof, wherein $R^{13}$ together with the nitrogen to which it is attached forms an amino acid, a dipeptide, or a tripeptide.

Embodiment 22. The compound of any one of Embodiments 1-7 or 21 or a pharmaceutically acceptable salt, solvate, tautomer, or stereoisomer thereof, wherein $R^{13}$ is:

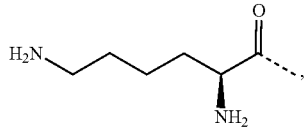

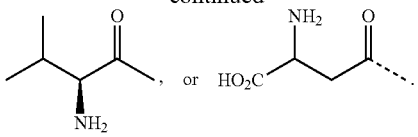

Embodiment 23. The compound of any one of Embodiments 1-22, or a pharmaceutically acceptable salt, solvate, tautomer, or stereoisomer thereof, wherein one of $X^1$ and Y is a nitrogen atom and the other is an oxygen atom.

Embodiment 24. The compound of any one of Embodiments 1-23, or a pharmaceutically acceptable salt, solvate, tautomer, or stereoisomer thereof, wherein a partial structure represented by

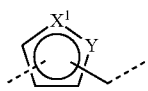

in Formulas (I), (Ib) and/or (II) is

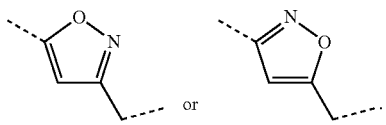

Embodiment 25. The compound of any one of Embodiments 1-24, or a pharmaceutically acceptable salt, solvate, tautomer, or stereoisomer thereof, wherein Z is —O—, —CH$_2$O—, or —OCH$_2$—.

Embodiment 26. The compound of any one of Embodiments 1-25, or a pharmaceutically acceptable salt, solvate, tautomer, or stereoisomer thereof, wherein $R^3$ is unsubstituted pyridine.

Embodiment 27. The compound of any one of Embodiments 1-26, or a pharmaceutically acceptable salt, solvate, tautomer, or stereoisomer thereof, wherein A is unsubstituted phenyl.

Embodiment 28. The compound of any one of Embodiments 1-27, or a pharmaceutically acceptable salt, solvate, tautomer, or stereoisomer thereof, wherein $R^1$ and $R^2$ are hydrogen.

Embodiment 29. The compound of any one of Embodiments 1, 7, 8, or 10-20, or a pharmaceutically acceptable salt, solvate, tautomer, or stereoisomer thereof, wherein the compound has structural Formula (Ia):

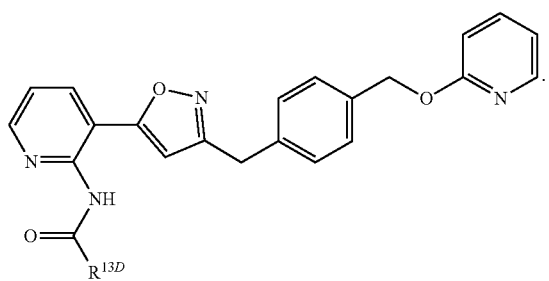

Embodiment 30. The compound of any one of Embodiments 1-7, or a pharmaceutically acceptable salt, solvate, tautomer, or stereoisomer thereof, wherein $R^{13}$ is —C(O)X$^2$R$^{13C}$ Embodiment 31. The compound of any one of Embodiments 1-9 or 30, or a pharmaceutically acceptable salt, solvate, tautomer, or stereoisomer thereof, wherein the compound has structural Formula (Ib):

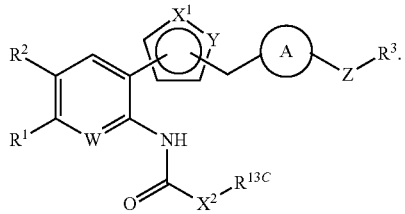

Embodiment 32. The compound of any one of Embodiments 1-9 or 31, or a pharmaceutically acceptable salt, solvate, tautomer, or stereoisomer thereof, wherein $R^{13C}$ is hydrogen, substituted or unsubstituted alkyl, substituted or unsubstituted aryl, or substituted or unsubstituted heteroalkyl.

Embodiment 33. The compound of any one of Embodiments 30-32, or a pharmaceutically acceptable salt, solvate, tautomer, or stereoisomer thereof, wherein a partial structure represented by

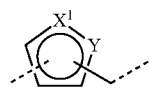

in Formulas (II) and/or (Ib) is

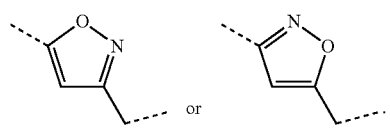

Embodiment 34. The compound of any one of Embodiments 30-33, or a pharmaceutically acceptable salt, solvate, tautomer, or stereoisomer thereof, wherein Z is —O—, —CH$_2$O—, or —OCH$_2$—.

Embodiment 35. The compound of any one of Embodiments 30-34, or a pharmaceutically acceptable salt, solvate, tautomer, or stereoisomer thereof, wherein $R^3$ is unsubstituted pyridine.

Embodiment 36. The compound of any one of Embodiments 30-35, or a pharmaceutically acceptable salt, solvate, tautomer, or stereoisomer thereof, wherein A is unsubstituted phenyl.

Embodiment 37. The compound of any one of Embodiments 30-36, or a pharmaceutically acceptable salt, solvate, tautomer, or stereoisomer thereof, wherein $R^1$ and $R^2$ are hydrogen.

Embodiment 38. The compound of any one of Embodiments 1, 7-9, or 30-32, or a pharmaceutically acceptable salt, solvate, tautomer, or stereoisomer thereof, wherein the compound has structural Formula (Ibb):

(Ibb)

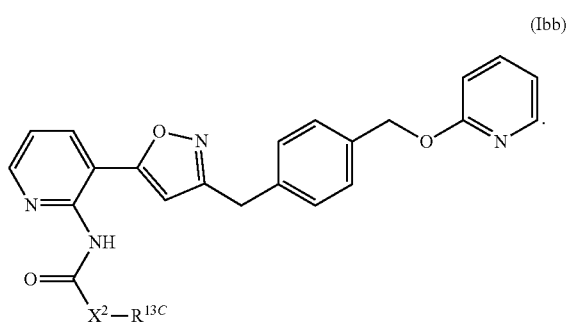

Embodiment 39. A pharmaceutical composition comprising the compound of any one of Embodiments 1-38, or a pharmaceutically acceptable salt, solvate, tautomer, or stereoisomer thereof, and at least one pharmaceutically acceptable carrier.

Embodiment 40. A method of treating a fungal disease or infection, comprising administering to a subject in need thereof a therapeutically effective amount of the compound of any one of Embodiments 1-38, or a pharmaceutically acceptable salt, solvate, tautomer, or stereoisomer thereof, or the pharmaceutical composition of Embodiment 39.

Embodiment 41. The method of Embodiment 40, wherein the fungal disease or infection is caused by a *Cryptococcus*, *Aspergillus*, *Candida*, *Fusarium*, or *Scedosporium* fungus or a fungus from the Mucorales order.

Embodiment 42. The method of Embodiment 40 or 41, wherein the fungal disease or infection is azole-resistant and/or echinocandin-resistant.

Embodiment 43. The method of any one of Embodiments 40-42, further comprising administering at least one antifungal agent in combination with the compound of any one of Embodiments 1-38, or a pharmaceutically acceptable salt, solvate, tautomer, or stereoisomer thereof, or the pharmaceutical composition of Embodiment 39.

Embodiment 44. The method of Embodiment 43, wherein the at least one antifungal agent is an azole, an echinocandin, amphotericin B deoxycholate, amphotericin B cochleate, 5-fluorocytosine, terbinafine, griseofulvin, VL-2397, ibrexafiingerp, orotomide F901318, or combinations thereof.

Embodiment 45. The method of Embodiment 44, wherein the azole is ketoconazole, fluconazole, posaconazole, itraconazole, voriconazole, isavuconazole, or miconazole.

Embodiment 46. The method of Embodiment 44, wherein the echinocandin is caspofungin, anidulafungin, micafungin, or rezafungin.

Embodiment 47. The method of any one of Embodiments 43-46, wherein the compound of any one of Embodiments 1-38, or a pharmaceutically acceptable salt, solvate, tautomer, or stereoisomer thereof, or the pharmaceutical composition of Embodiment 39, and the antifungal agent are administered simultaneously, approximately simultaneously, or sequentially, in any order.

Embodiment 48. The method of Embodiment 47, wherein the compound of any one of Embodiments 1-38, or a pharmaceutically acceptable salt, solvate, tautomer, or stereoisomer thereof, or the pharmaceutical composition of Embodiment 39, and the antifungal agent are administered simultaneously or approximately simultaneously.

Embodiment 49. The method of Embodiment 47, wherein the compound of any one of Embodiments 1-38, or a pharmaceutically acceptable salt, solvate, tautomer, or stereoisomer thereof, or the pharmaceutical composition of Embodiment 39, or a pharmaceutically acceptable salt, solvate, tautomer, or stereoisomer thereof, and the antifungal agent are administered sequentially.

Embodiment 50. The method of Embodiment 49, wherein the compound of any one of Embodiments 1-38, or a pharmaceutically acceptable salt, solvate, tautomer, or stereoisomer thereof, or the pharmaceutical composition of Embodiment 39, or a pharmaceutically acceptable salt, solvate, tautomer, or stereoisomer thereof, is administered before the at least one antifungal agent.

Embodiment 51. The method of Embodiment 49, wherein the compound of any one of Embodiments 1-38, or a pharmaceutically acceptable salt, solvate, tautomer, or stereoisomer thereof, or the pharmaceutical composition of Embodiment 39, or a pharmaceutically acceptable salt, solvate, tautomer, or stereoisomer thereof, is administered after the at least one antifungal agent.

Embodiment 52. The method of any one of Embodiments 40-51, wherein the subject has reduced colony counts of fungi in the lungs after administration of the pharmaceutical composition.

The disclosure will be further understood by the following non-limiting examples.

VII. EXAMPLES

Example I: Chemical Synthesis

Unless otherwise noted, reagents and solvents are used as received from commercial suppliers. Anhydrous solvents and oven-dried glassware are used for synthetic transformations sensitive to moisture and/or oxygen. Yields are not optimized. Reaction times are approximate and are not optimized. Column chromatography and thin layer chromatography (TLC) are performed on silica gel unless otherwise noted.

Example 1: Synthesis of Carbamates, Thiocarbamates, and Ureas

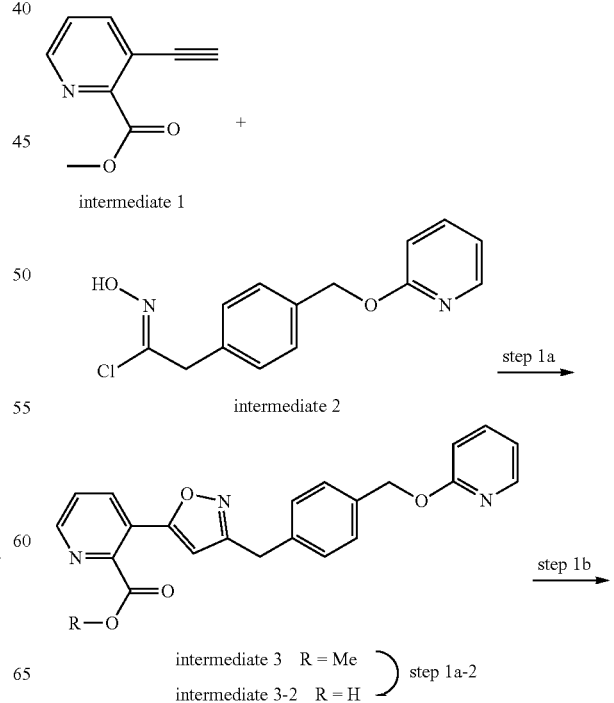

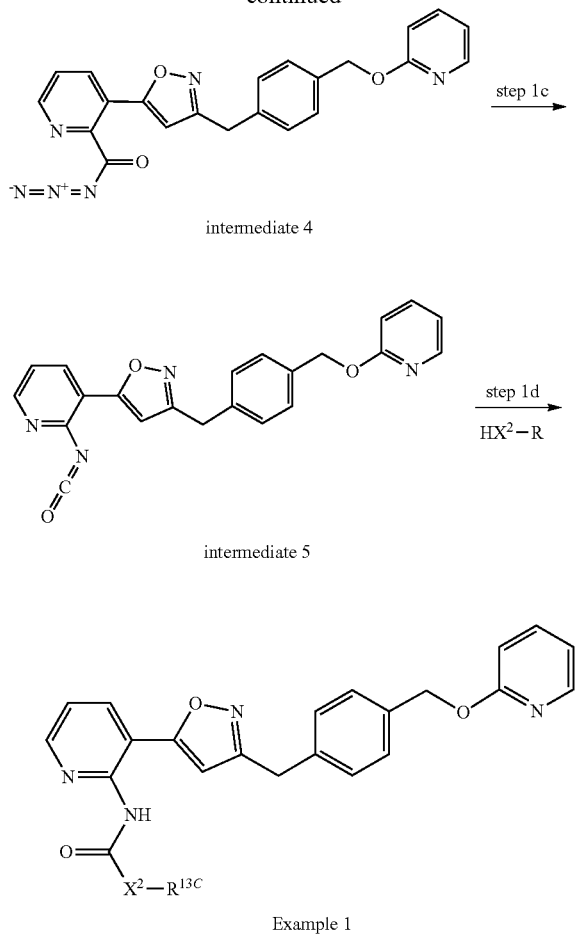

intermediate 4 intermediate 5

Example 1

$X^2$ = O, S, or $NR^{13B}$

Step 1a: To a mixture of zinc chloride (3 eq.) and tetrahydrofuran is added commercially available methyl 3-ethynylpicolinate (intermediate 1, 1 eq.) and 4-(pyridin-2-yloxymethyl)-phenyl)-acetohydroxymoyl chloride (intermediate 2, 1 eq., from U.S. Pat. No. 8,058,444) at 0° C. The reaction mixture is allowed to warm to room temperature and, while the internal temperature is maintained below about 28° C. using a water bath, trimethylamine (2 eq.) was added thereto dropwise. The reaction mixture is stirred at room temperature for 20 minutes, and then is stirred for one hour at 35° C. The reaction mixture is left at room temperature. To the reaction mixture is added an aqueous ammonium chloride solution and ethyl acetate. Then an aqueous ammonia solution is added to bring the pH value to approximately 8. The mixture is extracted with EtOAc. The organic layers are combined and washed with saturated sodium chloride solution, dried over anhydrous magnesium sulfate, and filtered. The filtrate is concentrated under a reduced pressure. The residue is purified by silica gel column chromatography (heptane:ethyl acetate=3:2) to afford the intermediate 3 as an ester.

Step 1a-2: To a solution of intermediate 3 (1 eq.) in THF and water (v/v=2:1) is added LiOH (3 eq.). The mixture is stirred at room temperature overnight, and concentrated in vacuum. The crude is diluted with water, and acidified to pH<4 using an aqueous solution of 2M HCl. This aqueous mixture is extracted with EtOAc twice and the combined organic extracts are washed with brine, dried and concentrated in vacuum to provide intermediate 3-2, as a carboxylic acid.

Step 1b: Under argon, a stirred solution of intermediate 3-2 (1 eq.) and $Et_3N$ (1.3 eq.) in dry THF is cooled to −10° C. Ethyl chloroformate (1.5 eq.) is dropwise added and the resulting mixture is stirred for 2 h. Then a solution of sodium azide (1.7 eq.) in water is added in one portion. After 1 h at −10° C., the reaction is checked for progress. After the reaction is complete, iced water is added to the mixture to quench the reaction. The mixture is extracted with EtOAc three times and the combined organic layers are successively dried, filtered and evaporated under reduced pressure to give the crude acyl azide, intermediate 4.

Step 1c: The crude acyl azide, intermediate 4, is placed in dry toluene and the mixture is heated at reflux for 1 h to give the corresponding crude isocyanate, intermediate 5.

Step 1d: The crude isocyanate, intermediate 5, is dissolved in dry dioxane prior to adding anhydrous EtOH. The mixture is heated at reflux for 24 h. The reaction mixture is cooled to room temperature and the volatiles are removed to dryness in vacuum at about 40° C. The dark residue is purified by silica gel chromatography column ($CH_2Cl_2$/MeOH, v/v=99:1) to afford the carbamate, Example 1. Thiocarbamates and urea derivatives are made similarly by using the appropriate thiol derivatives and amino derivatives. In some cases, some of the functional groups are protected before the Curtius rearrangement reaction, and then they are deprotected. For example, when an amino acid, dipeptide, or tripeptide is used as the nucleophile in the urea formation reaction, the amino acid, dipeptide and tripeptide comprise protection groups. These protection groups are removed after the urea formation reaction.

Example 2: Synthesis of Glycosyl Carbamate

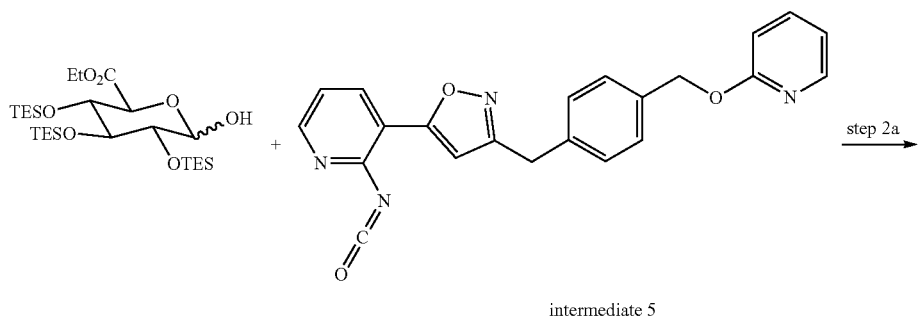

intermediate 5

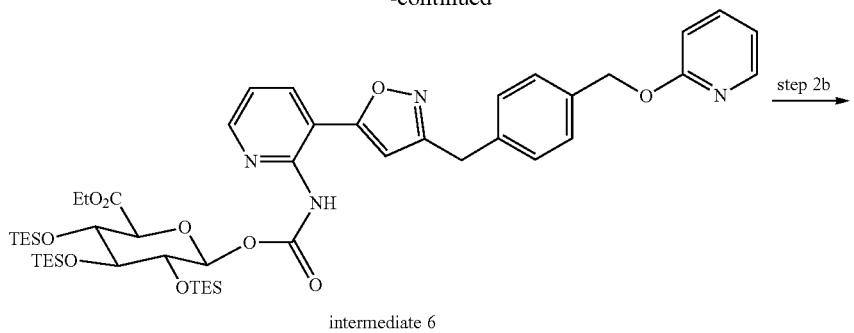

intermediate 6

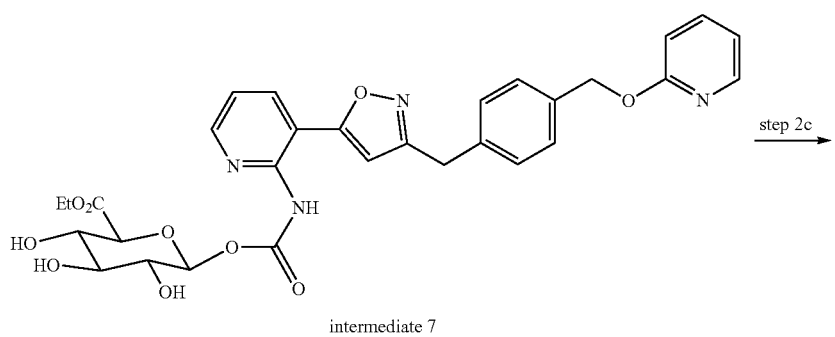

intermediate 7

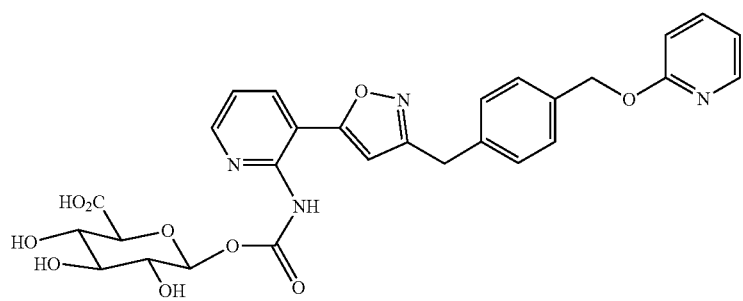

Example 2

Step 2a: Triethylsilyl (TES) ether protected 1-hydroxyl-free glucuronide is obtained according to the procedures disclosed in M. Thomas et al., Bioorg. Med. Chem. 16 (2008), p 8109-16. This sugar moiety is coupled to the isocyanate intermediate 5 as follows. To a solution of the sugar moiety (1 eq.) in anhydrous toluene and Et₃N (5 eq.) cooled to 0° C. is added slowly a solution of the isocyanate intermediate 5 (1.1 eq.) in toluene. After stirring overnight at room temperature, the mixture is evaporated and the residues obtained is purified by flash column chromatography to give the intermediate 6.

Step 2b: A solution of intermediate 6 (1 eq.) in EtOAc/formic acid (v/v—3:2) is stirred overnight. The solvents are removed in vacuum and the residues are purified by flash column chromatography to yield the triol intermediate 7. Intermediate 7 is an example of Formulas (I) and (Ib).

Step 2c: To a solution of intermediate 7 (1 eq.) in EtOH cooled to −40° C. is added 1M NaOH (2 eq.). After the reaction is complete, the solution is neutralized with ion exchange resins, and stirred for 20 min. The resin is removed by filtration and the filtrate is evaporated to dryness to give Example 2.

Example 3: Synthesis of Peptidyl Carbamates

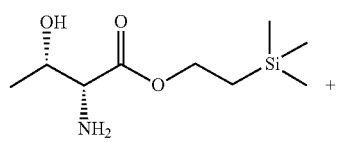

intermediate 8

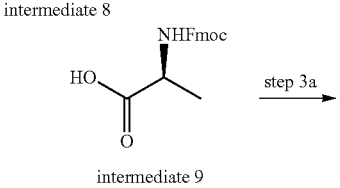

intermediate 9

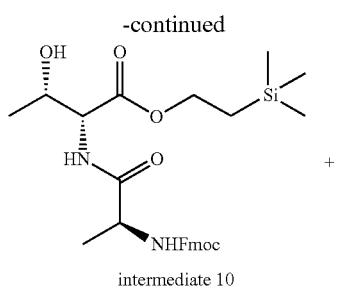

intermediate 10

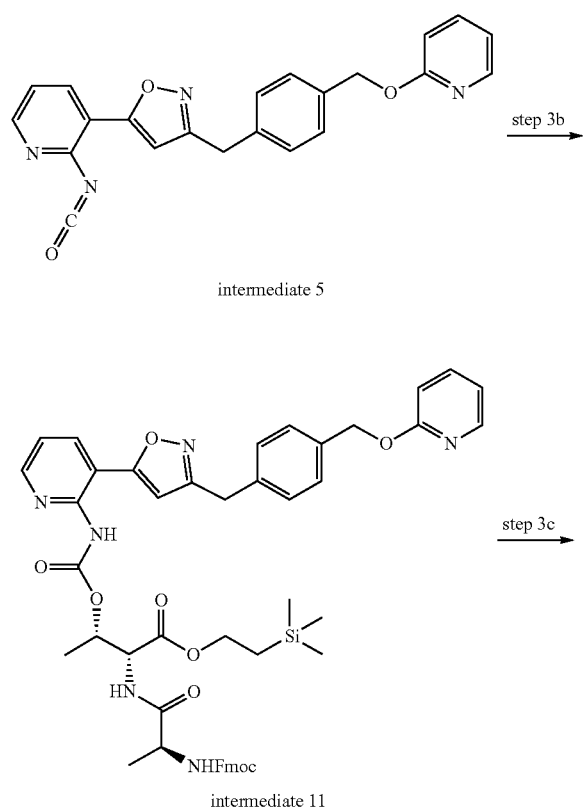

Step 3a. To a solution of amino acid intermediate 9 (1 eq.) in acetonitrile is added Et$_3$N (2 eq.) followed by HATU (1.1 eq.). The mixture is stirred at room temperature for 15 min, then treated with a solution of amino acid intermediate 8. The reaction mixture is stirred at room temperature for 18 h. The mixture is diluted with EtOAc and washed with 1N HCl, and brine. The organic layer is dried, filtered and the filtrate is concentrated. The residue is absorbed onto a plug of silica gel and purified by chromatography to provide intermediate 10, a dipeptide.

The peptide coupling is carried out in the presence of HATU in acetonitrile to afford a dipeptide intermediate 10 bearing a free hydroxyl group. Other peptide coupling conditions are used for different dipeptide formations.

Step 3b. The dipeptide intermediate 10 (1 eq.) is dissolved in anhydrous toluene and treated with Et$_3$N (5 eq.) and cooled to 0° C. To this cooled solution is added slowly a solution of the isocyanate intermediate 5 (1.1 eq.) in toluene. After stirring overnight at room temperature, the mixture is evaporated and the residue obtained is purified by flash column chromatography to give the intermediate 11.

Step 3c. To a solution of intermediate 11 in THF is added TBAF at room temperature. The reaction mixture is stirred at room temperature for 18 h, quenched with water, and concentrated. The residue is partitioned between EtOAc and 0.1N HCl. The combined organic layer is washed with water, dried, and concentrated. The residue is purified by silica gel columns. to give Example 3.

Example 4: Synthesis of Phosphotoxy Carbamate

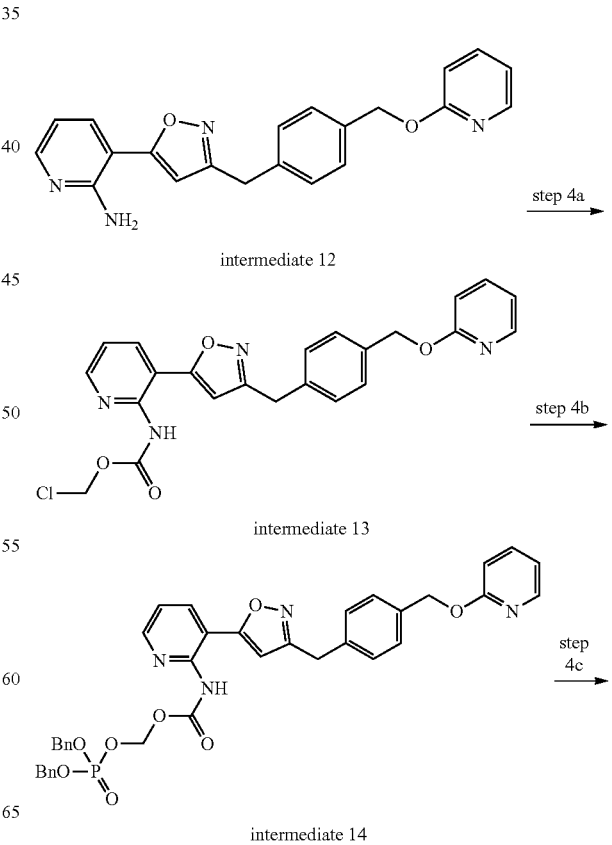

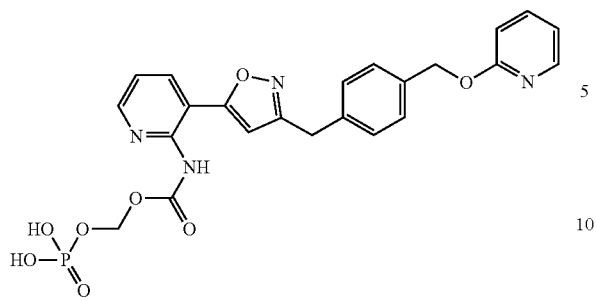

Example 4

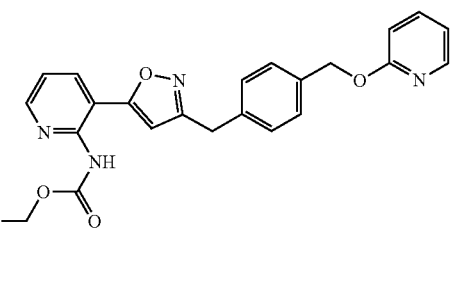

Example 5

Step 4a. Chloromethyl chloroformate (2 eq.) is added to a mixture of intermediate 12 (1 eq, U.S. Pat. No. 8,058,444) and DMAP (2.5 eq.) in dry $CH_2Cl_2$ at 0° C. The reaction mixture is stirred at room temperature overnight. The solvent is removed under reduced pressure and the residue is purified by silica gel column chromatography to afform intermediate 13

Step 4b. The intermediate 13 (1 eq.) and dibenzyl phosphate silver salt (3 eq.) is added to toluene. The resulting mixture is refluxed for 4 h. The solvent is removed under reduced pressure and the residue is purified by column chromatography to give the phosphate triester intermediate 14.

Step 4c. The phosphate trimester intermediate 14 (1 eq.) is dissolved in dry THF. Then $Et_3N$ (10 eq.) and 10% Pd/c (0.2 eq.) are added to the mixture. The mixture is stirred at room temperature under hydrogen overnight. Then the reaction mixture is filtered and concentrated under vacuum to afford Example 4.

Step 5a. To a solution of intermediate 13 (1 eq.) in DMF is added a solution of N-Boc-L-alanine (1.5 eq.), together with $NaHCO_3$ (3.0 eq.) and KI (3.0 eq.) at room temperature. Stirred overnight. The reaction mixture is concentrated to dryness. The residue is partitioned between EtOAc and water. Organic layers are dried, filtered, and concentrated. The residue is purified by flash column chromatography to afford intermediate 15.

Step 5b. The intermediate 15 is dissolved in $CH_2Cl_2$ and treated with TFA. The reaction mixture is stirred at room temperature for 3 h and concentrated. The residue is partitioned between EtOAc and sodium bicarbonate solutions. Organic layers are dried, filtered, and concentrated. The residue is purified by flash column chromatography to give Example 5.

Example 6: Synthesis of Phosphoramidate (1)

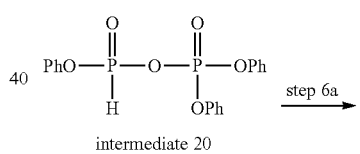

intermediate 20

Example 5: Acyloxy Carbamate

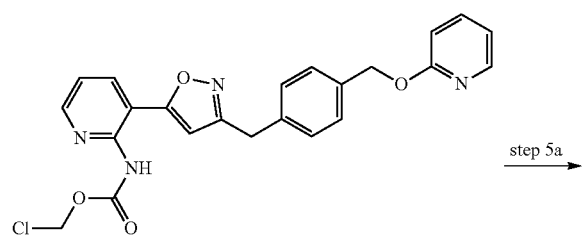

intermediate 13

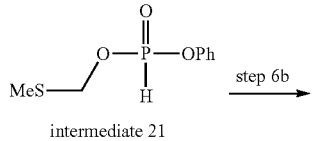

intermediate 21

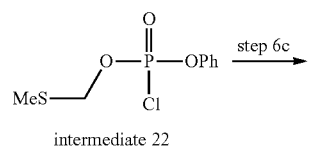

intermediate 22

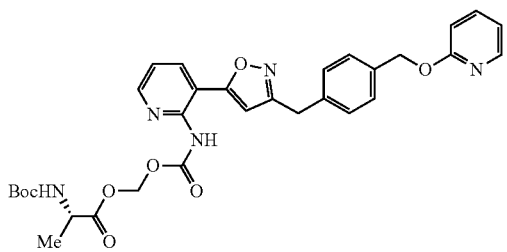

intermediate 15

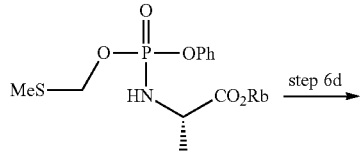

intermediate 23

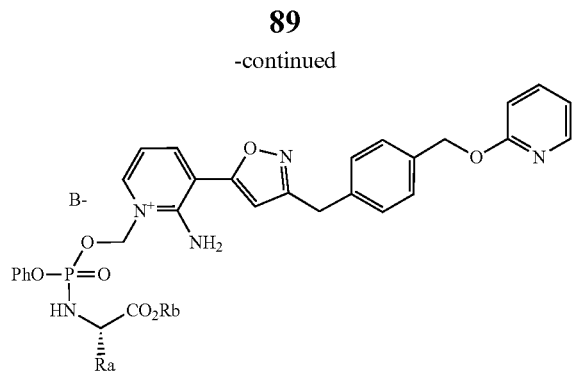

Example 6

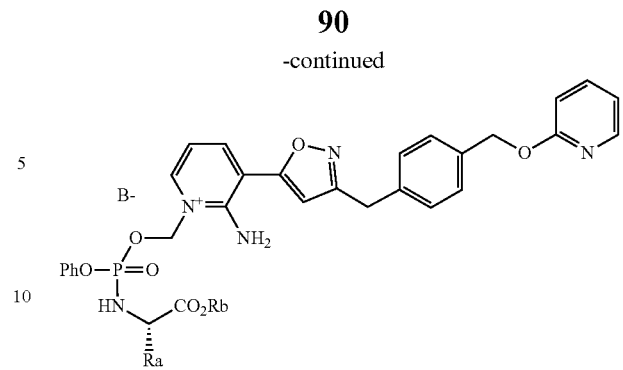

Example 6

Step 6a. To a solution of mixed anhydride intermediate 20 (1 eq.) in THF are added methylthiomethanol (1 eq.) and DBU (2 eq.) at room temperature. The mixture is stirred at room temperature overnight. The mixture is concentrated. The residue is partitioned between $CH_2Cl_2$ and 1N HCl. The organic layers are dried, filtered and concentrated to give phosphite intermediate 21.

Step 6b. To a solution of intermediate 21 (1 eq.) in THF is added N-chlorosuccinimide (1.1 eq.). The reaction mixture is stirred at room temperature overnight and concentrated to afford the crude phosphochloridate intermediate 22.

Step 6c. To the phosphochloridate intermediate 22 (1 eq.) in $CH_2Cl_2$ and $Et_3N$ is added a solution of L-alanine isopropyl ester. The reaction mixture is stirred overnight and concentrated. The residue is partitioned between $CH_2Cl_2$ and 1N HCl. The organic layers are dried, filtered and concentrated. The residue is purified by column chromatography to give the phosphoramidate intermediate 23.

Step 6d. The intermediate 23 (1 eq.) is dissolved in $CH_2Cl_2$ at 0° C. To this solution is added sulfuryl chloride (0.99 eq.) slowly, and the resulting mixture is stirred at 0° C. for 10 min. Additional sulfuryl chloride (0.05 eq.) is added and the mixture is stirred for another 10 mm. The resulting mixture is added via cannula into a flask containing a stirred solution of intermediate 12 (1 eq.) in THF in the presence of sodium iodide (2.0 eq.) and DIPEA (2 eq.). When the reaction is complete, the mixture is concentrated, and the residue is partitioned between EtOAc and water. The organic layers are dried, filtered, and concentrated. The residue is purified by a combination of silica gel chromatography and HPLC purification to give Example 6.

Example 7: Synthesis of Phosphoramidate (2)

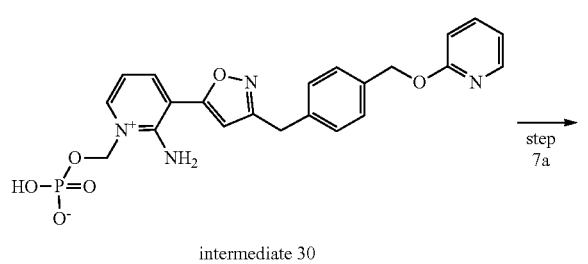

intermediate 30

Step 7a. The pyridinium salt intermediate 30 (1 eq., at 0.1 M concentration, U.S. Pat. No. 8,513,287) is suspended in $CH_2Cl_2$. To the suspension are added phenol (0.95 eq.) and 2,4,6-masitylenesulfonyl-3-nitro-1,2,4-triazelide (MSNT, 8 eq.) in the presence of 1-methyltmidazole (MeIm, 6 eq). The reaction mixture is stirred at room temperature overnight. L-alanine isopropyl ester (1 eq.) is added to the reaction mixture and the mixture is stirred for another 18 h and concentrated. The residue is purified by recrystallization to give the phosphoramidite prodrug Example 6.

Example 8: Synthesis of Phosphoramidate (3)

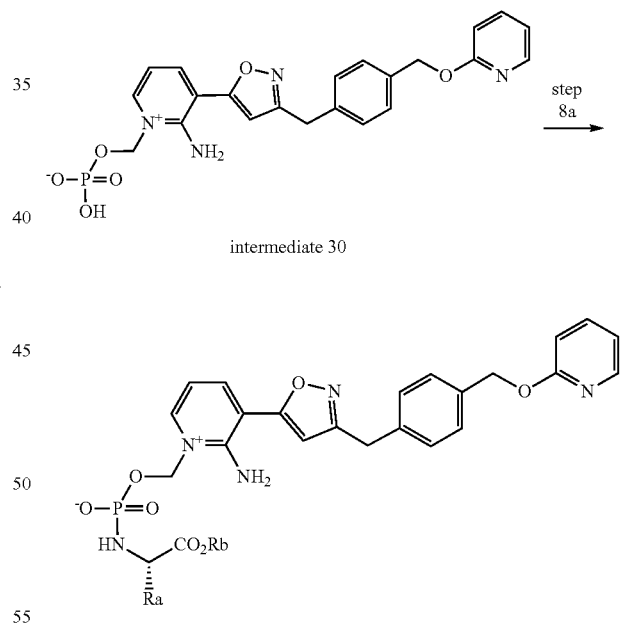

intermediate 30

Example 8

Step 8a. The pyridinium salt intermediate 30 (1 eq., at 0.1 M concentration, U.S. Pat. No. 8,513,287) is suspended in $CH_2Cl_2$. To the suspension are added L-alanine isopropyl ester (1 eq.) and 2,4,6-masitylenesulfonyl-3-nitro-1,2,4-triazelide (MSNT, 8 eq.) in the presence of 1-methyltmidazole (MeIm, 6 eq.). The reaction mixture is stirred at room temperature overnight and concentrated. The residue is purified by recrystallization to give the phosphoramidite prodrug Example 8.

Example 9: Synthesis of Double Prodrug

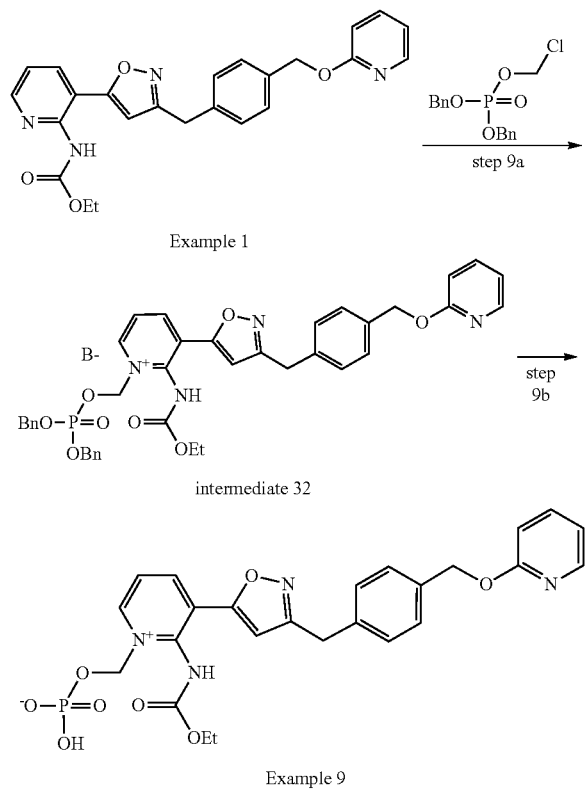

Example 1 intermediate 32

Example 9

Step 9a. Dibenzyl (chloromethyl) phosphate (1.5 eq.) is added via cannula into a flask containing a stirred solution of Example 1 (1 eq.) in THF in the presence of sodium iodide (2.0 eq.) and DIPEA (2 eq.). When the reaction is complete, the mixture is concentrated, and the residue is partitioned between EtOAc and water. The organic layers are dried, filtered, and concentrated. The residue is purified by a combination of silica gel chromatography and HPLC purification to give intermediate 32.

Step 9b. The intermediate 32 is suspended in THF/EtOH (v/v=1:1) and hydrogenated over 10% Pd/C overnight. The mixture is filtered to remove the catalyst. The cake is washed with EtOH and water. The combined filtrates are concentrated. The residue is recrystallized from water to give Example 9.

Example II: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as an optional acid or base to adjust the pH. The mixture is incorporated into a dosage unit form suitable for administration by injection.

Example III: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example IV: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example V: Oral Capsule

To prepare a pharmaceutical composition for oral delivery, 10-500 mg of a compound described herein, or a pharmaceutically acceptable salt thereof, is mixed with starch or another suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into a Size 4 capsule, or a size 1 capsule (hypromellose or hard gelatin) and the capsule is closed.

Example VI: Topical Gel Composition

To prepare a pharmaceutical topical gel composition, a compound described herein, or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

Example VII: Inhalation Composition

To prepare a pharmaceutical composition for inhalation delivery, a compound described herein, or a pharmaceutically acceptable salt thereof, is mixed with anhydrous citric acid and 0.9% sodium chloride solution. The mixture is incorporated into an inhalation delivery unit, such as a nebulizer, which is suitable for inhalation administration.

Example VIII: Ophthalmic Solution Composition

To prepare a pharmaceutical ophthalmic solution composition, a compound described herein, or a pharmaceutically acceptable salt thereof, is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Biological Assays

Example IX: In Vitro Antifungal Assay

Measurement of antifungal activity: Antifungal activity of the compounds is evaluated in a microdilution broth assay per Clinical and Laboratory Standard Institute methodology for yeasts and molds.

Preparation of Fungal Suspension: Strains are streaked from frozen stocks at −80° C. onto Sabouraud Dextrose Agar (SDA) plates. These are allowed to grow for 24-48 h at 35° C. before using them in the assay. 5-6 individual colonies are picked and diluted into sterile water to obtain a fungal suspension. The cell density of the suspension is determined and the culture diluted with RPMI1640 medium to obtain a fungal suspension of $2.5 \times 10^3$ cells/mL. The suspension is used in the MIC measurement as described below.

Spores from a −80° C. frozen stock are spread onto a Potato Dextrose Agar (PDA) plate and incubated for 4-5 days at 25° C. Water containing 1% Tween is directly added to the agar plate and gently agitated. The conidia and hyphal fragments are collected, followed by removal of hyphal fragments. The resulting suspension is counted and diluted into RPMI1640 medium to adjust to a final suspension of $2 \times 10^4$ conidia/mL. The suspension is used in the MIC measurement as described below.

Preparation of Compound Stocks and Intermediate Dilutions: The compounds are weighed and DMSO is added to prepare a 10 mg/mL stock. The solutions are mixed by vortexing and sonication at 37° C. for 5-10 mins. The resulting solutions are sterile filtered using a PTFE filter, and aliquoted (12 µL or as needed) and stored at −20° C. Intermediate compound dilutions are prepared in sterile polypropylene tubes in 100% DMSO. The compound stock solution is first diluted in DMSO to obtain a concentration of 1600 µg/mL. This is further 2-fold serially diluted to obtain a dilution series from 800 to 0.19 µg/mL.

MIC/MEC Measurement: 99 µL of the fungal suspension in RPMI1640 prepared as above is added to each well of a 96-well round bottom assay plate. 1 µL of the intermediate compound dilutions (200-0.19 µg/mL) are added to wells of the plate. This leads to a 100-fold dilution of the intermediate dilutions resulting in a final compound concentration of 2-0.0019 µg/mL in the plate. 1 µL of DMSO is added to "No drug" control wells. The solutions are mixed by shaking on a plate shaker for 10 mins and the plates are incubated at 35° C. for 40-48 h or 72 h. The minimum concentration that clearly inhibits fungal growth (>50% inhibition) as compared to the control by visual inspection is determined as the minimum inhibitory concentration (MIC) for yeasts and molds. The minimum concentration that leads to shortening of hyphae as compared to hyphal growth in DMSO control wells is determined as the minimum effective concentration (MEC). The use of the MIC and MEC endpoints against yeasts and molds, respectively, has been described by Pfaller M A, Duncanson F, Messer S A, Moet G J, Jones R N, Castanheira M. Antimicrob Agents Chemother. 2011. 55(11):5155-8.

Example X: Systemic Yeast Infection Model in Mice

Preparation of Fungal Inoculant

Yeast is subcultured in brain heart infusion broth and grown at 37° C. overnight. Cells are collected by centrifugation and washed three times with sterilized physiological saline and counted with a hemocytometer. The suspension is adjusted to $2 \times 10^7$ cells/mL with sterilized physiological saline to serve as the fungal inoculum.

Infection 8-week-old BALB/c mice weighing ~20 g are rendered neutropenic by receiving 150 mg/kg and 100 mg/kg of cyclophosphamide via IP injection on day −4 and day −1 prior to infection, respectively. The fungal inoculum is used in the amounts of 0.2 mL ($4 \times 10^6$ cells/mouse).

Treatment

From 0.5 to 1 hour after fungal inoculation, 0.2 mL of agent solution containing a compound described herein (dissolved or suspended in sterilized physiological saline and 3.5% Tween 80 or another appropriate vehicle) is administered orally using a peroral probe, 3 times every 4 hours. The agent concentration ranges from 1 mg/kg to 500 mg/kg, and the number of animals in one group ranges from 5 to 10 animals.

Determination of Effects

Animals are sacrificed after 48 hrs and organs such as kidney and brain are harvested. Colony forming units/gram of tissue are determined in order to assess the protective effect of a compound vs a no drug (vehicle) control.

Example XI: Murine Model of Cryptococcal Meningitis

Preparation of Fungal Inoculant

*Cryptococcus neoformans* strain H99 is grown in YPD broth at 30° C. on a shaker (220 rpm) for 24 hours, centrifuged (1980 ref) and washed twice in PBS, resuspended in PBS, and quantified by hemacytometric count.

Infection and Treatment

CD-1 male mice are infected with $6 \times 10^4$ colony forming units (CFU) per mouse via lateral tail vein injection of 100 µL. Compounds are administered by oral, intraperitoneal or intravenous routes from 1 to 3 times daily. Treatments are given for seven days.

Determination of Effects

Mice are sacrificed on day 8, and brain and left lung are homogenized and cultured for quantitative determination of tissue burden (CFU per gram of tissue). Colony forming units/gram of tissue are determined in order to assess the protective effect of a compound vs a no drug (vehicle) control.

Example XII: Clinical Trial of a Compound Described Herein in Patients with a Fungal Infection The purpose of this study is to investigate whether a compound described herein can treat patients with fungal infections. Another purpose of this study is to assess the safety, tolerability, pharmacokinetics, bioavailability and food effect of single doses of a compound described herein administered intravenously and orally, followed by an evaluation of the safety, tolerability, pharmacokinetics and drug-drug interaction potential of multiple doses of a compound described herein administered orally.

Study Type:
Interventional
Study Design:
Allocation: Randomized
Interventional Model: Crossover Assignment
Masking: Double (Participant Investigator)
Primary Purpose: Treatment
Primary Outcome Measures:
Safety and tolerability of single and multiple oral doses of a compound described herein as measured by adverse events (AEs), physical examinations (PE), vital signs (VS), laboratory safety tests, urinalysis and 12-lead electrocardiograms (ECG). Time Frame: 21 days.
Secondary Outcome Measures:
Pharmacokinetics of single and multiple doses of a compound described herein as measured by maximum observed concentration ($C_{mx}$). Time Frame: 21 days Pharmacokinetics of single and multiple dose of a compound described herein as measured by area under the curve (AUC). Time Frame: 21 days Pharmacokinetics of single and multiple doses of a compound described herein as measured by terminal half life ($t_{1/2}$). Time Frame: 21 days Pharmacokinetics of single and multiple doses of a compound described herein as measured by volume of distribution ($V_d$). Time Frame: 21 days Pharmacokinetics of single and multiple doses of a compound described herein as measured by elimination rate constant ($K_e$). Time Frame: 21 days Pharmacokinetics of single and multiple doses of a compound described herein as measured by accumulation ratio. Time Frame: 21 days Eligibility:
Ages Eligible for Study: 18 Years to 55 Years (Adult)
Sexes Eligible for Study: All
Accepts Healthy Volunteers: Yes
Inclusion Criteria:
  Women of childbearing potential must agree to avoid pregnancy during the study and to use contraception at least 2 weeks before the start of the study until 3 months after the last dose of study drug.
  Males with partner(s) of childbearing potential must agree to use appropriate barrier contraception from the screening period until 3 months after the last dose of study drug.
  Screening hematology, clinical chemistry, coagulation and urinalysis consistent with overall good health.
  No significantly abnormal findings on physical examination, ECG and vital signs.
  Willing and able to provide written informed consent.
Exclusion Criteria:
  Any uncontrolled or active major systemic disease including, but not limited to: cardiovascular, pulmonary, gastrointestinal, metabolic, urogenital, neurological, immunological, psychiatric, or neoplastic disorder with metastatic potential.
  History or presence of malignancy within the past year. Subjects who have been successfully treated with no recurrence of basal cell carcinoma of the skin or carcinoma in-situ of the cervix may be enrolled.
  Use of prescription medication within 14 days prior to the first dose of study drug and throughout the study.
  Use of non-prescription or over-the-counter medications within 7 days prior to the first dose of study drug and throughout the study.

Although the invention has been described with reference to the above examples, it will be understood that modifications and variations are encompassed within the spirit and scope of the invention. Accordingly, the invention is limited only by the following claims.

What is claimed is:

1. A compound having formula (Ib), or a pharmaceutically acceptable salt, solvate, tautomer, or stereoisomer thereof:

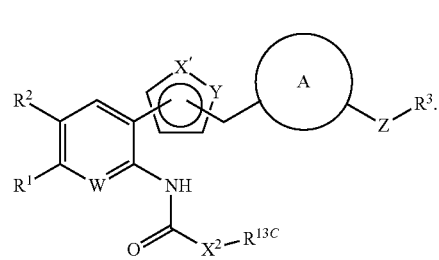

(Ib)

wherein:
one of $X^1$ and Y is nitrogen while the other is nitrogen or oxygen;
W is N or $N^+$—$R^{15}$;
A is substituted or unsubstituted phenyl or substituted or unsubstituted pyridinyl;
Z is a bond, —(CH$_2$)—, —(CH$_2$)$_2$—, —O—, —S—, —CH$_2$O—, —OCH$_2$—, —NH—, —CH$_2$NH—, —NHCH$_2$—, —CH$_2$S—, or —SCH$_2$—;
$R^1$ is hydrogen, halogen, —NR$^{1B}$R$^{1C}$, —C(O)NR$^{1B}$R$^{1C}$, —OR$^{1A}$, substituted or unsubstituted alkyl, or substituted or unsubstituted heteroalkyl;
$R^2$ is hydrogen or halogen;
$R^3$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$X^2$ is selected from —O—, —S—, or —NR$^{13B}$;
$R^{15}$ is —SO$_{n15}$R$^{15A}$, —SO$_{v15}$NR$^{15B}$R$^{15C}$, —C(O)R$^{15D}$, —C(S)R$^{15D}$, —C(O)OR$^{15D}$, —C(S)OR$^{15D}$, —C(O)SR$^{15D}$, —C(O)NR$^{15B}$R$^{15C}$, —C(S)NR$^{15B}$R$^{15C}$, —CH$_2$OPO$_3$H$_2$, —CH$_2$OSO$_3$H, —CH$_2$OPO$_3$H$^-$, —CH$_2$OSO$_3^-$, —C(O)CH$_2$X$_3$, or substituted or unsubstituted heteroalkyl;
$X^3$ is —F, —Cl, —Br, —I, —CHF$_2$, —CHCl$_2$, —CHBr$_2$, —CHI$_2$, —CF$_3$, —CCl$_3$, —CBr$_3$, —CI$_3$, or —NO$_2$;
n15 is an integer from 0 to 4;
v15 is 1 or 2; and
$R^{1A}$, $R^{1B}$, $R^{1C}$, $R^{13B}$, $R^{13C}$, $R^{15A}$, $R^{15B}$, $R^{15C}$, and $R^{15D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or
$R^{13B}$ and $R^{13C}$ or $R^{15B}$ and $R^{15C}$ substituents bonded to the same nitrogen atom may optionally be joined to form a substituted or unsubstituted heterocycloalkyl or substituted or unsubstituted heteroaryl.

2. The compound of claim 1, wherein W is $N^+$—$R^{15}$.

3. The compound of claim 2, wherein $R^{15}$ is:

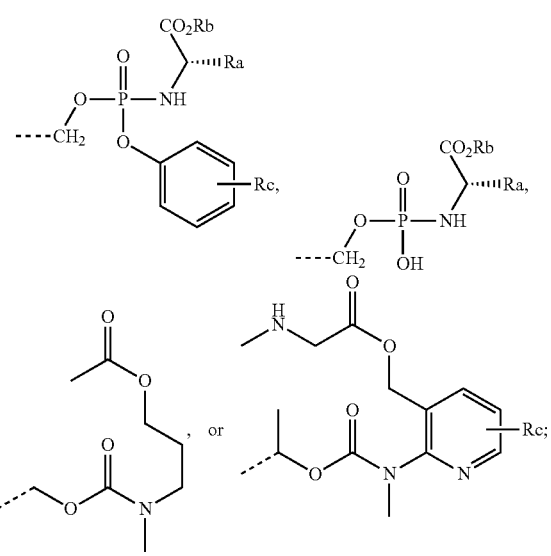

wherein:

Ra is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a side chain of a natural amino acid; and Rb and Rc are independently hydrogen, halogen, hydroxy, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

4. The compound of claim 1, wherein W is N.

5. The compound of claim 1, wherein:

$X^2$ is —O—; and $R^{13C}$ is substituted or unsubstituted phenyl.

6. The compound of claim 1, wherein:

[structure] is [structure] or [structure];

Z is —O—, —CH$_2$O—, or —OCH$_2$—;

$R^3$ is unsubstituted pyridine;

A is unsubstituted phenyl; and $R^1$ and $R^2$ are independently hydrogen.

7. The compound of claim 1, wherein $R^{13C}$ is hydrogen, substituted or unsubstituted alkyl, substituted or unsubstituted aryl, or substituted or unsubstituted heteroalkyl.

8. The compound of claim 7, wherein:

[structure] is [structure] or [structure];

Z is —O—, —CH$_2$O—, or —OCH$_2$—;

$R^3$ is unsubstituted pyridine;

A is unsubstituted phenyl; and $R^1$ and $R^2$ are independently hydrogen.

9. The compound of claim 1, wherein the compound has structural Formula (Ibb):

(Ibb)

[structure]

10. A pharmaceutical composition, comprising:

the compound of claim 1; and at least one pharmaceutically acceptable carrier.

11. A method of treating a subject having a fungal disease or infection, the method comprising:

administering to therapeutically effective amount of the compound of claim 1.

12. The method of claim 11, wherein the fungal disease or infection is caused by a *Cryptococcus, Aspergillus, Candida, Fusarium*, or *Scedosporium* fungus or a fungus from the Mucorales order.

13. The method of claim 11, wherein the fungal disease or infection is azole-resistant and/or echinocandin-resistant.

14. The method of claim 11, comprising:

administering at least one additional antifungal agent in combination with the compound of claim 1.

\* \* \* \* \*